(12) United States Patent
Shia et al.

(10) Patent No.: US 10,882,854 B2
(45) Date of Patent: Jan. 5, 2021

(54) HETEROCYCLIC COMPOUNDS AND USE THEREOF

(71) Applicant: National Health Research Institutes, Miaoli County (TW)

(72) Inventors: Kak-Shan Shia, Taipei (TW); Chien-Huang Wu, New Taipei (TW); Ming-Chen Chou, New Taipei (TW); Jen-Shin Song, Taipei (TW); Yun Wang, Miaoli (TW); Chuan Shih, Carmel, IN (US)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 15/864,707

(22) Filed: Jan. 8, 2018

(65) Prior Publication Data
US 2018/0208588 A1    Jul. 26, 2018

Related U.S. Application Data

(60) Provisional application No. 62/444,601, filed on Jan. 10, 2017.

(51) Int. Cl.
| | | |
|---|---|---|
| *C07D 403/14* | (2006.01) | |
| *C07D 413/14* | (2006.01) | |
| *C07D 473/16* | (2006.01) | |
| *A61P 35/02* | (2006.01) | |
| *A61P 9/10* | (2006.01) | |
| *A61P 13/12* | (2006.01) | |
| *A61P 25/00* | (2006.01) | |
| *A61P 35/00* | (2006.01) | |

(52) U.S. Cl.
CPC .............. *C07D 413/14* (2013.01); *A61P 9/10* (2018.01); *A61P 13/12* (2018.01); *A61P 25/00* (2018.01); *A61P 35/00* (2018.01); *A61P 35/02* (2018.01); *C07D 473/16* (2013.01)

(58) Field of Classification Search
CPC ... C07D 239/95; C07D 403/14; A61K 31/517
USPC ................... 544/284, 292; 514/266.2, 266.4
See application file for complete search history.

(56) References Cited

U.S. PATENT DOCUMENTS

| 7,589,197 B2 | 9/2009 | Yen et al. |
|---|---|---|
| 9,862,703 B2 * | 1/2018 | Shia ...................... C07D 401/14 |
| 9,926,298 B2 * | 3/2018 | Shia ...................... C07D 401/14 |
| 2006/0148801 A1 | 7/2006 | Hsieh et al. |
| 2009/0264339 A1 | 10/2009 | Yen et al. |
| 2010/0221259 A1 | 9/2010 | Habashita et al. |
| 2016/0083369 A1 | 3/2016 | Shia et al. |

FOREIGN PATENT DOCUMENTS

| WO | WO 2008/001070 | 1/2008 |
|---|---|---|
| WO | WO 2010/022121 | 2/2010 |

OTHER PUBLICATIONS

Lister et al., CAPLUS 54:50455 (1960).*
Chalmers et al., CAPLUS 80:48699 (1974).*
Narr et al., CAPLUS 83:43369 (1975).*
Meyer et al., CAPLuS 106:102312 (1987).*
McCall et al., CAPLUS 108:6287 (1988).*
El-Kerdawy et al., CAPLUS 109:170352 (1988).*
Popova et al., CAPLUS 126:277444 (1997).*
Habashita et al., CAPLUS 141:71555 (2004).*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Johnson et al., Relationships between drug activity in NCI preclinical in vitro and in vivo models and early clinical trials, British Journal of Cancer (2001) 64(10): 1424-1431.*
Gura, Systems for identifying New Drugs Are Often Faulty, Cancer Models, Science, vol. 278, No. 5340, pp. 1041-1042, Nov. 1997.*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Merck Manual Professional Online Edition, Acute Leukemia, 6 pages, 2013.*
Wu, et al., "A Novel CXCR4 Antagonist CX549 Induces Neuroprotection in Stroke Brain," Cell Transplantation, vol. 26, pp. 571-583, 2017.
Wu, et al., "Discovery of Novel Stem Cell Mobilizers that Target the CXCR4 Receptor," ChemMedChem 2012, 7, 209-212.
Wu, et al., "Stem Cell Mobilizers Targeting Chemokine Receptor CXC4: Renoprotective Application in Acute Kidney Injury," Journal of Medicinal Chemistry, 2015, 58, 2315-2325.
Search Report dated Jun. 15, 2018 in International counterpart application No. PCT/US2018/012748, filed Jan. 8, 2018.

* cited by examiner

*Primary Examiner* — Deepak R Rao
(74) *Attorney, Agent, or Firm* — Cesari & McKenna, LLP

(57) ABSTRACT

Heterocyclic compounds of Formula (I) shown herein. Also disclosed is a pharmaceutical composition containing one of the heterocyclic compounds. Further disclosed are methods of using one of the heterocyclic compounds for mobilizing hematopoietic stem cells and endothelial progenitor cells into the peripheral circulation, and for treating tissue injury, cancer, inflammatory disease, and autoimmune disease.

31 Claims, No Drawings

HETEROCYCLIC COMPOUNDS AND USE THEREOF

CROSS REFERENCE TO RELATED APPLICATION

This application claims the benefit of U.S. Provisional Application No. 62/444,601, filed on Jan. 10, 2017, the content of which is hereby incorporated by reference in its entirety.

BACKGROUND

Chemokines regulate the trafficking of various types of mononuclear cells. They are classified into four subfamilies, i.e., CC, CXC, CX3C, and C, based on positions of conserved cysteine residues in their N-termini.

Stromal-derived factor-1 (SDF-1 or CXCL12), a CXC chemokine consisting of 67 amino acid residues, is primarily expressed in bone marrow, the central nervous system, and the periphery. CXCL12 serves as a specific ligand to type 4 CXC chemokine receptor (CXCR4), a G protein-coupled receptor with seven transmembrane domains on the surface of many types of stem cells. The CXCR4/CXCL12 axis plays key roles in regulating cancer metastasis, stem cell homing, trafficking, and mobilization. The interaction between CXCR4 and CXCL12 contributes to multiple pathological conditions, such as HIV (Schols et al., *J. Exp. Med.* 186:1383-1388 (1997); Wu et al., *J. Med. Chem.* 58:1452-1465 (2015)), rheumatoid arthritis (Lenoir et al., *J. Immunol.* 172:7136-7143 (2004)), asthma (Gonzalo et al., *J. Immunol.* 165:499-508 (2000)), and tumor metastases (Müller et al., *Nature.* 410:50-56 (2001); Liang et al., *Cancer Res.* 65:967-971 (2005)).

CXCR4 antagonists, which disrupt the interaction between CXCR4 and CXCL12, are able to mobilize various types of mononuclear cells, including hematopoietic stem cells, endothelial progenitor cells, and mesenchymal stem cells, out of bone marrow to peripheral blood. For example, a CXCR4 antagonist AMD3100 (plerixafor) has been used clinically in peripheral blood stem cell (PBSC) transplantation to help patients with haematological malignancies, such as non-Hodgkin's lymphoma or multiple myeloma. PBSC transplantation is a typical medical procedure by which healthy stem cells, particularly CXCR4$^+$/CD34$^+$ hematopoietic stem cells, are mobilized from bone marrow to peripheral blood for collection upon treatment with CXCR4 antagonists, followed by autologous transplantation into cancer patients after radiotherapy or chemotherapy treatment to rapidly restore their immune system.

Compounds that disrupt the interaction between CXCR4 and CXCL12 can be used for treating various diseases including tissue injury (Lin et al., *J. Invest. Dermatol.* 134:2458-2468 (2014)), inflammatory disease (Lukacs et al., *Am. J. Pathol.* 160:1353-1360 (2002)), ischemic disease (Huang et al., *Stroke.* 44:190-197 (2013); Wu et al., *J. Med. Chem.* 58:2315-2325 (2015); Wu et al., *Cell Transplantation.* in press (2017)), cancer (Chen et al., *Hepatology.* 59:1435-1447 (2014)), and autoimmune disease (Matthys et al., *J. Immunol.* 167:4686-4692 (2001)).

There is a need to develop new compounds that can effectively disrupt the interaction between CXCR4 and CXCL12.

SUMMARY

The present invention is based on an unexpected discovery that certain heterocyclic compounds can effectively bind to CXCR4, thus disrupting the interaction between CXCR4 and CXCL12.

In one aspect, this invention relates to heterocyclic compounds of Formula (I):

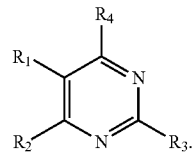

In this formula, each of $R_1$ and $R_2$, independently, is H, halo, $NO_2$, CN, $NH_2$, $C_{1-6}$ alkyl, $C_{1-6}$ alkoxyl, $C_{3-10}$ cycloalkyl, $C_{1-10}$ heterocycloalkyl, aryl, or heteroaryl; or $R_1$ and $R_2$, together with the two carbon atoms to which they are bonded, are $C_{5-10}$ cycloalkyl, $C_{3-10}$ heterocycloalkyl, aryl, or heteroaryl, each of the $C_{1-6}$ alkyl, $C_{1-6}$ alkoxyl, $C_{3-10}$ cycloalkyl, $C_{1-10}$ heterocycloalkyl, $C_{5-10}$ cycloalkyl, $C_{3-10}$ heterocycloalkyl, aryl, and heteroaryl being optionally substituted with halo, $NO_2$, CN, $NH_2$, $C_{1-6}$ alkyl, $C_{1-6}$ alkoxyl, aryl, heteroaryl, or $C(O)OR_a$, in which $R_a$ is H, $C_{1-10}$ alkyl, $C_{3-10}$ cycloalkyl, $C_{3-10}$ heterocycloalkyl, aryl, or heteroaryl; and each of $R_3$ and $R_4$, independently, is

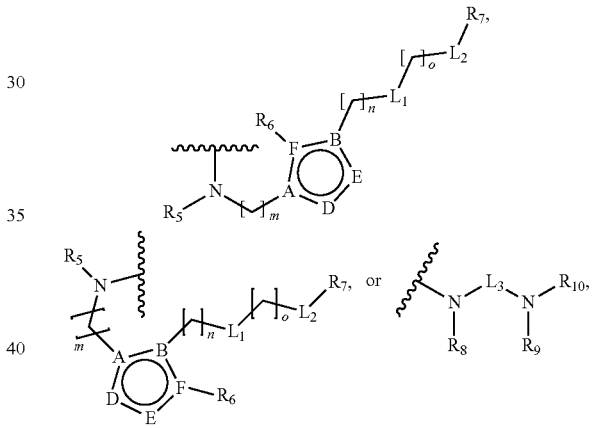

in which $R_5$ is H, $C_{1-6}$ alkyl, $C_{3-10}$ cycloalkyl, $C_{1-10}$ heterocycloalkyl, aryl alkyl, heteroaryl alkyl, aryl, or heteroaryl, each of the $C_{1-6}$ alkyl, $C_{3-10}$ cycloalkyl, $C_{1-10}$ heterocycloalkyl, aryl alkyl, heteroaryl alkyl, aryl, and heteroaryl being optionally substituted with halo, nitro, cyano, amino, $C_{1-6}$ alkyl, $C_{1-6}$ alkoxyl, $C_{3-10}$ cycloalkyl, $C_{1-10}$ heterocycloalkyl, aryl, or heteroaryl; $R_6$ is deleted, H, $C_{1-6}$ alkyl, $C_{1-6}$ alkoxyl, $C_{3-10}$ cycloalkyl, $C_{1-10}$ heterocycloalkyl, aryl, or heteroaryl, each of the $C_{1-6}$ alkyl, $C_{1-6}$ alkoxyl, $C_{3-10}$ cycloalkyl, $C_{1-10}$ heterocycloalkyl, aryl, and heteroaryl being optionally substituted with hydroxy, hydroxy $C_{1-6}$ alkyl, halo, nitro, cyano, or amino; $R_7$ is H, $C_{1-6}$ alkyl, $C_{1-6}$ alkoxyl, $C_{3-10}$ cycloalkyl, $C_{1-10}$ heterocycloalkyl, aryl, or heteroaryl, each of the $C_{1-6}$ alkyl, $C_{1-6}$ alkoxyl, $C_{3-10}$ cycloalkyl, $C_{1-10}$ heterocycloalkyl, aryl, and heteroaryl being optionally substituted with hydroxy, hydroxy $C_{1-6}$ alkyl, halo, nitro, cyano, amino, amino $C_{1-6}$ alkyl, amino $C_{3-10}$ cycloalkyl, amino $C_{1-10}$ heterocycloalkyl, $C_{3-10}$ cycloalkyl, $C_{1-10}$ heterocycloalkyl, aryl, or heteroaryl; each of A and B, independently, is C or N; each of D, E and F, independently, is C, N, O, or S; each of $L_1$ and $L_2$, independently, is heteroaryl, $C_{1-10}$ heterocycloalkyl, or $NR_d$, in which $R_d$ is H or $C(O)(CH_2)_2CHNH_2CO_2R_e$, $R_e$ being H, $C_{1-6}$ alkyl, $C_{3-10}$ cycloalkyl, $C_{3-10}$ heterocycloalkyl, aryl, or heteroaryl; each of m, n, and o, independently, is 1, 2, 3, 4, 5, or 6; each of $R_8$ and $R_9$, independently, is H, $C_{1-6}$ alkyl, $C_{3-10}$ cycloalkyl, $C_{1-10}$ heterocycloalkyl, aryl, or heteroaryl, each of the $C_{1-6}$ alkyl, $C_{3-10}$ cycloalkyl, $C_{1-10}$ heterocycloalkyl, aryl, and heteroaryl being optionally substituted with $C(O)OR_f$, in which $R_f$ is H, $C_{1-10}$ alkyl, $C_{3-20}$ cycloalkyl, $C_{3-20}$ heterocycloalkyl, aryl, or heteroaryl; or $R_8$ and $R_9$, together with the nitrogen atoms to which they are bonded, are $C_{3-10}$ heterocycloalkyl; $L_3$ is $C_{1-6}$ alkyl; or $L_3$, together with $R_8$ or $R_9$ and the nitrogen atom to which they are bonded, is $C_{4-10}$ heterocycloalkyl or heteroaryl; and $R_{10}$ is H, $C_{1-6}$ alkyl, $C_{1-6}$ alkoxyl, $C_{3-10}$ cycloalkyl, $C_{1-10}$ heterocycloalkyl, aryl, heteroaryl, or

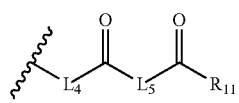

in which $L_4$ is deleted or $C_{1-6}$ alkylamino; $L_5$ is $C_{1-6}$ alkyl, $C_{1-6}$ alkylamino, or di-$C_{1-6}$ alkylamino; and $R_{11}$ is hydroxyl or $C_{1-6}$ alkylamino; each of the $C_{1-6}$ alkyl, $C_{1-6}$ alkoxyl, $C_{3-10}$ cycloalkyl, $C_{1-10}$ heterocycloalkyl, $C_{1-6}$ alkylamino; di-$C_{1-6}$ alkylamino, aryl, and heteroaryl being optionally substituted with hydroxyl, amino, $C(O)OR_{12}$, or $P(O)(OR_{13})_2$, in which each of $R_{12}$ and $R_{13}$, independently, is H or $C_{1-6}$ alkyl.

The term "alkyl" herein refers to a saturated, linear or branched hydrocarbon moiety, such as —$CH_3$ or branched —$C_3H_7$. The term "cycloalkyl" refers to a non-aromatic, monocyclic, bicyclic, tricyclic, or tetracyclic hydrocarbon moiety, such as cyclohexyl, cyclohexen-3-yl, or adamantyl. The term "alkoxyl" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "heterocycloalkyl" refers to a non-aromatic, monocyclic, bicyclic, tricyclic, or tetracyclic moiety having one or more ring heteroatoms (e.g., N, O, or S), such as 4-tetrahydropyranyl or 4-pyranyl. The term "aryl" refers to a hydrocarbon moiety having one or more aromatic rings. Examples of aryl include, but are not limited to, phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl include, but are not limited to, furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "aryl alkyl" refers to an alkyl that is substituted with at least one aryl group. Examples of aryl alkyl include benzyl (Bn) and 1-naphthylmethyl. The term "heteroaryl alkyl" refers to an alkyl that is substituted with at least one heteroaryl group. Examples of heteroaryl alkyl include 2-furanyl-methyl and 2-thienylmethyl. The term "amino alkyl" or "alkylamino" refers to an alkyl that is substituted with at least one amino group. Examples of amino alkyl or alkylamino include aminomethyl and 2-aminoethyl. The term "dialkylamino" refers to an amino group that is substituted with two alkyl groups. Examples of dialkylamino include 1,1-dimethylamino and 1-methyl-1-ethylamino. The term "amino cycloalkyl" refers to a cycloalkyl that is substituted with at least one amino group. Examples of amino cycloalkyl include amino cyclopropyl and amino cyclopentyl. The term "amino heterocycloalkyl" refers to a heterocycloalkyl that is substituted with at least one amino group. Examples of amino heterocycloalkyl include amino pyrrolidinyl and amino piperidinyl. The term "hydroxyl alkyl" refers to an alkyl that is substituted with at least one hydroxyl group. Examples of hydroxyl alkyl include hydroxyl methyl and hydroxyl ethyl.

Alkyl, cycloalkyl, heterocycloalkyl, aryl, heteroaryl, aryl alkyl, and heteroaryl alkyl mentioned herein include both substituted and unsubstituted moieties, unless specified otherwise. Possible substituents on cycloalkyl, heterocycloalkyl, aryl, and heteroaryl include $C_{1-10}$ alkyl, $C_{2-10}$ alkenyl, $C_{2-10}$ alkynyl, $C_{3-20}$ cycloalkyl, $C_{3-20}$ cycloalkenyl, $C_{1-20}$ heterocycloalkyl, $C_{1-20}$ heterocycloalkenyl, $C_{1-10}$ alkoxy, aryl, aryloxy, heteroaryl, heteroaryloxy, amino, $C_{1-10}$ alkylamino, $C_{1-20}$ dialkylamino, arylamino, diarylamino, hydroxyl, halogen, thio, $C_{1-10}$ alkylthio, arylthio, $C_{1-10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_{1-10}$ alkyl, $C_{2-10}$ alkenyl, and $C_{2-10}$ alkynyl. Cycloalkyl, heterocycloalkyl, aryl, and heteroaryl can also be fused with each other.

The heterocyclic compounds described above include the compounds themselves, as well as their salts, prodrugs, and solvates, if applicable. A salt, for example, can be formed between an anion and a positively charged group (e.g., amino) on a heterocyclic compounds. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a heterocyclic compound. Suitable cations include sodium ion, potassium ion, magnesium ion, calcium ion, and an ammonium cation such as tetramethylammonium ion. The heterocyclic compounds also include those salts containing quaternary nitrogen atoms. Examples of prodrugs include esters and other pharmaceutically acceptable derivatives, which, upon administering to a subject, are capable of providing active heterocyclic compounds. A solvate refers to a complex formed between an active heterocyclic compound and a pharmaceutically acceptable solvent. Examples of a pharmaceutically acceptable solvent include water, ethanol, isopropanol, ethyl acetate, acetic acid, and ethanolamine.

The heterocyclic compounds may contain non-aromatic double bonds, which can occur as cis- or trans-isomeric forms. Such isomeric forms are contemplated.

Another aspect of this invention is related to a method for mobilizing hematopoietic stem cells (HSC) and endothelial progenitor cells (EPC) into the peripheral circulation. The method includes contacting HSC and EPC with an effective amount of one or more of the heterocyclic compounds of Formula (I) described above.

An additional aspect of this invention relates to a method for treating tissue injury, cancer, inflammatory disease, and autoimmune disease. The method includes administering to a subject in need thereof an effective amount of one or more of the heterocyclic compounds of Formula (I) described above. Examples of tissue injury include neurodegenerative disease, retinal pigment epithelium dysfunction, heart and myocardial infarction, ischemic disease (e.g., ischemic stroke and limb ischemia), wound, bone fracture, pancreatic injury, kidney injury, intestinal injury, and lung injury. Examples of cancer include acute myeloid leukemia, non-small cell lung cancer, multiple myeloma, and pancreatic cancer. Examples of inflammatory disease include inflammatory bowel disease, allergic asthma, and ocular uveitis. An exemplary autoimmune disease is rheumatoid arthritis.

In a particular example, the method is performed to treat a kidney injury (e.g., acute kidney injury). The method includes administering to a subject suffering from kidney injury an effective amount of one or more of the heterocyclic compounds described above.

Also within the scope of this invention is a pharmaceutical composition containing one or more of the above-described heterocyclic compounds of Formula (I). The pharmaceutical composition can be used for treating tissue injury (e.g., acute kidney injury), cancer, inflammatory disease, and autoimmune disease.

This invention also features use of one or more of the above-described heterocyclic compounds of Formula (I) for the manufacture of a medicament for treating tissue injury (e.g., acute kidney injury), cancer, inflammatory disease, and autoimmune disease.

The term "treating" or "treatment" refers to administering one or more of the heterocyclic compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it. "An effective amount" refers to the amount of an active compound that is required to confer the therapeutic effect. Effective doses will vary, as recognized by those skilled in the art, depending on the types of disease treated, route of administration, excipient usage, and the possibility of co-usage with other therapeutic treatment.

To practice the method of the present invention, a composition having one or more of the above-described heterocyclic compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing any suitable preservative or absorption promoter (e.g., benzyl alcohol) or any solubilizing or dispersing agent (e.g., fluorocarbon).

A composition having one or more of the above-described heterocyclic compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Disclosed in detail below are heterocyclic compounds of Formula (I):

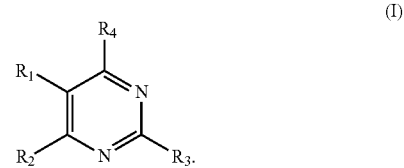

$R_1$-$R_4$ are defined in the SUMMARY section above.

One subset of the heterocyclic compounds of formula (I) includes those in which each of $R_1$ and $R_2$, independently, is H, $NH_2$, $C_{1-6}$ alkyl, or $C_{1-10}$ heterocycloalkyl (e.g., morpholine, piperidine, or piperazine) optionally substituted with $C_{1-6}$ alkyl or $C(O)OR_a$, in which $R_a$ is H or $C_{1-10}$ alkyl. Exemplary compounds in this subset include those in which each of $R_1$ and $R_2$, independently, is H or $C_{1-6}$ alkyl; and those in which each of $R_1$ and $R_2$, independently, is H, $NH_2$, or $C_{1-10}$ heterocycloalkyl optionally substituted with $C_{1-6}$ alkyl or $C(O)OR_a$.

Another subset of the heterocyclic compounds of formula (I) of this invention includes those in which $R_1$ and $R_2$, together with the two carbon atoms to which they are bonded, are aryl or heteroaryl. Exemplary compounds in this subset include those in which $R_1$ and $R_2$, together with the two carbon atoms to which they are bonded, are

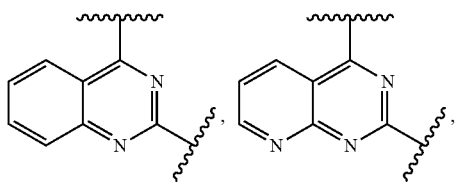

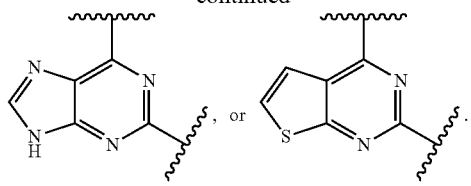

Still another subset of the heterocyclic compounds of formula (I) of this invention includes those in which each of $R_3$ and $R_4$, independently, is

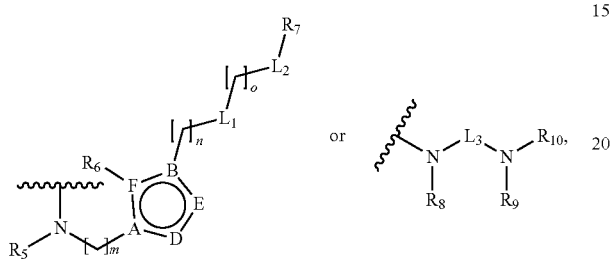

in which $R_5$ is H; $R_6$ is deleted; each of m, n, and o, independently, is 1, 2, 3, or 4; and each of $L_1$ and $L_2$ is $NR_d$. In this subset, compounds can have C as each of their A and B and have C, N, or S as each of their D, E, and F. They also can have each of $R_1$ and $R_2$, independently, being H or $C_{1-6}$ alkyl (e.g., $R_1$ being H and $R_2$ being $C_{1-6}$ alkyl); or $R_1$ and $R_2$, together with the two carbon atoms to which they are bonded, are aryl or heteroaryl. For example, this subset includes compounds having $R_1$ and $R_2$, together with the two carbon atoms to which they are bonded, being

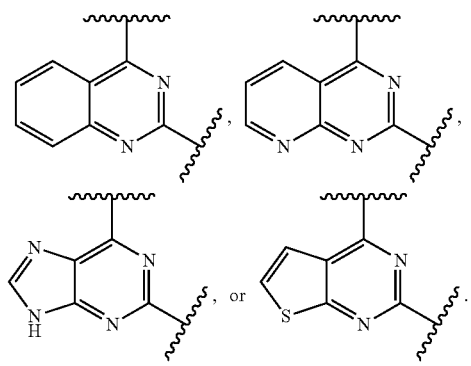

A further subset of the heterocyclic compounds of formula (I) includes those in which $R_3$ is

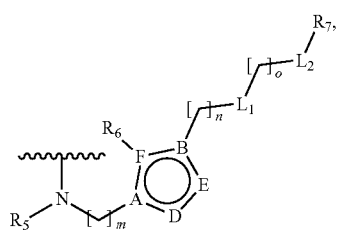

$R_4$ is

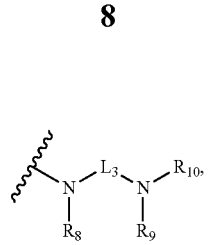

$R_5$ is H; $R_6$ is deleted; each of m, n, and o, independently, is 1, 2, 3, or 4; and each of $L_1$ and $L_2$ is $NR_d$. In this subset, compounds can have each of their $R_1$ and $R_2$, independently, as H or $C_{1-6}$ alkyl (e.g., $R_1$ being H and $R_2$ being $C_{1-6}$ alkyl); or $R_1$ and $R_2$, together with the two carbon atoms to which they are bonded, are aryl or heteroaryl. For example, this subset includes compounds having $R_1$ and $R_2$, together with the two carbon atoms to which they are bonded, being

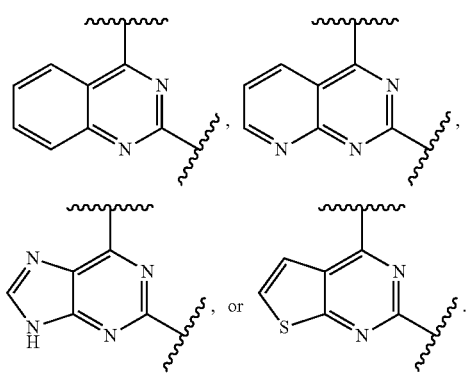

In particular, compounds can have their $R_1$ and $R_2$, together with the two carbon atoms to which they are bonded, as

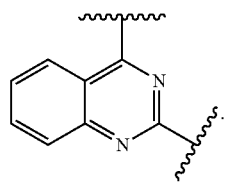 [SMILES: *c1nc(*)c2ccccc2n1]

They also can have C as each of their A and B and have C, N, or S as each of their D, E, and F. Also in this subset, compounds can have $L_3$, together with $R_8$ or $R_9$ and the nitrogen atom to which they are bonded, being $C_{4-10}$ heterocycloalkyl; and $R_{10}$ being H or

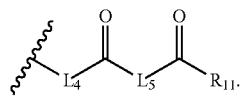

Compounds in this subset can have $R_8$ being H and $L_3$, together with $R_9$ and the nitrogen atom to which they are bonded, being $C_{4-10}$ heterocycloalkyl. An exemplary compound in this subset has $R_1$ being H and $R_2$ being $C_{1-6}$ alkyl, or $R_1$ and $R_2$, together with the two carbon atoms to which they are bonded, being

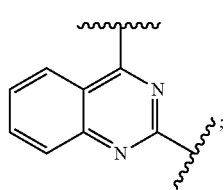 [SMILES: *c1nc(*)c2ccccc2n1]

R₁₀ being

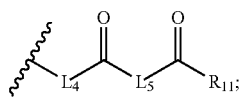

each of A and B being C; and each of D, E and F, independently, being C, N, or S.

Also within this invention is a pharmaceutical composition containing one or more of the heterocyclic compounds of Formula (I) described above for treating tissue injury (e.g., acute kidney injury), cancer, inflammatory disease, and autoimmune disease.

Further covered by this invention is a method for treating tissue injury (e.g., acute kidney injury), cancer, inflammatory disease, and autoimmune disease, the method including administering to a subject in need thereof an effective amount of a compound of Formula (I).

The heterocyclic compounds of Formula (I) described above can be prepared according to methods well known in the field. See, for example, R. Larock, Comprehensive Organic Transformations (2$^{nd}$ Ed., VCH Publishers 1999); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2$^{nd}$ ed., John Wiley and Sons 2009); and G. J. Yu et al., *J. Med. Chem.* 2008, 51, 6044-6054.

The compounds mentioned herein may contain a non-aromatic double bond and one or more asymmetric centers. Thus, they can occur as racemates or racemic mixtures, single enantiomers, individual diastereomers, diastereomeric mixtures, or cis- or trans-isomeric forms. All such isomeric forms are contemplated.

The compounds of Formula (I) thus prepared can be initially screened using in vitro assays, e.g., the radioligand binding assay described in Example 2 below, for their potency in inhibiting binding of CXCL12 to CXCR4. They can be subsequently evaluated using in vivo assays, e.g., a colony-forming assay, for their efficacy in enhancing hematopoietic stem cell mobilization in a mammal. The selected compounds can be further tested to verify their efficacy in treating tissue injury (e.g., acute kidney injury), cancer, inflammatory disease, and autoimmune disease. For example, a compound can be administered to an animal (e.g., a mouse) having ischemic acute kidney injury and its therapeutic effects are then assessed. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Shown immediately below are the structures of 86 exemplary compounds of Formula (I). The methods for preparing these compounds, as well as the analytical data for the compounds thus prepared, are set forth in EXAMPLE 1 below. The procedures for testing these compounds are described in EXAMPLES 2-5 also below.

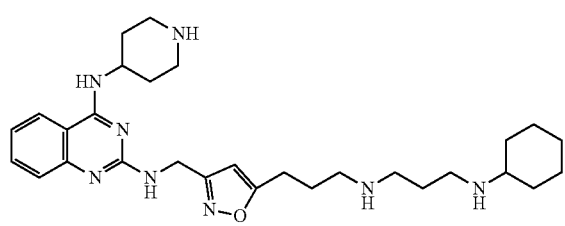

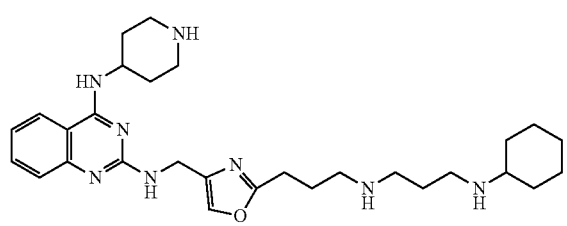

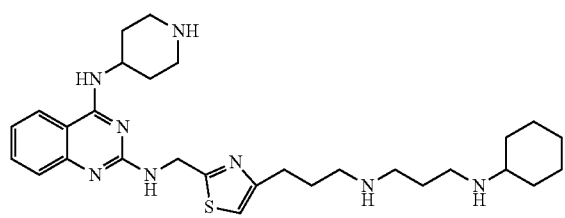

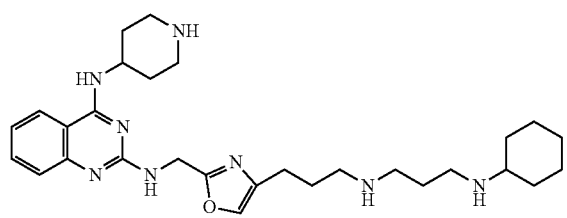

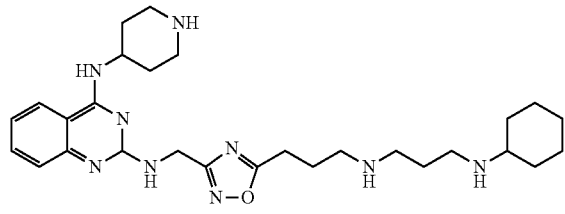

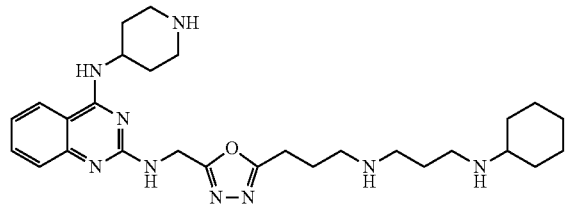

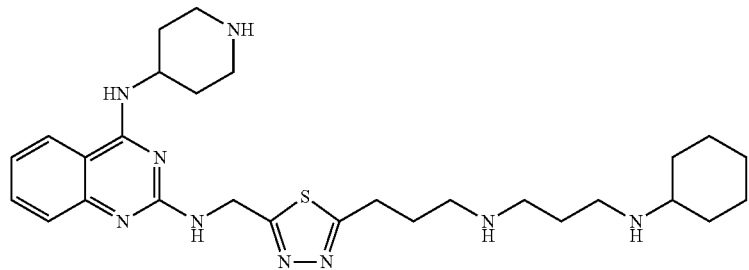
7
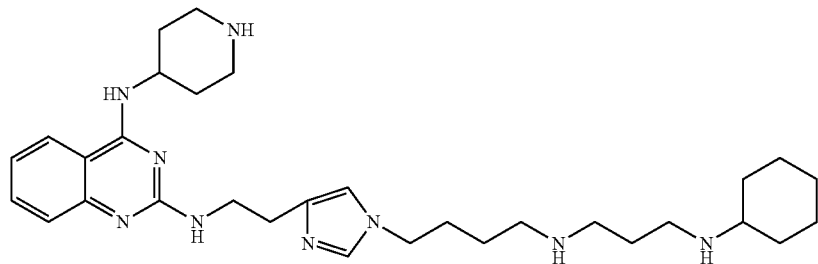
8
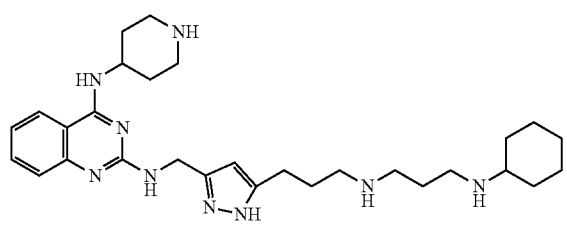
9
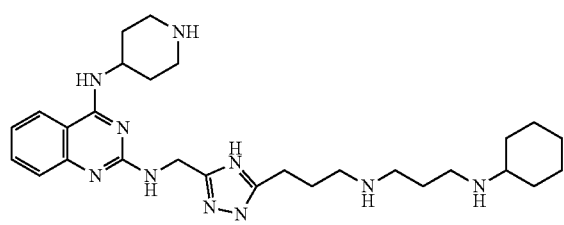
10
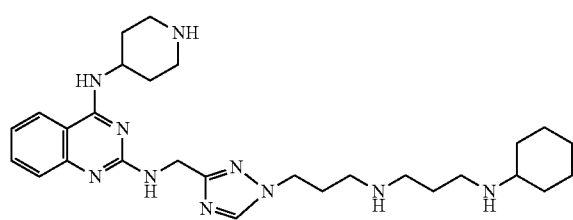
11
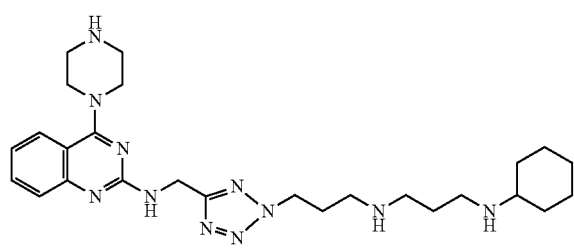
12
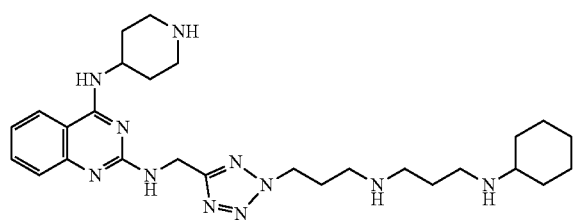
13
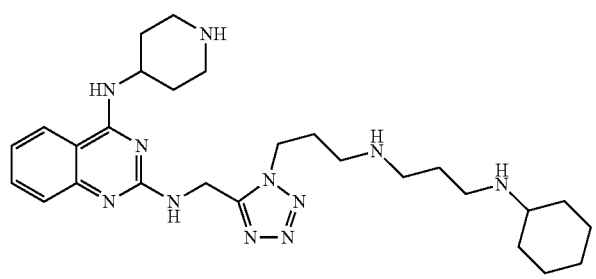
14
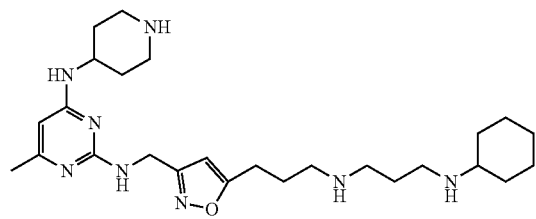
15
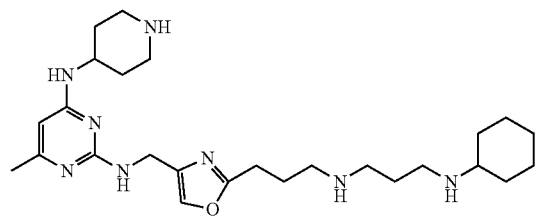
16

-continued
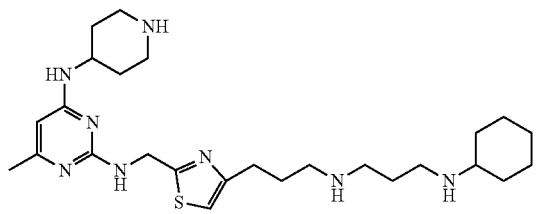
17
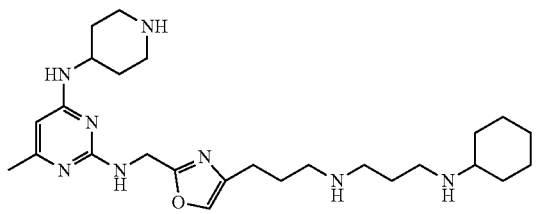
18
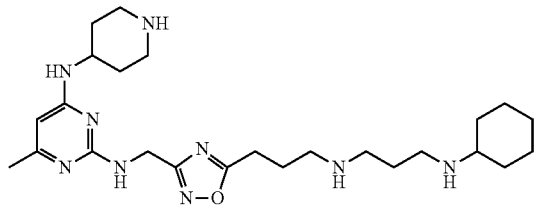
19
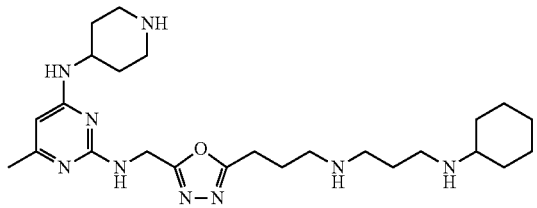
20
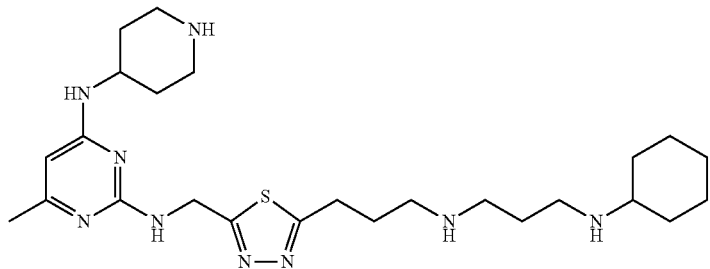
21
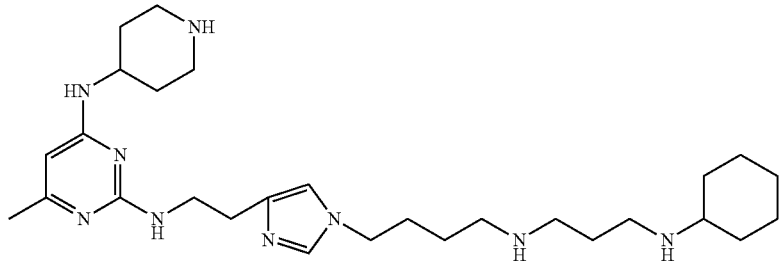
22
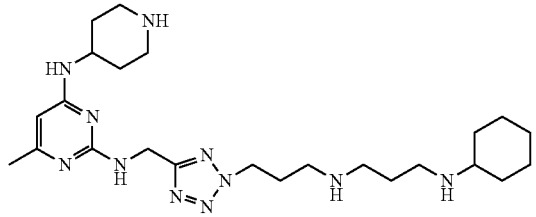
23
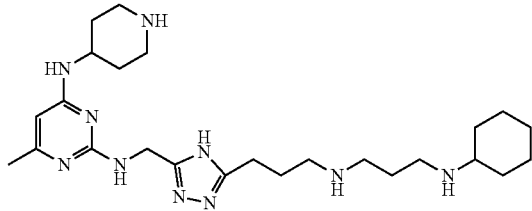
24
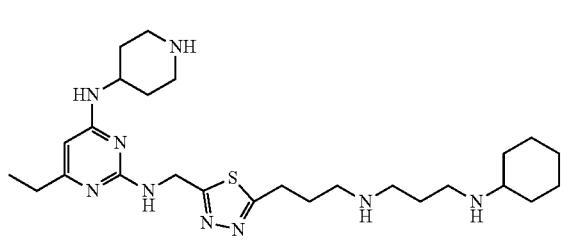
25
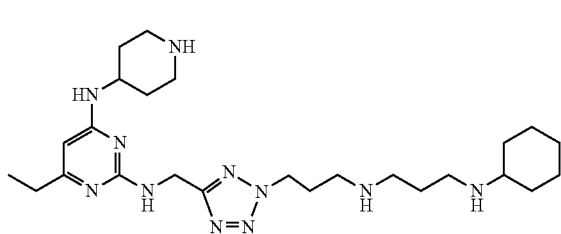
26

-continued
27
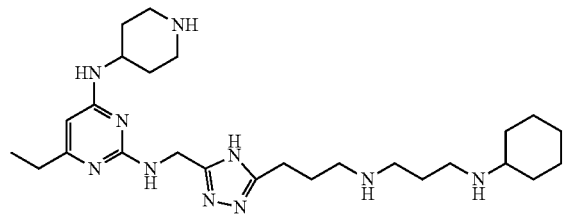
28
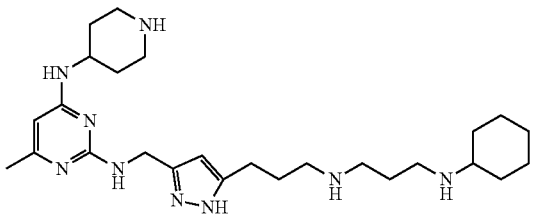
29
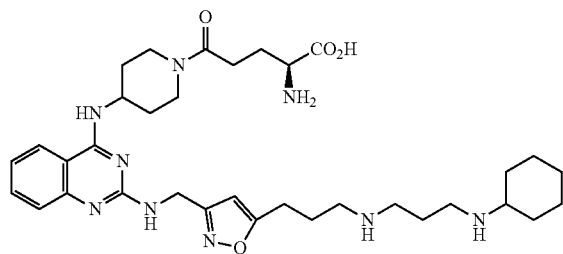
30
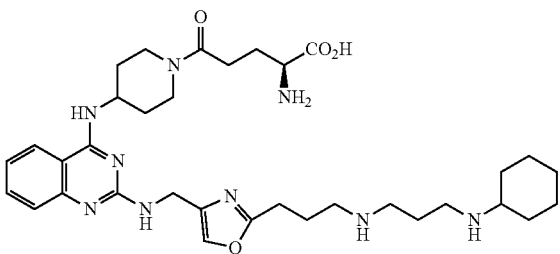
31
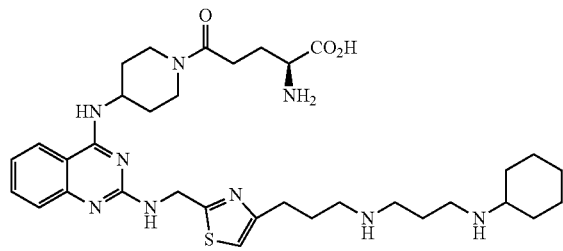
32
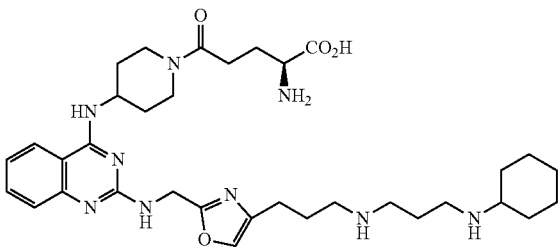
33
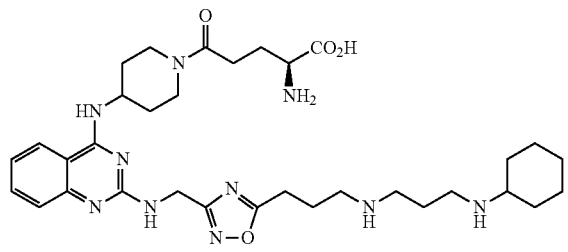
34
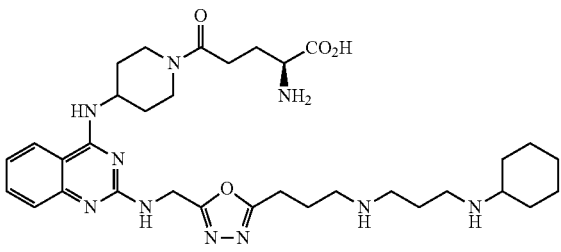
35
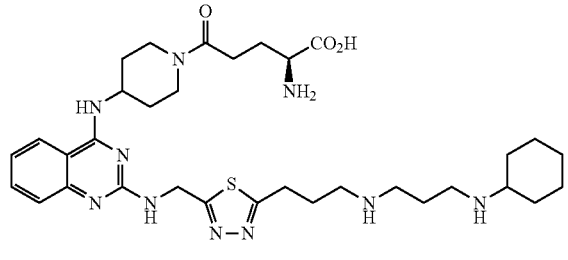
36
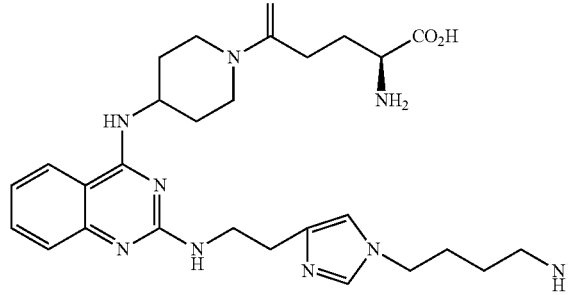

37
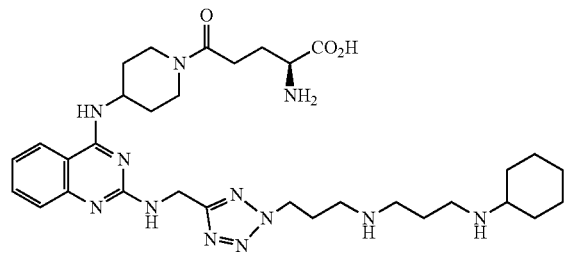
38
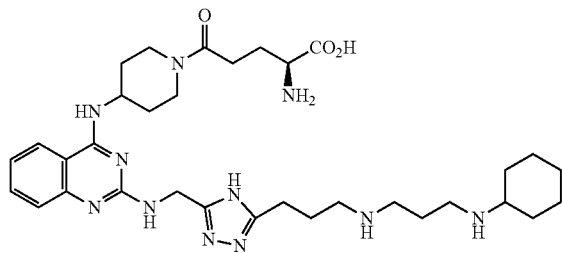
39
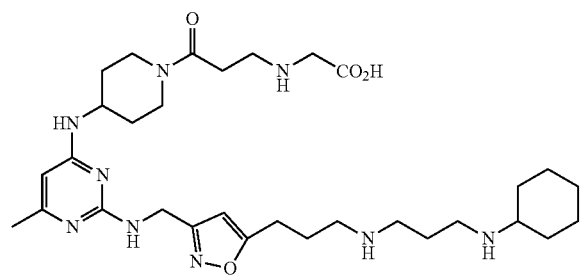
40
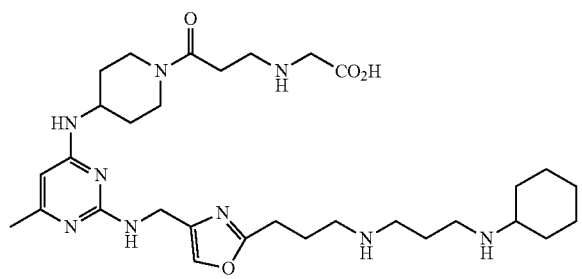
41
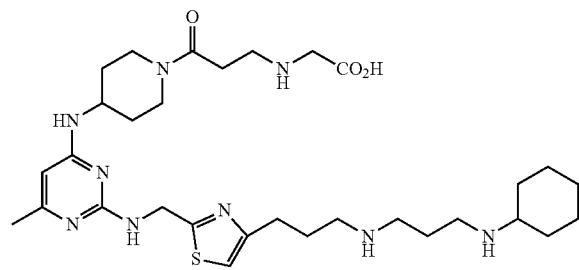
42
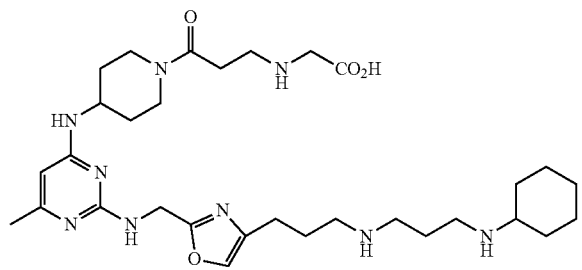
43
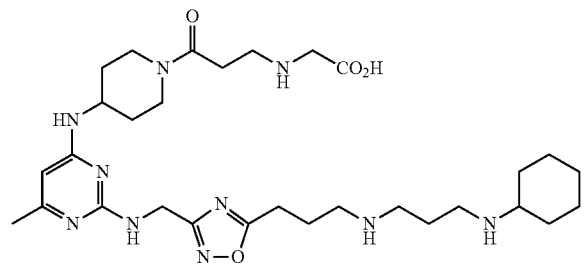
44
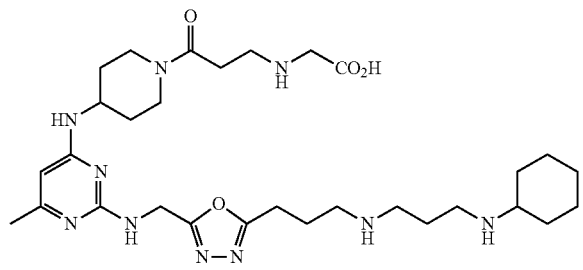
45
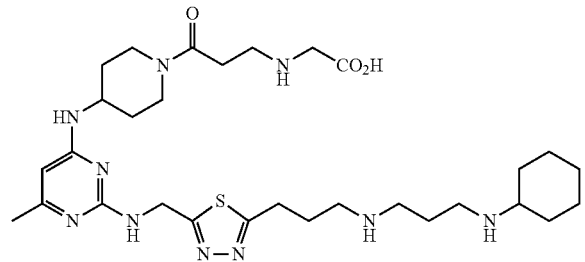
46
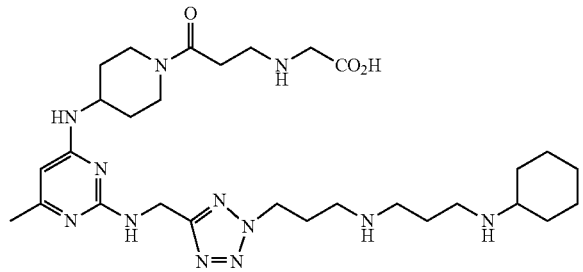

-continued
47
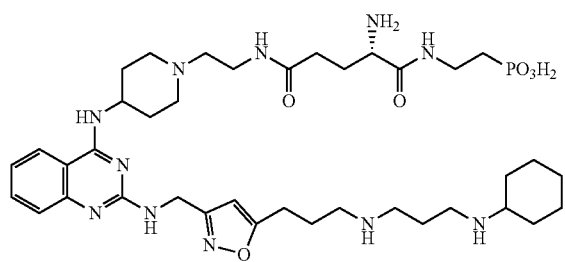
48
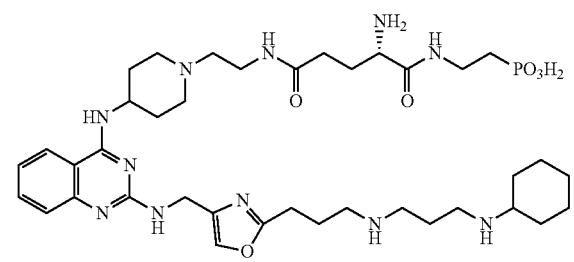
49
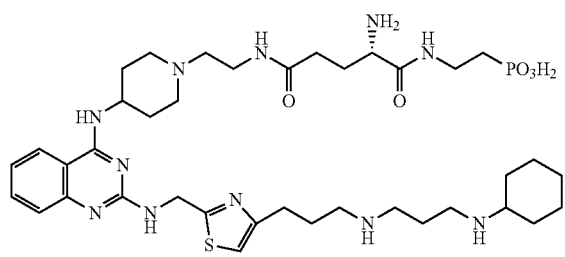
50
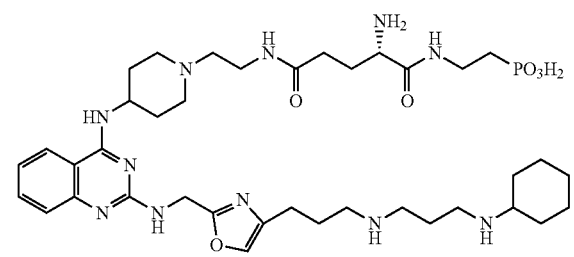
51
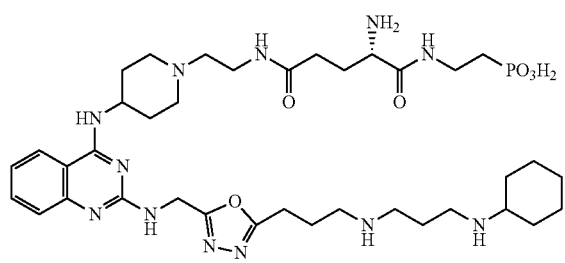
52
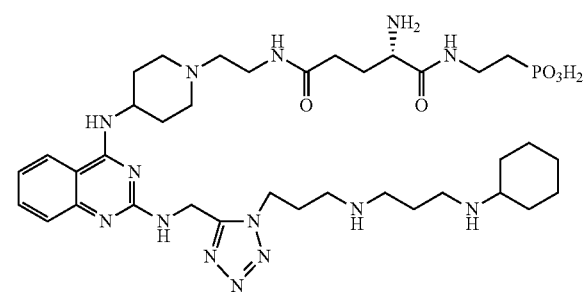
53
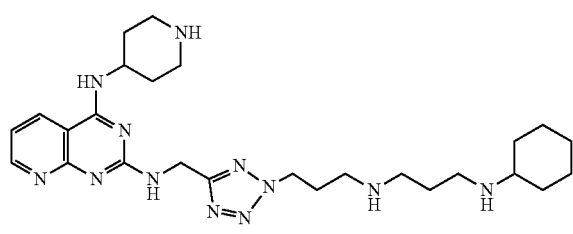
54
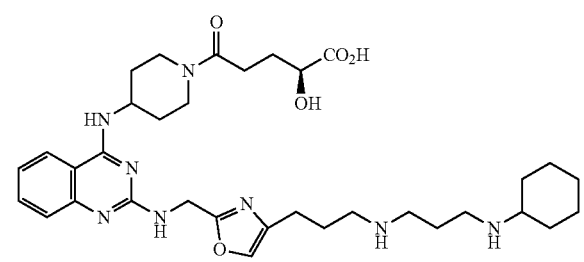
55
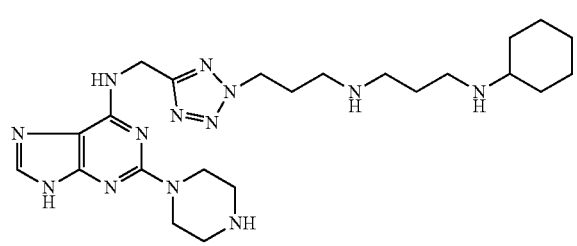
56
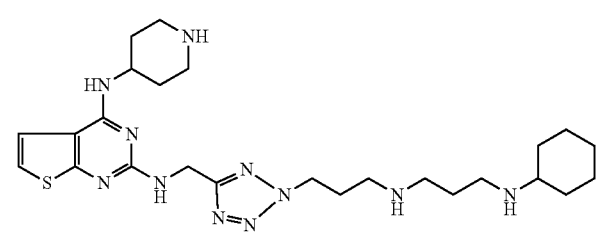

-continued
57
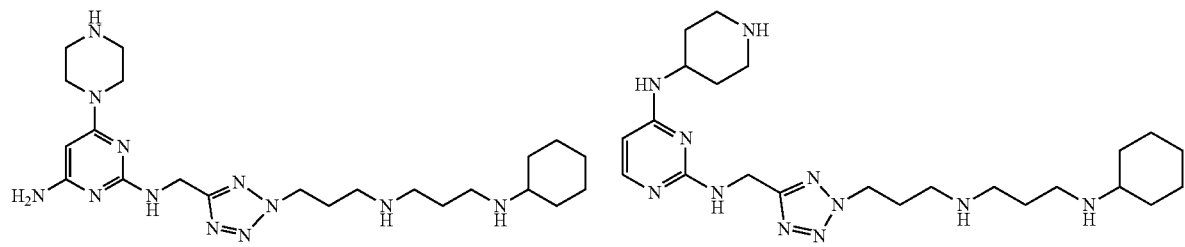
58
59
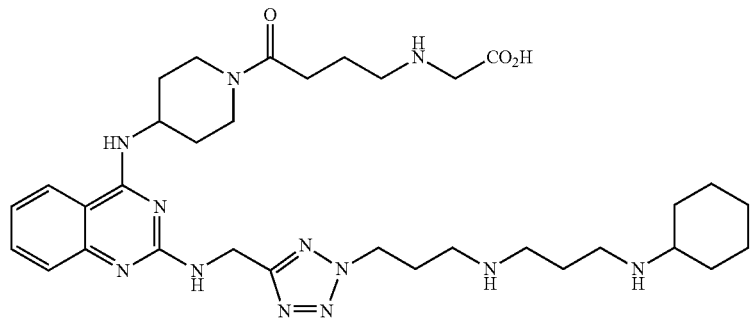
60
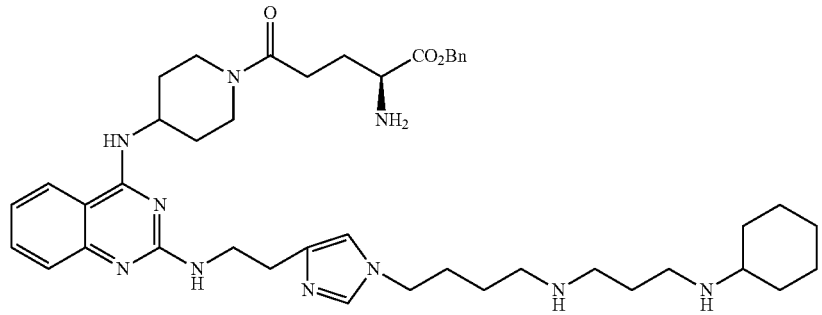
61
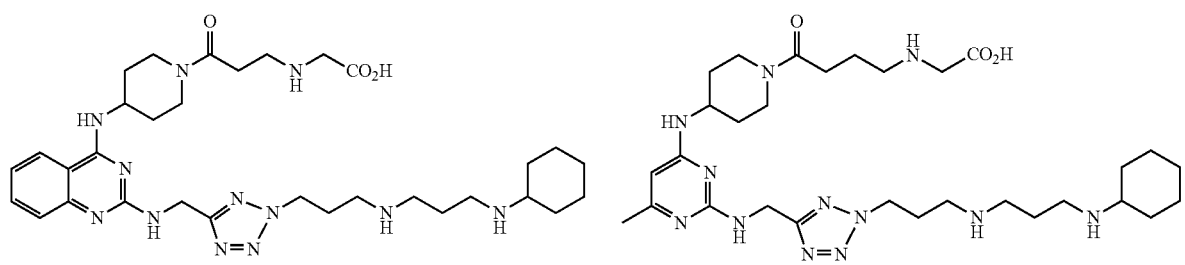
62
63
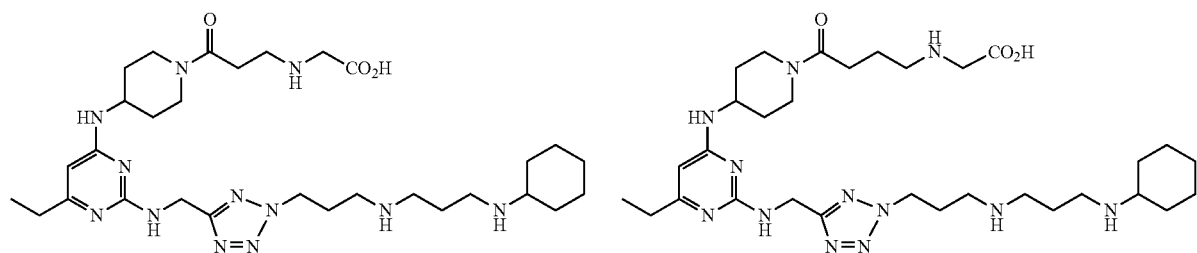
64

-continued
65
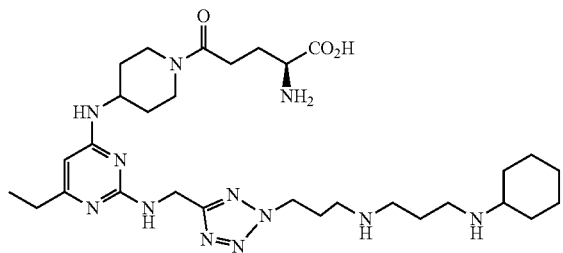
67
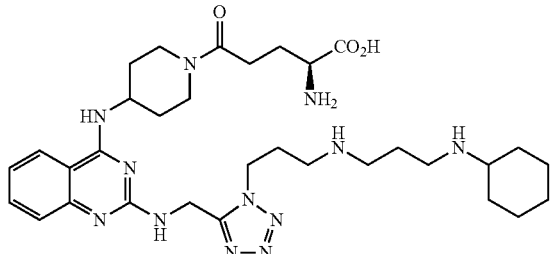
69
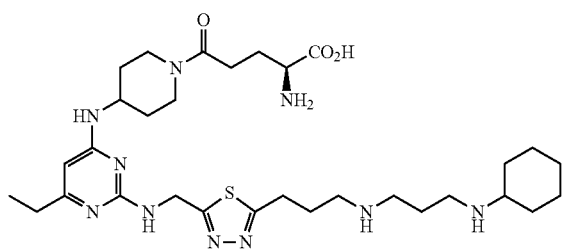
71
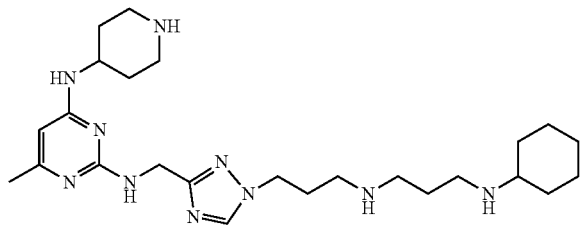
73
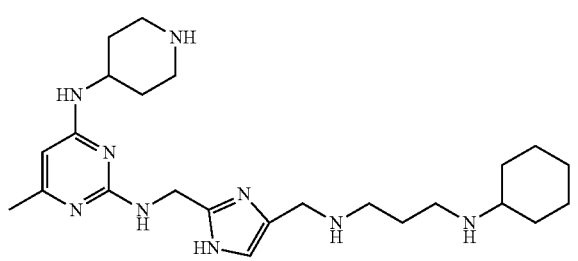
75
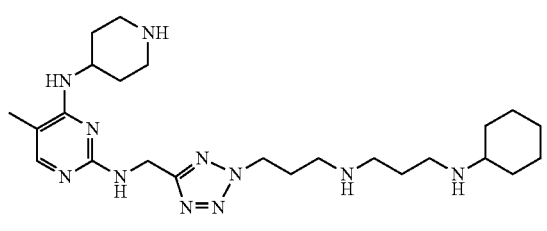
66
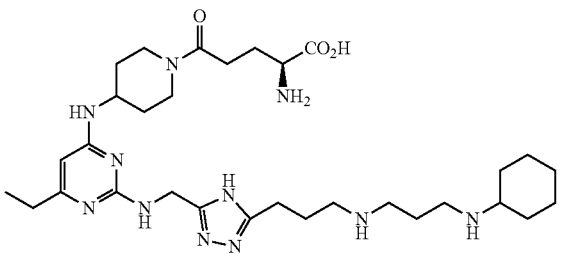
68
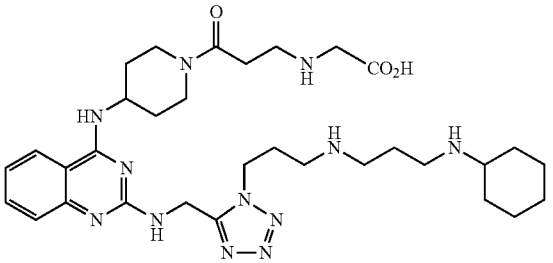
70
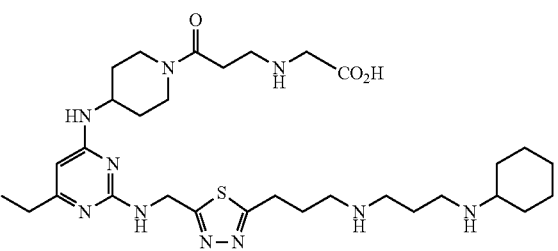
72
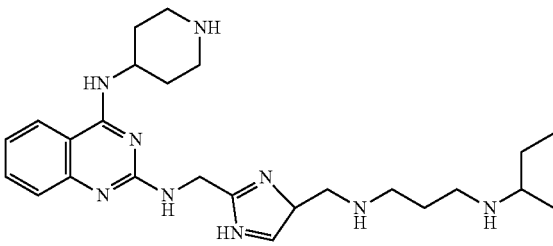
74
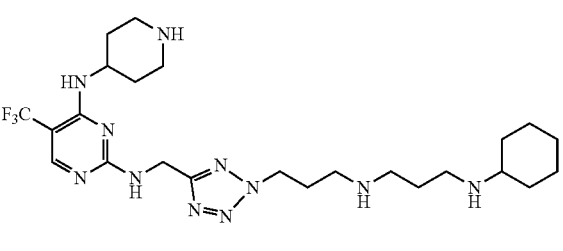
76
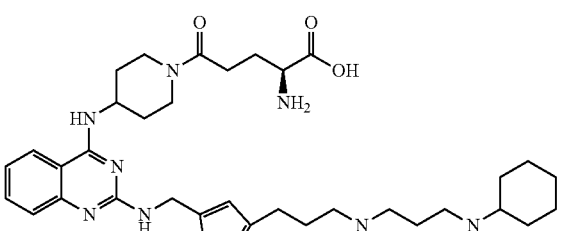

-continued
77
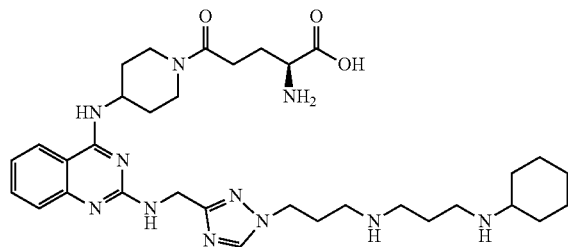
78
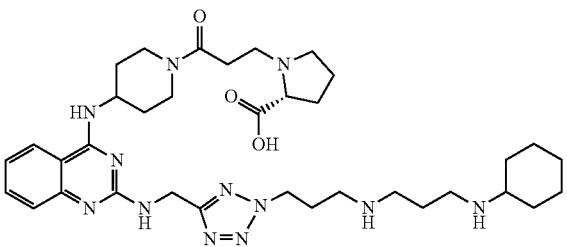
79
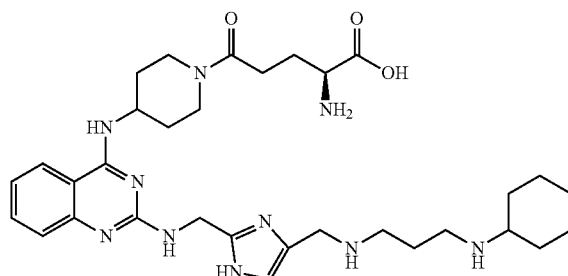
80
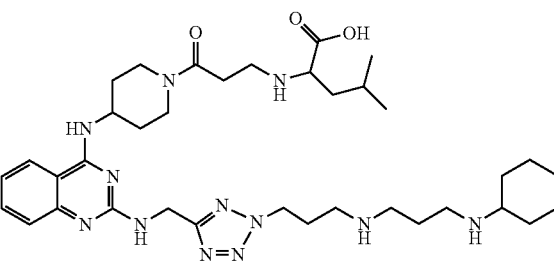
81
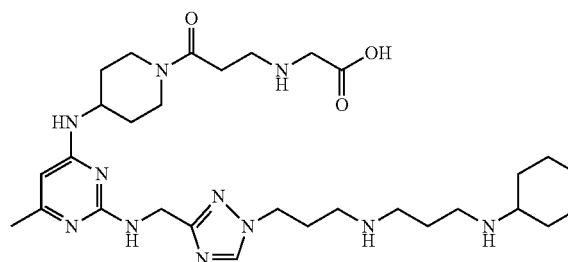
82
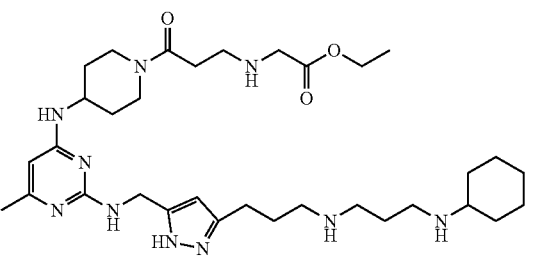
83
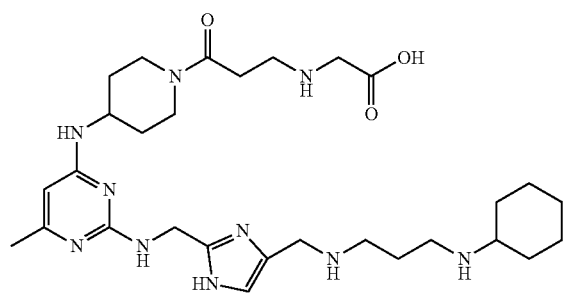
84
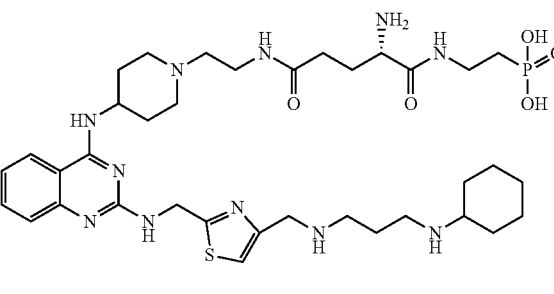
85
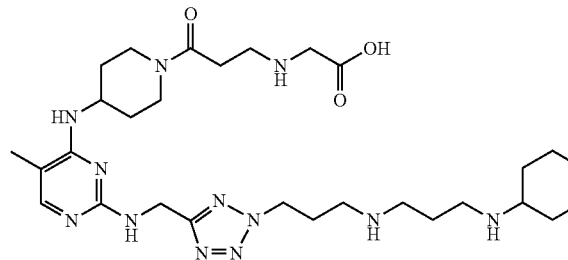
86
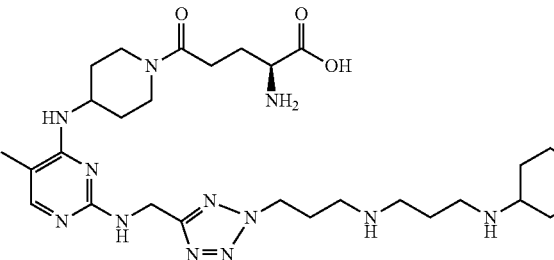

Described below are the procedures for preparing thirteen side chains, i.e., side chains S-I-S-XIII, used to synthesize the above 86 exemplary compounds. Note that all the side chains were prepared in different manners. The structures of side chain compounds S-I-S-XIII are shown below:

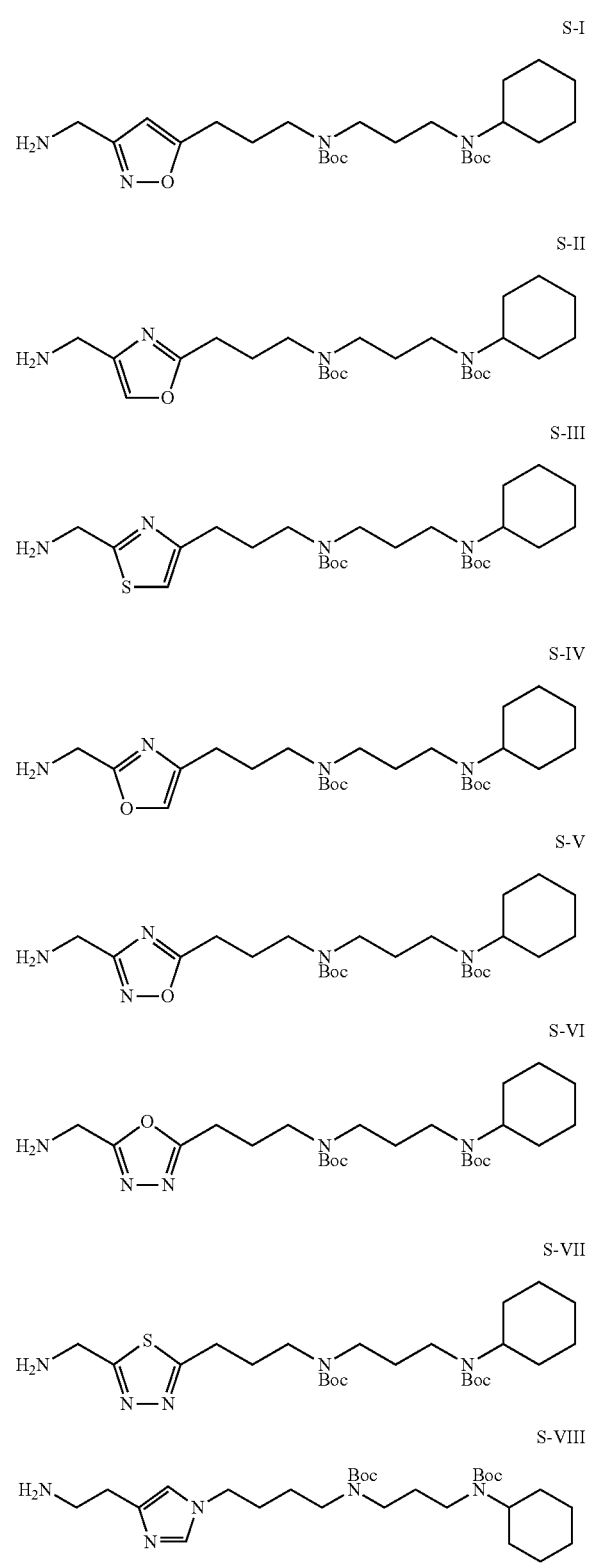

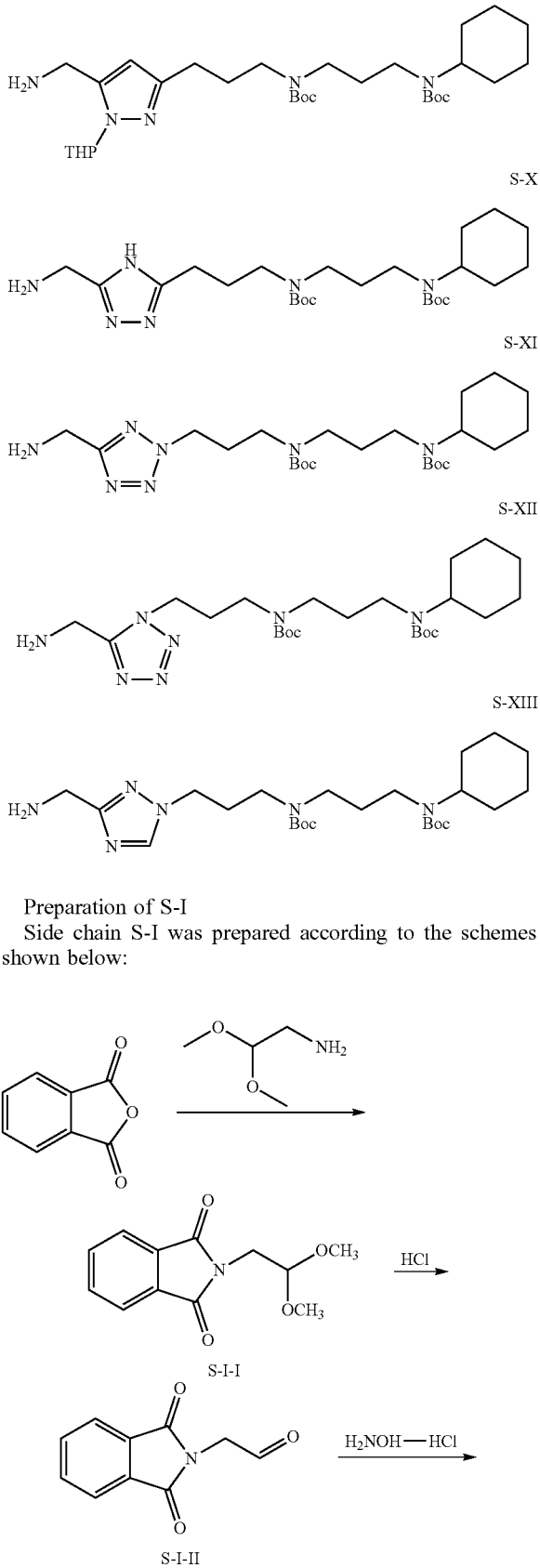

Preparation of S-I

Side chain S-I was prepared according to the schemes shown below:

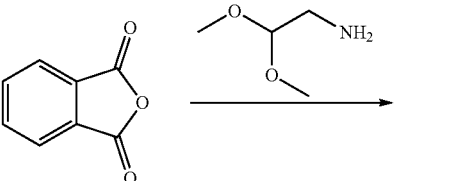

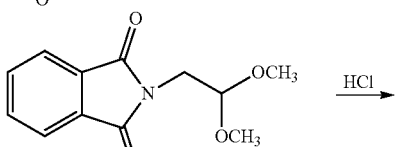

S-I-I

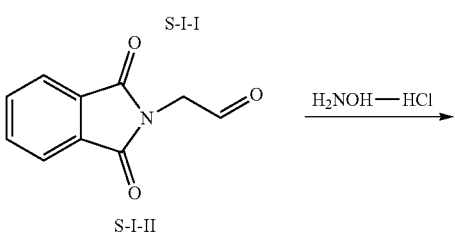

S-I-II

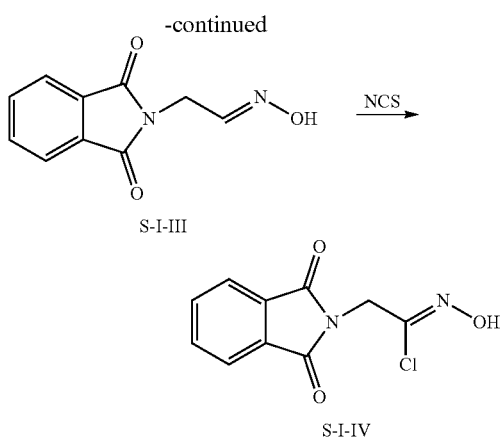

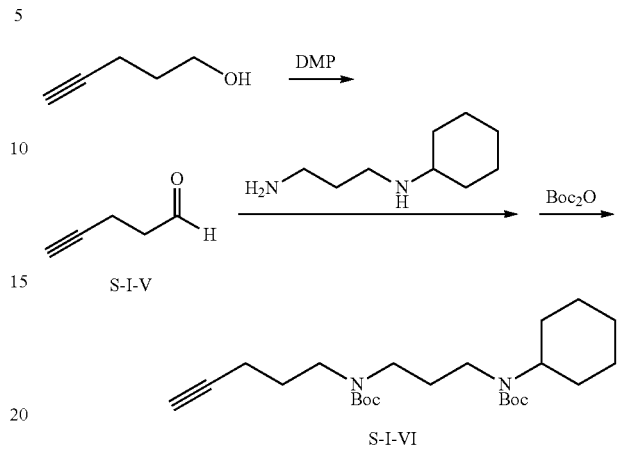

A solution of phthalic anhydride (10.00 g), aminoacetaldehyde (7.81 g) and N,N-diisopropylethylamine (13.09 g) in toluene under an atmosphere of nitrogen was heated at 120° C. for 16 h and then quenched with NH₄Cl (aq) (100 mL, 2 M). The aqueous phase was extracted with ethyl acetate (3×50 mL). The combined organic extracts were washed with water and brine, dried over anhydrous sodium sulfate, filtered. The filtrate was concentrated to get the crude residue S-I-I (15.49 g, y: 98%).

To a solution of S-I-I (15.49 g) in EtOH/H₂O (20 mL/40 mL) was added HCl(aq) (120 mL, 6 N) under an atmosphere of nitrogen. The mixture was heated at 80° C. for 16 h and then concentrated. The residue was extracted with ethyl acetate (3×50 mL). The combined organic extracts were washed with NaHCO₃(aq) and brine, dried over anhydrous sodium sulfate, filtered. The filtrate was concentrated to get the crude residue S-I-II (6.26 g, y: 50%).

To a solution of S-I-II (6.26 g) and TEA (10.04 g) in dichloromethane (100 mL) at 5-10° C. was added hydroxylamine hydrochloride (2.53 g). The mixture was stirred at room temperature for 15 h and then quenched with NH₄Cl (aq) (50 mL, 2M). The aqueous phase was extracted with CH₂Cl₂ (2×50 mL). The combined organic extracts were washed with NaHCO₃(aq) and brine, dried over anhydrous sodium sulfate, filtered. The filtrate was concentrated to get the crude product S-I-III (4.01 g, y: 59%).

A solution of S-I-III (4.01 g) and N-chlorosuccinimide (2.75 g) in DMF (100 mL) was heated at 50° C. for 5 h and then poured into water. The resulting mixture was extracted with ethyl acetate (3×100 mL). The combined organic extracts were washed with water and brine, dried over anhydrous sodium sulfate, filtered. The filtrate was concentrated to get the crude product S-I-IV (3.64 g, y: 78%).

To a solution of 4-pentyn-1-ol (0.30 g) in dichloromethane (20 mL) at 0° C. was added Dess-Martin periodinane (1.66 g) under an atmosphere of nitrogen. The mixture was stirred at 0° C. for 2 h and then quenched with NaHCO₃(aq) (50 mL, 2 M) and sodium thiosulfate Na₂S₂O₃(aq) (50 mL, 2 M). The aqueous phase was extracted with dichloromethane (3×50 mL). The combined organic extracts were washed with brine, dried over anhydrous sodium sulfate, filtered. The filtrate was concentrated to get the crude S-I-V (0.26 g, y: 87%).

To a magnetically stirred solution of S-I-V (0.26 g) in MeOH (30 mL) was added N-cyclohexyl-1,3-propanediamine (0.54 g). After the mixture was stirred at 25° C. for 1 h, NaBH₄ (0.24 g) was added to the mixture slowly. The resulting mixture was stirred for another 15 h and then quenched with NH₄Cl(aq) (50 mL, 2M). The mixture was concentrated. The residue was extracted with CH₂Cl₂ (2×150 mL). The combined organic extracts were washed with brine, dried over anhydrous sodium sulfate, and filtered. To a magnetically stirred filtrate was added Boc₂O anhydride (0.84 g) in one portion. The mixture was stirred at room temperature for 15 h and then concentrated. The residue was purified by flash column chromatography over silica gel with n-hexane/ethyl acetate (2:1) to afford the product S-I-VI (0.48 g, y: 36% over 2 steps).

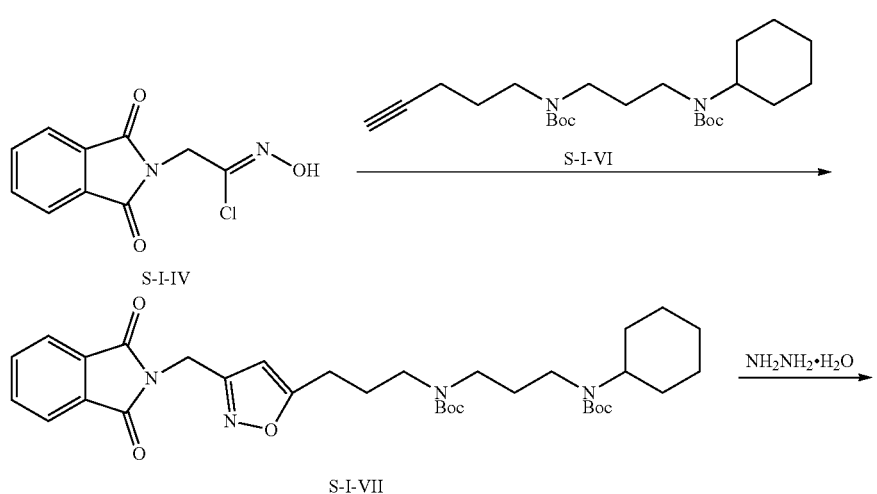

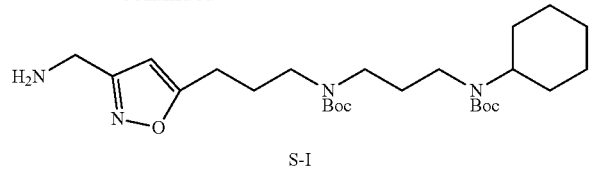

S-I

A solution of S-I-IV (0.27 g), S-I-VI (0.48 g), and triethylamine (0.34 g) in chloroform (30 mL) under an atmosphere of nitrogen was stirred at 25° C. for 15 h and then quenched with NH₄Cl(aq) (50 mL, 2 M). The aqueous phase was extracted with CH₂Cl₂ (3×50 mL). The combined organic extracts were washed with brine, dried over anhydrous sodium sulfate, filtered, and concentrated. The residue thus obtained was purified by flash chromatography on silica gel with n-hexane/ethyl acetate (4:1) to afford compound S-I-VII (0.09 g, y: 13%).

A solution of S-I-VII (0.09 g) and hydrazine monohydrate (0.02 g) in MeOH/CH₂Cl₂ (20 mL/20 mL) was stirred at 25° C. for 15 h and then filtrated. The filtrate was concentrated to get the crude product S-I (0.07 g, y: 98%).

Preparation of S-II

Side chain S-II was prepared according to the scheme shown below:

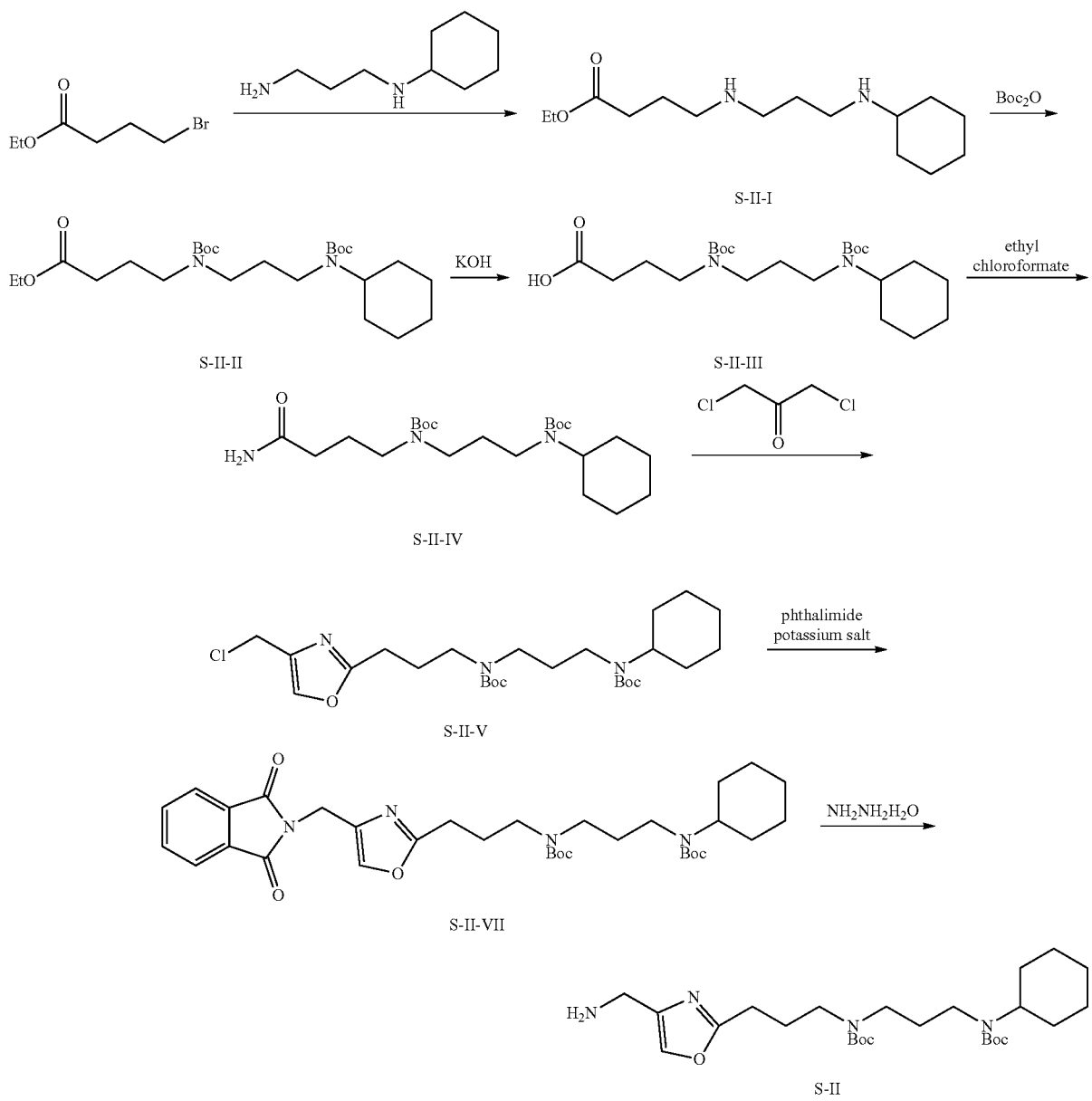

To a solution of N-cyclohexyl-1,3-propanediamine (4.22 g) and K$_2$CO$_3$ (7.09 g) in acetonitrile (100 mL) at 0° C. was added ethyl 4-bromobutyrate (5.00 g). The mixture was stirred at 25° C. for 15 h and then poured into water. The resulting mixture was extracted with ethyl acetate (3×100 mL). The combined organic extracts were washed with brine, dried over anhydrous sodium sulfate, and filtered. To a magnetically stirred filtrate of S-II-I was added Boc$_2$O anhydride (11.11 g) in one portion. The mixture was stirred at room temperature for 15 h and then concentrated. The residue thus obtained was purified by flash column chromatography on silica gel with n-hexane/ethyl acetate (4:1) to afford product S-II-II (3.60 g, y: 30% over 2 steps).

To a solution of S-II-II (3.60 g) in THF (30 mL) under an atmosphere of nitrogen was added a solution of KOH (2.14 g) in H$_2$O (10 mL). The mixture was stirred at 25° C. for 15 h and then acidified with HCl(aq) (38 mL, 1 N). The aqueous phase was extracted with ethyl acetate (3×50 mL). The combined organic extracts were washed with water and brine, dried over anhydrous sodium sulfate, filtered. The filtrate was concentrated to get the crude residue S-II-III (3.36 g, y: 99%).

To a solution of S-II-III (3.36 g) and TEA (1.16 g) in THF (30 mL) was added ethyl chloroformate (1.00 g) at 0° C. After the mixture was stirred at 0° C. for 5 h, NH$_4$OH(aq) (50 mL, 2M) was added to the mixture at 0° C. slowly and then stirred at 25° C. for another 15 h. The resulting mixture was extracted with ethyl acetate (2×50 mL). The combined organic extracts were washed with water and brine, dried over anhydrous sodium sulfate, and filtered. The filtrate was concentrated to afford crude S-II-IV (2.94 g, y: 88%).

A solution of S-II-IV (2.94 g) and 1,3-dichloroacetone (1.10 g) in isopropyl alcohol (25 mL) was heated at 100° C. for 15 h and then concentrated. The residue thus obtained was purified by flash column chromatography over silica gel with n-hexane/ethyl acetate (4:1) to afford compound S-II-V (0.70 g, y: 20%).

A solution of S-II-V (0.70 g) and phthalimide potassium salt (1.27 g) in DMF (20 mL) was stirred at 25° C. for 15 h and then poured into water. The resulting mixture was extracted with ethyl acetate (2×50 mL). The combined organic extracts were washed with water and brine, dried over anhydrous sodium sulfate, filtered, and concentrated. The residue thus obtained was purified by flash chromatography on silica gel with n-hexane/ethyl acetate (4:1) to afford S-II-VI (0.28 g, y: 33%).

A solution of S-II-VI (0.28 g) and hydrazine monohydrate (0.04 g) in MeOH/CH$_2$Cl$_2$ (20 mL/20 mL) was heated at 25° C. for 15 h and then poured into water. The resulting mixture was extracted with ethyl acetate (3×50 mL). The combined organic extracts were washed with water and brine, dried over anhydrous sodium sulfate, filtered, and concentrated. The filtrate was concentrated to get the crude product S-II (0.19 g, y: 86%).

Preparation of S-III

Side chain S-III was prepared according to the scheme shown below:

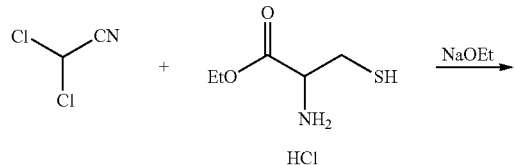

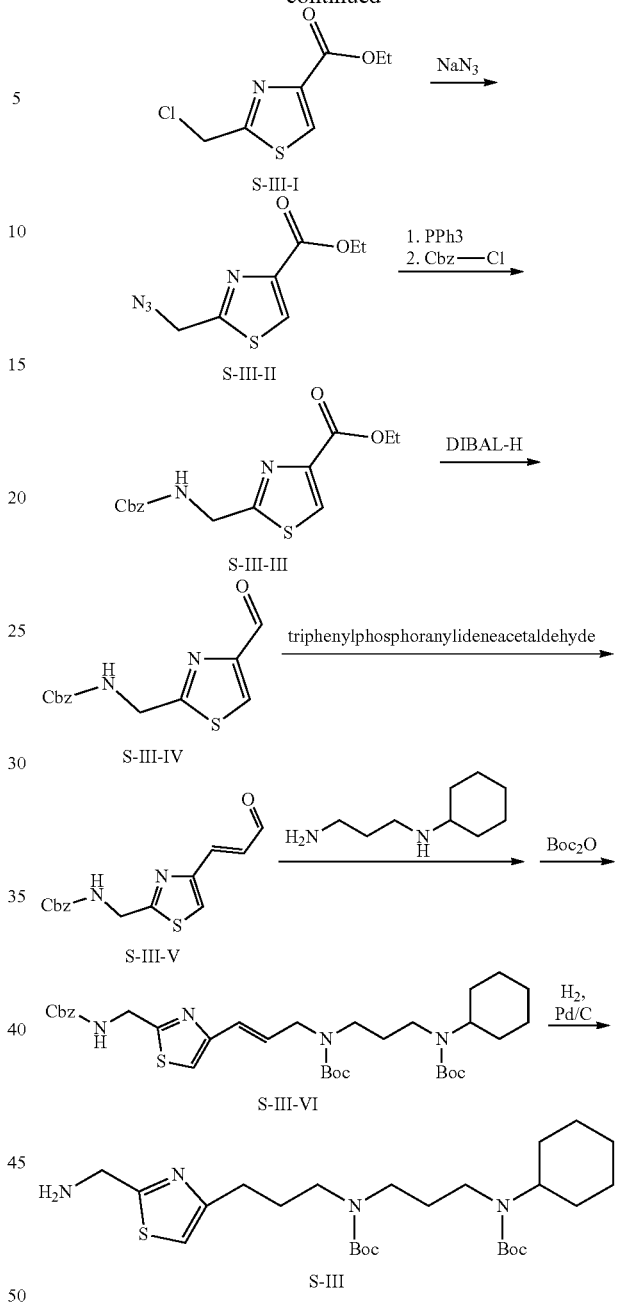

To a magnetically stirred solution of sodium ethoxide (1.0 mL, 4.4 M in EtOH) in DCM (300 mL) and EtOH (35 mL) at 0° C. was added dichloroacetonitrile (50.1 g) over 45 min. After the mixture stirred at 0° C. for 1 h, L-cysteine ethyl ester hydrochloride (84.51 g) was added to the resulting mixture. The reaction mixture was stirred at 25° C. for 15 h and then quenched with water (50 mL). The resulting mixture was concentrated and then the residue was extracted with dichloromethane (3×50 mL). The extracts were washed with water and brine, dried over anhydrous sodium sulfate, filtered, and concentrated. A solution of residue and DIPEA (119 mL) in DCM (500 mL) was stirred at 50° C. for 15 h and then quenched with NH$_4$Cl(aq) (500 mL, 2M). The separated aqueous phase was extracted with DCM (2×100 mL). The combined organic extracts were washed with water and brine, dried over anhydrous sodium sulfate, and filtered. The filtrate was then concentrated to afford crude S-III-I (93.62 g, y: 100%).

A solution of the S-III-I (93.62 g) and sodium azide (148.12 g) in DMF (500 mL) was stirred at 25° C. for 15 h and then quenched with NH$_4$Cl(aq) (50 mL, 2M). The resulting solution was extracted with Et$_2$O (3×50 mL). The combined extracts were washed with water and brine, dried over anhydrous sodium sulfate, and filtered. The filtrate was then concentrated to afford crude S-III-II (77.11 g, y: 80%).

A mixture of S-III-II (77.11 g), triphenylphosphine (96.02 g), and water (20 mL) in THF (1820 mL) was stirred at 25° C. for 15 h. The resulting mixture was extracted with ethyl acetate (3×500 mL). The extracts were washed with water and brine, dried over anhydrous sodium sulfate, filtered, and concentrated. The residue was purified by flash column chromatography over silica gel with MeOH/NH$_4$OH(aq) (9:1) to afford the amino product. To a mixture of amino product in dichloromethane (1000 mL) and NaHCO$_3$(aq) (400 mL, 2N) at 5-10° C. was added benzyl chloroformate (49.13 g). The mixture was stirred at room temperature for 15 h and then quenched with aqueous NH$_4$Cl(aq) (400 mL, 2 M). The aqueous phase was extracted with dichloromethane (3×400 mL). The extracts were washed with water and brine, dried over anhydrous sodium sulfate, filtered, and concentrated. The residue was purified by flash column chromatography over silica gel with n-hexane/ethyl acetate (3:1) to afford the product S-III-III (74.35 g, y: 64% over 2 steps).

To a solution of S-III-III (7.02 g) in dry CH$_2$Cl$_2$ (100 mL) was added DIBAL-H (28.5 mL, 1.0 M in toluene) at −78° C. The mixture was stirred at −78° C. for 2 h and then quenched with methanol (15 mL) at −78° C. HCl(aq) (80 mL, 1N) was added to the mixture and the mixture was stirred at 0° C. for 1 h. The separated aqueous layer was extracted with dichloromethane (2×100 mL). The combined organic extracts were washed with brine, dried over anhydrous sodium sulfate, and filtered. The filtrate was then concentrated to afford crude S-III-IV. A suspension of the S-III-IV and triphenylphosphoranylideneacetaldehyde (4.38 g) in toluene (100 mL) was heated at 80° C. for 5 h and then poured into water (100 mL). The aqueous phase was extracted with ethyl acetate (3×100 mL). The combined organic extracts were washed with brine, dried over anhydrous sodium sulfate, and filtered. The filtrate was then concentrated to afford crude S-III-V (5.28 g, y: 80% over two steps).

A mixture of S-III-V (6.02 g), N-cyclohexyl-1,3-propanediamine (3.12 g), and MgSO$_4$ (4.82 g) in CH$_2$Cl$_2$ (50 mL) was stirred at 25° C. for 2 h and then filtrated and concentrated. To a solution of residue in MeOH (40 mL) at 5-10° C. was added NaBH$_4$ (1.11 g). The mixture was stirred vigorously at 25° C. for 1 h and then poured into H$_2$O. The resulting mixture was concentrated and then the residue was extracted with CH$_2$Cl$_2$ (2×150 mL). The combined organic extracts were washed with brine, dried over anhydrous sodium sulfate, and filtered. To the filtrate was added Boc$_2$O anhydride (8.72 g) and TEA (5 mL) in one portion. The mixture was stirred at room temperature for 2 h and then concentrated. The residue was purified by flash column chromatography over silica gel with n-hexane/ethyl acetate (3:1) to afford the product S-III-VI (7.72 g, y: 60% over 2 steps).

A solution of S-III-VI (7.72 g) and Pd/C (0.77 g) in ethanol (200 mL) was stirred under H$_2$(g) at 25° C. for 5 h. The resulting mixture was filtered and then concentrated to give the product S-III (5.51 g, y: 90%)

Preparation of S-IV

Side chain S-IV was prepared according to the scheme shown below in a manner similar to that used to prepare S-III.

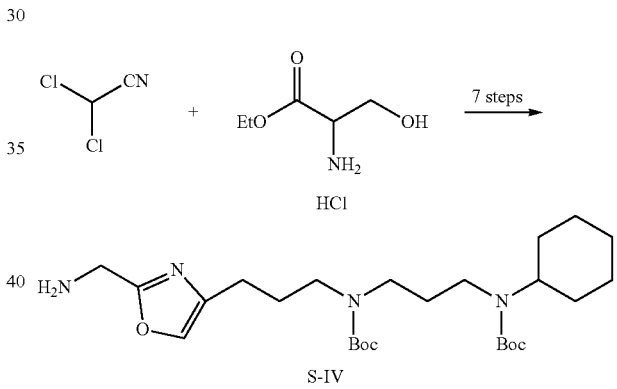

Preparation of S-V

Side chain S-V was prepared according to the schemes shown below:

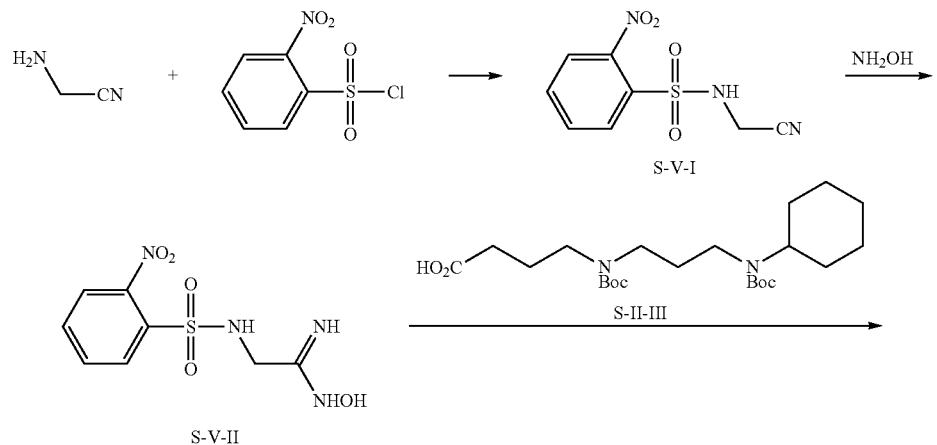

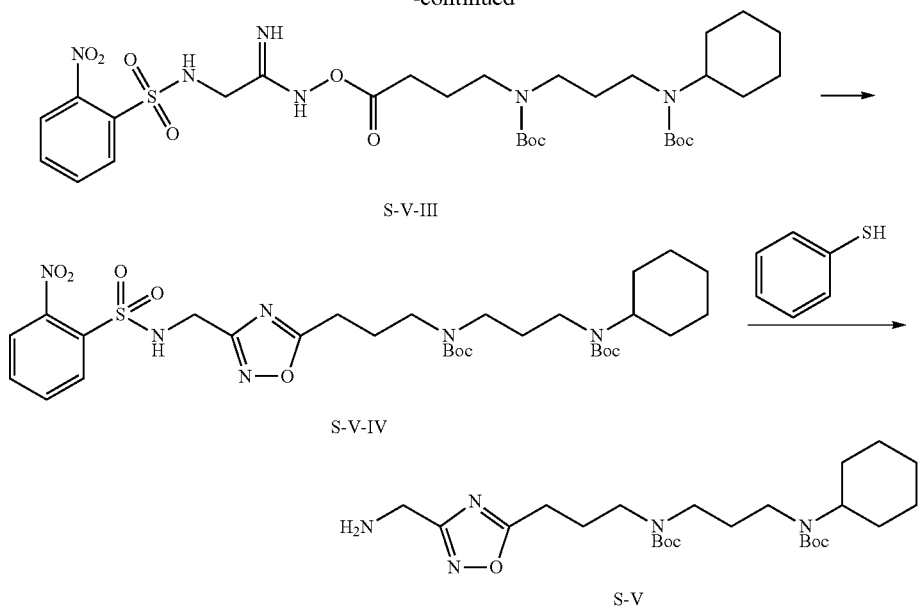

S-V-III

S-V-IV

S-V

To a solution of aminoacetonitrile hydrochloride salt (5.02 g) and TEA (16.38 g) in EtOH (100 mL) at 5-10° C. was added a solution of 2-nitrobenene sulfonyl chloride (11.43 g) in dry THF (20 mL) dropwise over 5 min. The mixture was stirred at 25° C. for 15 h and then concentrated. The residue was poured into water and the mixture was extracted with ethyl acetate (3×100 mL). The combined organic extracts were washed with brine, dried over anhydrous sodium sulfate, filtered. The filtrate was concentrated to afford crude S-V-I (9.43 g, y: 72%).

A solution of S-V-I (4.49 g) and NH₂OH (5.02 g, 50% in H₂O w/w) in MeOH (50 ml) was heated at 40° C. for 1 h and then concentrated. The resulting mixture was extracted with ethyl acetate (3×100 mL). The combined organic extracts were washed with brine, dried over anhydrous sodium sulfate, and filtered. The filtrate was concentrated to afford crude S-V-II (4.14 g, y: 81%)

A solution of S-V-II (10.02 g), S-II-III (24.32 g), EDCI (10.50 g), and DMAP (6.71 g) in dry THF (120 mL) was stirred at 25° C. for 6 h and then poured into water. The resulting mixture was extracted with ethyl acetate (3×120 mL). The combined organic extracts were washed with NaHCO₃(aq) and brine, dried over anhydrous sodium sulfate, filtered, and concentrated. The residue was purified by flash column chromatography over silica gel with n-hexane/ethyl acetate (9:1) to afford the product S-V-III (12.02 g, y: 47%).

A solution of S-V-III (5.00 g) in toluene (30 mL) was heated at 120° C. for 8 h and then poured into water. The resulting mixture was extracted with ethyl acetate (3×50 mL). The combined organic extracts were washed with brine, dried over anhydrous sodium sulfate, filtered, and concentrated. The residue was purified by flash column chromatography over silica gel with n-hexane/ethyl acetate (3:1) to afford the compound S-V-IV (2.03 g, y: 42%).

A solution of S-V-IV (5.56 g), thiophenol (0.9 mL), and Cs₂CO₃ (7.95 g) in dry THF (40 mL) was stirred at 25° C. for 15 h and then poured into water. The resulting mixture was extracted with ethyl acetate (3×50 mL). The combined organic extracts were washed with brine, dried over anhydrous sodium sulfate, filtered, and concentrated. The residue was purified by flash column chromatography over silica gel with MeOH/NH₄OH (9:1) to afford compound S-V (2.80 g, y: 69%).

Preparation of S-VI

Side chain S-VI was prepared according to the schemes shown below:

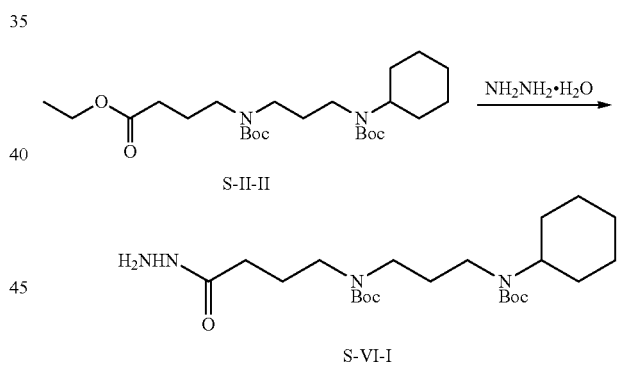

S-II-II

S-VI-I

A solution of S-II-II (42.05 g) and hydrazine monohydrate (31.31 g) in ethanol (420 mL) under an atmosphere of nitrogen was heated at 70° C. for 15 h and then concentrated. The residue was purified by flash column chromatography over silica gel with MeOH/DCM (1/19) to afford the product S-VI-I (25.30 g, y: 62%).

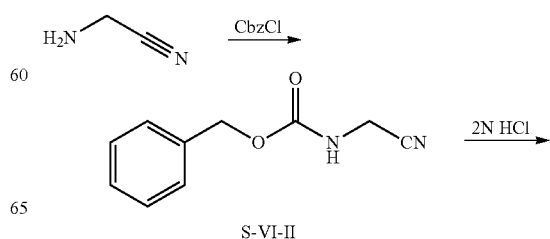

S-VI-II

-continued

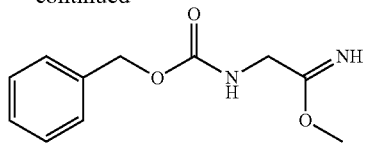

S-VI-III

To a solution of aminoacetonitrile hydrochloride (25.27 g) and $K_2CO_3$ (109.80 g) in THF/$H_2O$ (200 mL/400 mL) at 5-10° C. was added benzyl chloroformate (45.22 g) under an atmosphere of nitrogen. The mixture was stirred at room temperature for 15 h and then quenched with $NH_4Cl$(aq) (100 mL, 2 M). The resulting mixture was extracted with ethyl acetate (3×200 mL). The combined organic extracts were washed with water and brine, dried over anhydrous sodium sulfate, and filtered. The filtrate was concentrated to get the crude product S-VI-II (46.88 g, y: 90%).

To a solution of S-VI-II (7.01 g) in methanol (3 mL) was added HCl (50 ml, 2N in ether) dropwise. The mixture was stirred at 25° C. for 2 h and then filtered. The filtrated cake was dried to give the S-VI-III (8.02 g, y: 98%).

-continued

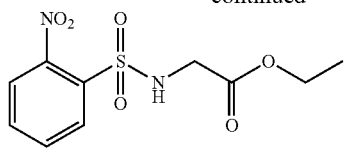

S-VII-I

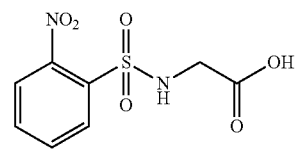

S-VII-II

To a solution of glycine ethyl ester hydrochloride (29.81 g) and triethylamine (64.74 g) in ethanol (600 mL) at 5-10° C. under an atmosphere of nitrogen was added to a solution of 2-nitrobenene sulfonyl chloride (47.22 g) in tetrahydrofuran (600 mL). The mixture was stirred at room tempera-

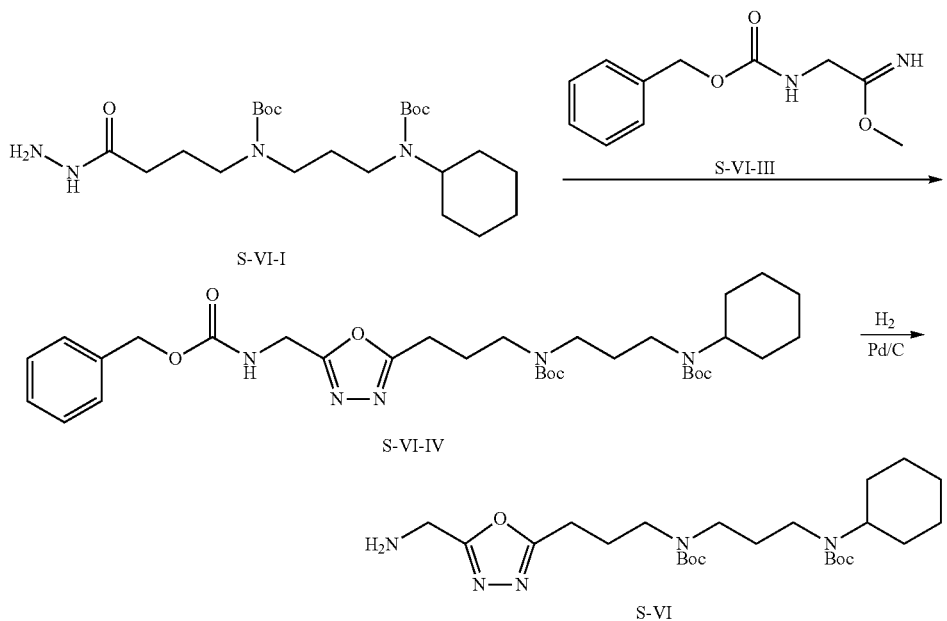

A solution of S-VI-I (3.71 g) and S-VI-III (8.02 g) in ACN (80 mL) was stirred at 60° C. for 48 h and then concentrated. The residue thus obtained was purified by flash chromatography on silica gel with n-hexane/ethyl acetate (1:1) to afford S-VI-IV (3.20 g, y: 63%).

A solution of S-VI-IV (3.20 g) and Pd/C (0.32 g) in EtOH (20 mL) was stirred under $H_2$(g) at 25° C. for 16 h. The resulting mixture was filtered and concentrated to afford S-VI (2.15 g, y: 85%).

Preparation of S-VII

Side chain S-VII was prepared according to the scheme shown below:

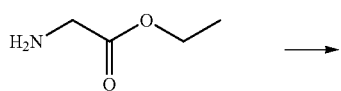

ture for 15 h and then concentrated. The residue was poured into water and the resulting mixture was extracted with ethyl acetate (3×500 mL). The combined organic extracts were washed with water and brine, dried over anhydrous sodium sulfate, filtered. The filtrate was concentrated to get the crude product S-VII-I (54.22 g, y: 88%).

To a magnetically stirred solution of compound S-VII-I (54.22 g) in MeOH/THF (300 mL/300 mL) under an atmosphere of nitrogen was added a solution of KOH (31.63 g) in $H_2O$ (100 mL). The reaction mixture was stirred at 25° C. for 15 h and then acidified with aqueous 4N HCl (140 mL). The resulting mixture was concentrated and the residue was extracted with ethyl acetate (3×300 mL). The combined organic extracts were washed with water and brine, dried over anhydrous sodium sulfate, and filtered. The filtrate was concentrated to get the crude product S-VII-II (39.10 g, y: 80%).

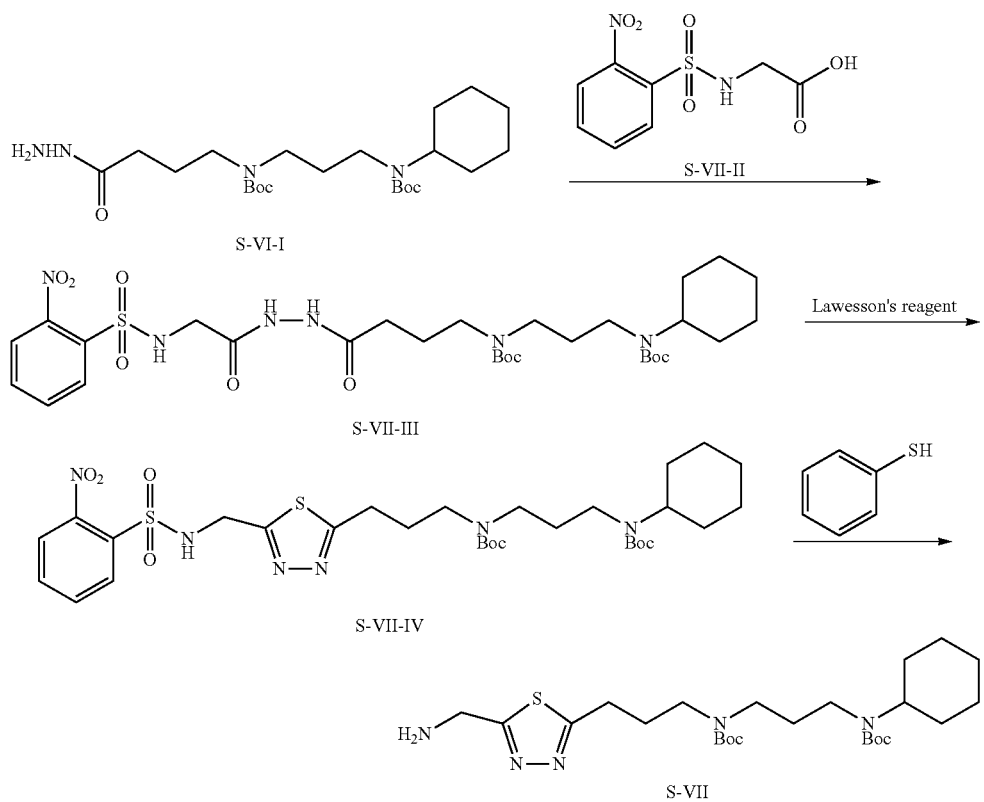

S-VI-I

S-VII-III

S-VII-IV

S-VII

To a magnetically stirred solution of S-VII-II (6.10 g) in dichloromethane (120 mL) under an atmosphere of nitrogen was added EDCI (4.93 g) at 25° C. After the mixture was stirred at 25° C. for 1 h, a solution of compound S-VI-I (8.23 g) in dichloromethane (20 mL) was added the mixture in one portion. The reaction mixture was stirred for another 6 h and then poured into water. The resulting mixture was extracted with dichloromethane (2×50 mL). The combined organic extracts were washed with brine, dried over anhydrous sodium sulfate, filtered, and concentrated. The residue thus obtained was purified by flash chromatography on silica gel with MeOH/DCM (1/19) to afford the product S-VII-III (8.52 g, y: 68%).

To a magnetically stirred solution of compound S-VII-III (8.52 g) in dichloromethane (200 mL) was added Lawesson's reagent (6.90 g). The mixture was stirred at room temperature for 15 h and then concentrated. The residue was purified by flash column chromatography on silica gel with n-hexane/ethyl acetate (1:1) to afford the product S-VII-IV (4.85 g, y: 57%).

A solution of S-VII-IV (6.40 g), cesium carbonate (5.97 g) and thiophenol (2.02 g) in acetonitrile (120 mL) under an atmosphere of nitrogen was stirred at 25° C. for 15 h and then concentrated. The residue was poured into water and then the aqueous layer was extracted with dichloromethane (3×120 mL). The combined organic extracts were washed with water and brine, dried over anhydrous sodium sulfate, filtered, and concentrated. The residue was purified by flash chromatography on silica gel with MeOH/NH₄OH (9:1) to afford the product S-VII (4.55 g, y: 97%).

Preparation of S-VIII

Side chain S-VIII was prepared according to the schemes shown below:

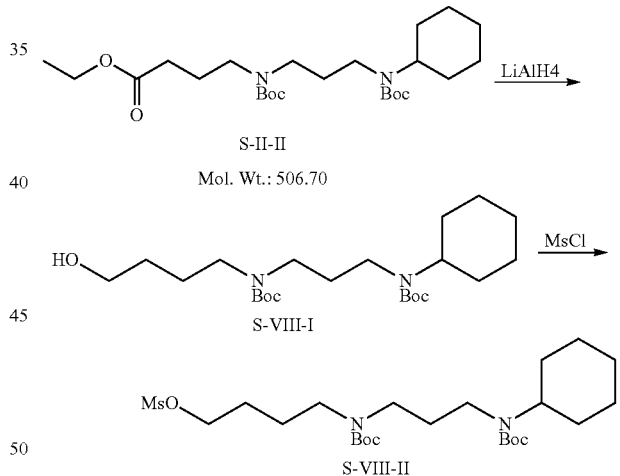

S-II-II
Mol. Wt.: 506.70

S-VIII-I

S-VIII-II

To a solution of LAH (1.14 g) in THF (94 mL) at 5-10° C. was added S-II-II (4.72 g) under an atmosphere of nitrogen. The mixture was stirred at room temperature for 6 h and then quenched with ammonium chloride NH₄Cl(aq) (5.7 mL, 2 M). After adding anhydrous sodium sulfate (5.71 g), the resulting mixture was stirred at 25° C. for another 1 h and then filtered. The filtrate was concentrated to get the crude product S-VIII-I (3.85 g y: 90%).

To a solution of S-VIII-I (3.85 g) and TEA (2.02 g) in dichloromethane (180 mL) at 5-10° C. was added MsCl (1.14 g) dropwise. The mixture was stirred at room temperature for 15 h and then quenched with NH₄Cl(aq). The aqueous phase was extracted with CH₂Cl₂ (2×50 mL). The combined organic extracts were washed with NaHCO₃(aq) and brine, dried over anhydrous sodium sulfate, and filtered. The filtrate was concentrated to get the crude product S-VIII-II (3.64 g, y: 80%).

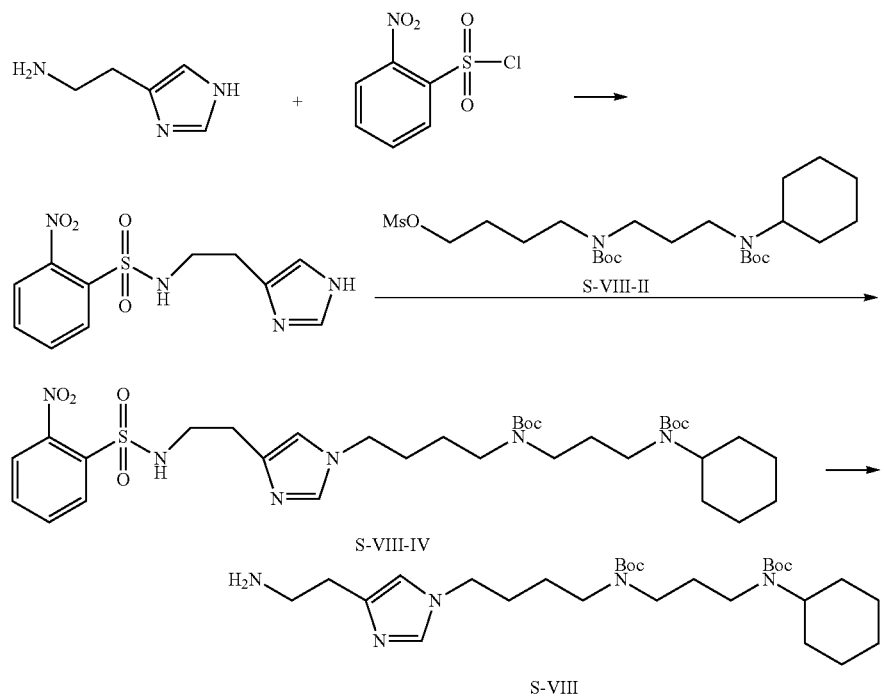

To a solution of histamine (1.02 g) and triethylamine (2.01 g) in dry THF (200 mL) at 5-10° C. was added a solution of 2-nitrobenene sulfonyl chloride (2.21 g) in dry THF (5 mL) dropwise over 5 min. The mixture was stirred at 25° C. for 15 h and then concentrated. The residue was poured into water and the resulting mixture was extracted with ethyl acetate (3×100 mL). The combined organic extracts were washed with water and brine, dried over anhydrous sodium sulfate, and filtered. The filtrate was concentrated to get the crude product S-VIII-III (1.61 g, y: 60%).

A solution of S-VIII-III (1.61 g), K$_2$CO$_3$ (3.73 g), and S-VIII-II (4.01 g) in DMF (30 mL) was heated at 80° C. for 15 h and then poured into water. The resulting mixture was extracted with ethyl acetate (3×100 mL). The combined organic extracts were washed with water and brine, dried over anhydrous sodium sulfate, filtered, and concentrated. The residue was purified by flash chromatography on silica gel with MeOH/DCM (1/19) to afford the product S-VIII-IV (0.76 g, y: 20%).

A solution of S-VIII-IV (0.76 g), cesium carbonate (0.41 g), and thiophenol (0.18 g) in acetonitrile (15 mL) under an atmosphere of nitrogen was stirred at 25° C. for 15 h and then concentrated. The residue was poured into water and the resulting mixture was extracted with dichloromethane (3×50 mL). The combined organic extracts were washed with water and brine, dried over anhydrous sodium sulfate, filtered, and concentrated. The residue was purified by flash chromatography on silica gel with MeOH/NH$_4$OH (9:1) to afford the product S-VIII (0.51 g, y: 91%).

Preparation of S-VIIII

Side chain S-VIIII was prepared according to the scheme shown below:

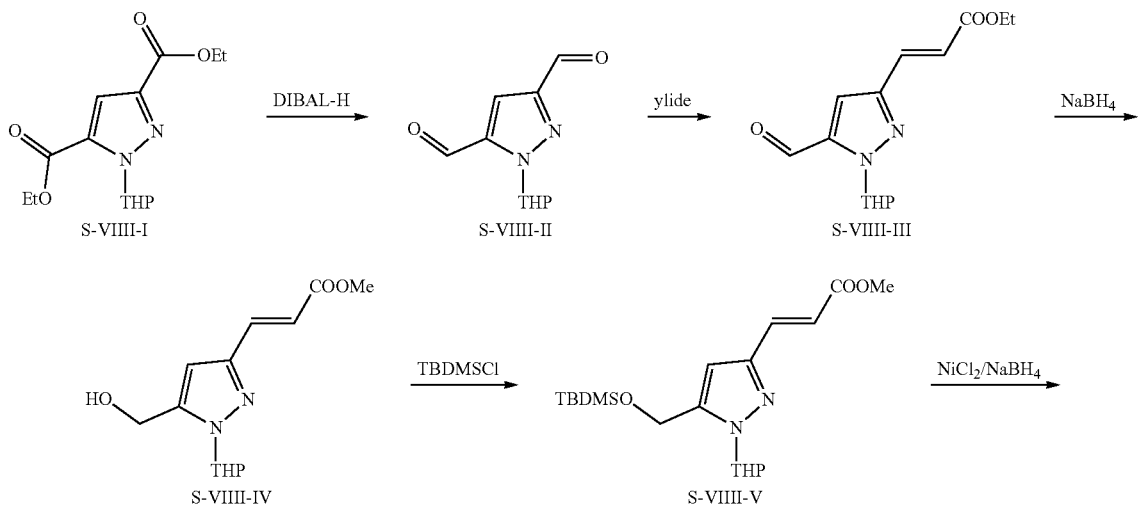

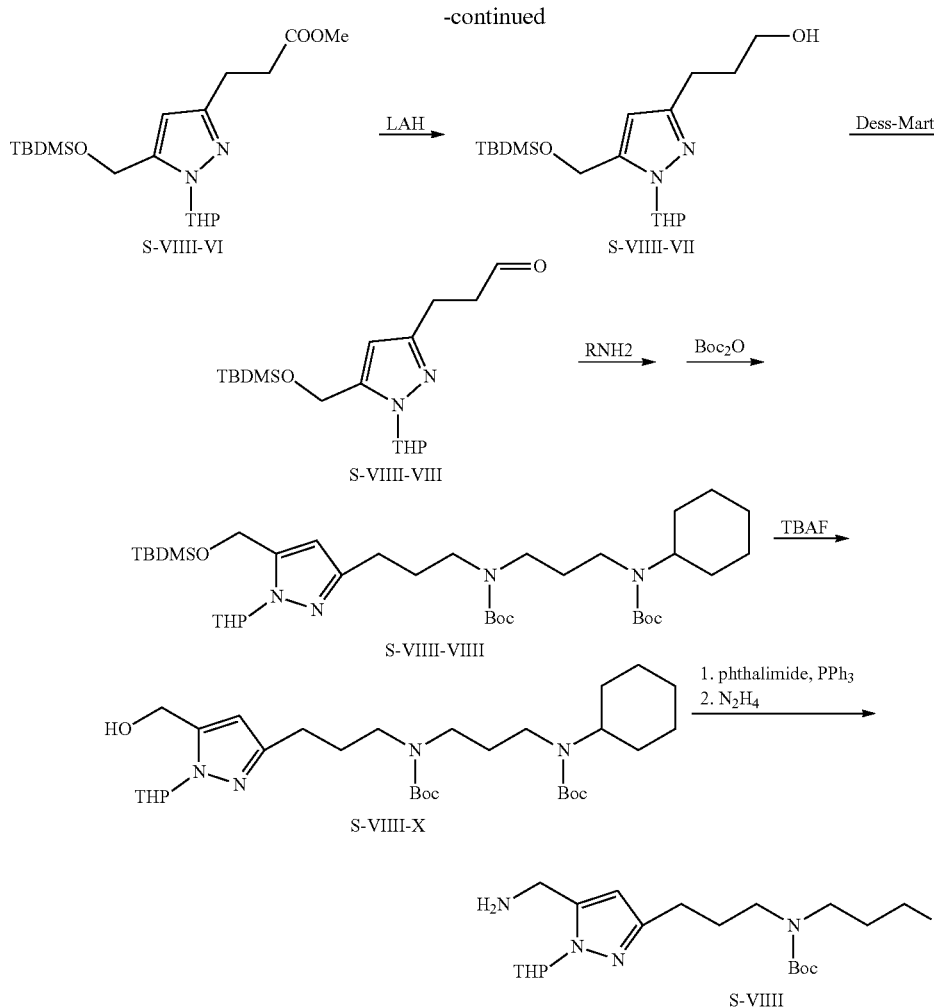

To a solution of S-VIIII-I (10.02 g) in dry CH$_2$Cl$_2$ (160 mL) was added DIBAL-H (70 mL, 1.0 M in toluene) at −78° C. The mixture was stirred at −78° C. for 1 h and then quenched with methanol (100 mL) at −78° C. The resulting mixture was filtrated and the filtrate was then concentrated to afford crude S-VIIII-II. A suspension of the (ethoxycarbonylmethylidene)triphenylphosphorane (6.91 g) and S-VIIII-II in toluene (160 mL) was heated at 80° C. for 2 h and then poured into water (100 mL). The aqueous phase was extracted with ethyl acetate (3×100 mL). The combined organic extracts were washed with brine, dried over anhydrous sodium sulfate, and filtered. The filtrate was then concentrated to afford crude S-VIIII-III. A solution of the compound S-VIIII-III and NaBH$_4$ (3.22 g) in MeOH (210 mL) was stirred at 25° C. for 15 h and then quenched with NH$_4$Cl(aq) (100 mL, 2M). The mixture was concentrated and residue was extracted with dichloromethane (3×100 mL). The combined organic extracts were washed with water and brine, dried over anhydrous sodium sulfate, filtered, and concentrated. The residue was purified by flash chromatography on silica gel with n-hexane/ethyl acetate (1:1) to afford S-VIIII-IV (3.51 g, y: 39% over three steps)

A solution of S-VIIII-IV (3.5 g), imidazole (1.81 g), and TBDMSCl (2.38 g) in DCM (160 mL) was stirred at 25° C. for 15 h and then poured into water. The aqueous phase was extracted with dichloromethane (3×100 mL). The combined organic extracts were washed with brine, dried over anhydrous sodium sulfate, and filtered. The filtrate was then concentrated to afford crude S-VIIII-V. To a solution of S-VIIII-V in MeOH (70 mL) at 0° C. was added with NiCl$_2$ (18 mg) and NaBH$_4$ (1.06 g). The mixture was stirred at 0° C. for 1 h and then quenched with NH$_4$Cl(aq) (1 mL, 2M). The resulting mixture was filtrated and the filtrate was concentrated to afford crude S-VIIII-VI. To a solution of the S-VIIII-VI in THF (70 mL) at 0° C. was added LAH (1.06 g). The mixture was stirred at 0° C. for 1 h and then quenched with NaOH(aq) (4 mL, 10% w/w). The resulting mixture was filtered and concentrated. The residue was purified by flash column chromatography on silica gel with n-hexane/ethyl acetate (1:1) to afford S-VIIII-VII (2.03 g, y: 43% over three steps).

To a solution of S-VIIII-VII (2.03 g) in dichloromethane (28 mL) at 0° C. was added Dess-Martin periodinane (2.51 g) under an atmosphere of nitrogen. The mixture was stirred at 0° C. for 1 h and then quenched with NaHCO$_3$(aq) (30 mL, 2 M) and Na$_2$S$_2$O$_3$(aq) (30 mL, 2 M). The aqueous phase was extracted with dichloromethane (3×100 mL). The combined organic extracts were washed with brine, dried over anhydrous sodium sulfate, and filtered. The filtrate was concentrated to get the crude S-VIIII-VIII. A solution of S-VIIII-VIII, N-cyclohexyl-1,3-propanediamine (1.07 g) and sodium triacetoxyborohydride (2.43 g) in dichloromethane (28 mL) was stirred at 25° C. for 15 h and then poured into NaHCO$_3$(aq) (30 mL, 2M). The aqueous layer was extracted with CH$_2$Cl$_2$ (2×50 mL). The combined organic extracts were washed with brine, dried over anhydrous sodium sulfate, and filtered. To a magnetically stirred filtrate and TEA (1.41 g) was added Boc$_2$O anhydride (3.26 g) in one portion. The mixture was stirred at room temperature for 15 h and then concentrated. The residue was purified by flash column chromatography on silica gel with n-hexane/ethyl acetate (3:1) to afford the product S-VIIII-VIIII. (2.27 g, y: 57% over 2 steps).

A solution of the compound S-VIIII-VIIII (2.27 g) and TBAF (4.9 mL, 1M in THF) in THF (16 mL) was stirred at 25° C. for 1 h and then poured into NaHCO$_3$(aq) (30 mL, 2M). The resulting mixture was extracted with ethyl acetate (2×100 mL). The combined organic extracts were washed with brine, dried over anhydrous sodium sulfate and filtered. The filtrate was concentrated to get the crude S-VIIII-X. To a solution of S-VIIII-X, phthalimide (0.51 g), and PPh$_3$ (0.91 g) in dry THF (15 mL) at 0° C. was added a solution of DEAD (0.72 g) in dry THF (1.5 mL) dropwise. The reaction mixture was stirred under nitrogen at 25° C. for 15 h and then concentrated. A solution of the residue and hydrazine monohydrate (0.8 mL) in MeOH (20 mL) was stirred at 25° C. for 15 h and then filtrated. The filtrated was concentrated and the resultant residue was purified by flash column chromatography on silica gel with MeOH/NH$_4$OH (9:1) to afford the S-VIIII (1.71 g, y: 90% over two steps)

Preparation of S-X

Side chain S-X was prepared according to the scheme shown below:

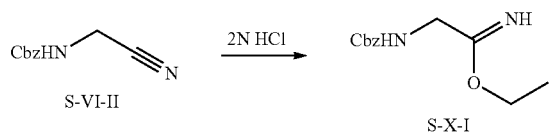

To a solution of S-VI-II (10.02 g) in ethanol (3 mL) was added HCl (50 ml, 2N in ether) dropwise. The resulting mixture was stirred at 25° C. for 2 h and then filtered. The filtrated cake was dried under reduced pressure to give the S-X-I (8.02 g, y: 64%).

A solution of S-VI-I (4.22 g), CH$_3$CO$_2$K (4.13 g), and S-X-I (4.73 g) in n-BuOH (80 mL) was stirred at 80° C. for 1 h, then 125° C. for 16 h and then concentrated. The residue was purified by flash chromatography over silica gel with n-hexane/ethyl acetate (1/1) to afford S-X-II (2.76 g, y: 30%).

A solution of S-X-II (1.82 g) and 10% Pd/C (0.18 g) in EtOH (20 mL) was stirred under H$_2$(g) at 25° C. for 16 h. The resulting mixture was filtered and concentrated to afford S-X (1.20 g, y: 84%).

Preparation of S-XI and S-XII

Side chains S-XI and S-XII were prepared according to the scheme shown below:

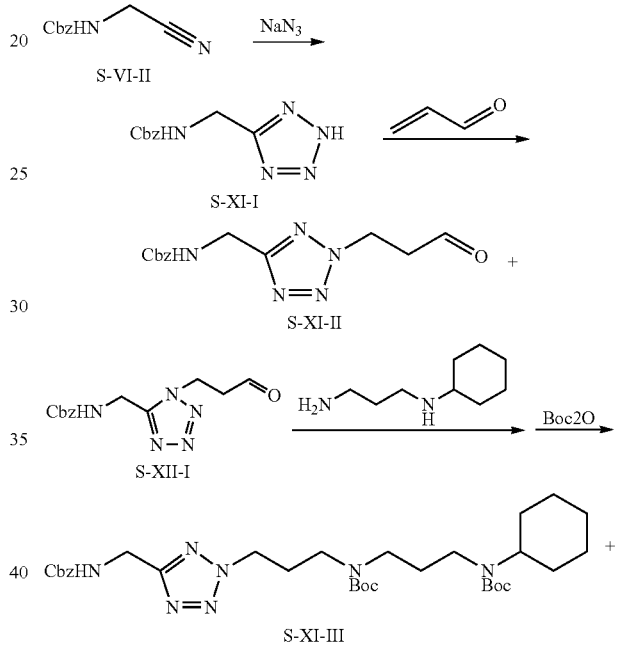

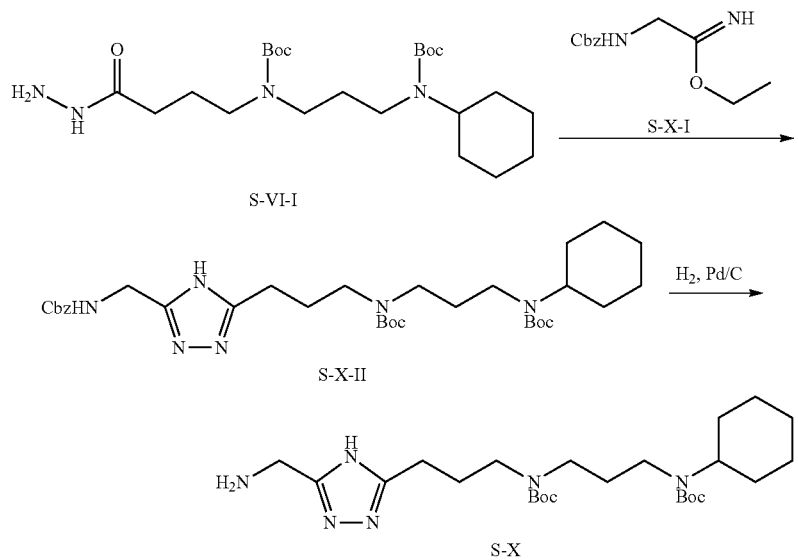

-continued

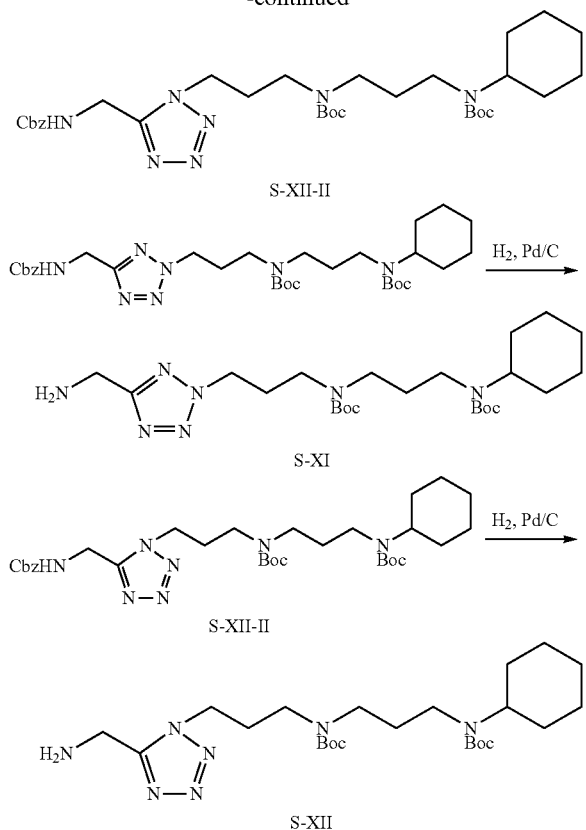

A solution of S-VI-II (37.10 g), sodium azide (31.73 g), and zinc bromide (30.75 g) in IPA/H$_2$O (300 mL/600 mL) under an atmosphere of nitrogen was stirred at 75° C. for 15 h. To the mixture at room temperature was added HCl(aq) (4 M) slowly until all solid has dissolved. The resulting mixture was extracted with ethyl acetate (3×200 mL). The combined organic extracts were washed with brine, dried over anhydrous sodium sulfate, and filtered. The filtrate was concentrated to get the crude product S-XI-I (43.22 g, y: 95%).

To a solution of S-XI-I (17.10 g) and TEA (29.65 g) in a solvent of CH$_2$Cl$_2$/MeOH (320 mL/32 mL) at 5-10° C. was added acrolein (16.43 g) dropwise. The resulting mixture was stirred at room temperature for 4 h and then quenched with NH$_4$Cl(aq) (50 mL). The resulting mixture was concentrated and then the residue was extracted with CH$_2$Cl$_2$ (3×200 mL). The combined organic extracts were washed with NaHCO$_3$(aq) and brine, dried over anhydrous sodium sulfate, filtered, and concentrated. The residue was purified by flash column chromatography over silica gel with MeOH/DCM (1/32) to afford the mixture product S-XI-II and S-XII-I (16.90 g, y: 80%).

To the mixture of S-XI-II and S-XII-I (25.10 g) in MeOH (250 mL) was added N-(3-aminopropyl)cyclohexylamine (16.26 g) under an atmosphere of nitrogen. The mixture was stirred at 0° C. for 2 h and NaBH$_4$ (2.78 g) was added to the mixture slowly. The resulting mixture was stirred for another 1 h and then quenched with NH$_4$Cl(aq). The mixture was concentrated and the residue was extracted with dichloromethane (3×150 mL). The combined organic extracts were washed with NaHCO$_3$(aq) and brine, dried over anhydrous sodium sulfate, and filtered. To the filtrate was added Boc$_2$O anhydride (45.44 g) in one portion. The mixture was stirred at room temperature for 15 h and then concentrated. The residue was purified by flash column chromatography over silica gel with n-hexane/ethyl acetate (1:1) to afford the product S-XI-III (12.82 g, y: 24% over 2 steps) and S-XII-II (11.20 g, y: 21% over 2 steps).

A solution of S-XI-III (15.80 g) and 10% Pd/C (1.58 g) in 2-propanol (158 mL) was stirred under H$_2$(g) at 60° C. for 15 h. The resulting mixture was filtered and the filtrate was concentrated under reduced pressure to give the product S-XI (12.10 g, y: 97%)

A solution of S-XII-II (11.20 g) and 10% Pd/C (1.12 g) in 2-propanol (112 mL) was stirred under H$_2$(g) at 60° C. for 15 h. The resulting mixture was filtered and the filtrate was concentrated under reduced pressure to give the product S-XII (8.37 g, y: 95%).

Preparation of S-XIII

Side chain S-XIII was prepared according to the scheme shown below:

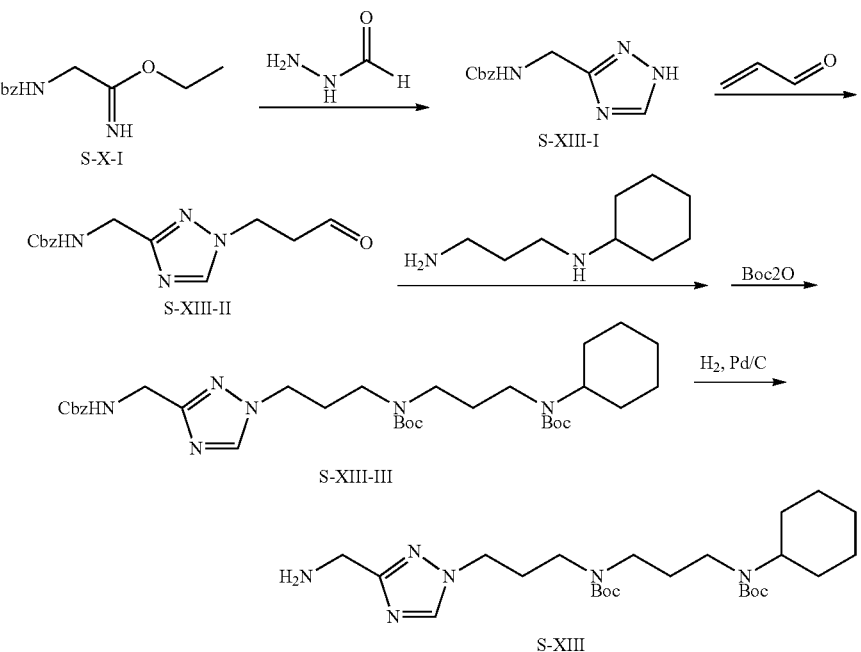

To a solution of S-X-I (10.02 g) in CH$_2$Cl$_2$ (100 mL) at 0° C. was added KOH(aq) (100 mL, 2.4% w/w). The mixture was stirred at 0° C. for 10 min and then extracted with dichloromethane (3×50 mL). The combined organic extracts were washed with water and brine, dried over anhydrous sodium sulfate, filtered and concentrated. A solution of the residue, formohydrazide (3.31 g), and CH$_3$CO$_2$K (3.33 g) in n-BuOH (100 mL) was stirred at 80° C. for 1 h, then 125° C. for 16 h and then concentrated. The residue was crystallization with n-Hexane/ethyl acetate (1/1) to afford S-XIII-I (7.21 g, y: 73%).

To a solution of S-XIII-I (4.05 g) and TEA (0.8 mL) in a solvent of MeOH (20 mL) at −10° C. was added acrolein (2 mL) dropwise. The resulting mixture was stirred at −10° C. for 3 h and then quenched with NH$_4$Cl(aq) (50 mL). The resulting mixture was concentrated and then the residue was extracted with ethyl acetate (3×50 mL). The combined organic extracts were washed with NaHCO$_3$(aq) and brine, dried over anhydrous sodium sulfate, filtered, and concentrated. The residue was purified by flash column chromatography over silica gel with MeOH/ethyl acetate (1:10) to afford S-XIII-II (2.08 g, y: 42%).

To the mixture of S-XIII-II (2.08 g) in MeOH (20 mL) at 0° C. was added N-(3-aminopropyl) cyclohexylamine (1.6 mL) under an atmosphere of nitrogen. The mixture was stirred at 0° C. for 2 h and NaBH$_4$ (0.45 g) was added to the mixture slowly. The resulting mixture was stirred for another 1 h and then quenched with NH$_4$Cl(aq).

The mixture was concentrated and the residue was extracted with dichloromethane (3×150 mL). The combined organic extracts were washed with NaHCO$_3$(aq) and brine, dried over anhydrous sodium sulfate, filtered. To the filtrate was added Boc$_2$O anhydride (1.58 g) in one portion. The mixture was stirred at room temperature for 15 h and then concentrated. The residue was purified by flash column chromatography over silica gel with n-hexane/ethyl acetate (1:2) to afford the product S-XIII-III (2.42 g, y: 54% over 2 steps).

A solution of S-XIII-III (5.41 g) and 10% Pd/C (0.54 g) in EtOH (20 mL) was stirred under H$_2$(g) at 25° C. for 15 h. The resulting mixture was filtered and the filtrate was concentrated under reduced pressure to give the product S-XIII (3.69 g, y: 87%)

Provided below are starting materials, i.e., 2,4-dichloro heterocyclic derivatives, for preparing Compounds 1-86.

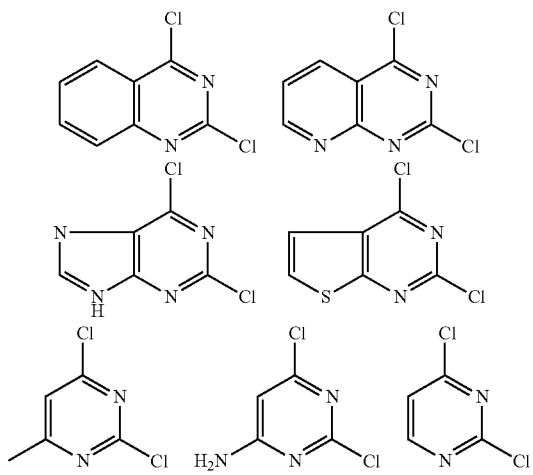

Depicted below is a synthetic route that was followed for synthesizing certain compounds of Formula (I) as shown in EXAMPLE 1 below. Compound A containing two halo groups reacted with an amino compound R$_4$—H to give compound B, which reacted with another amino compound R$_3$—H (which can be the same as R$_4$—H) to give compound C, i.e., a compound of Formula (I).

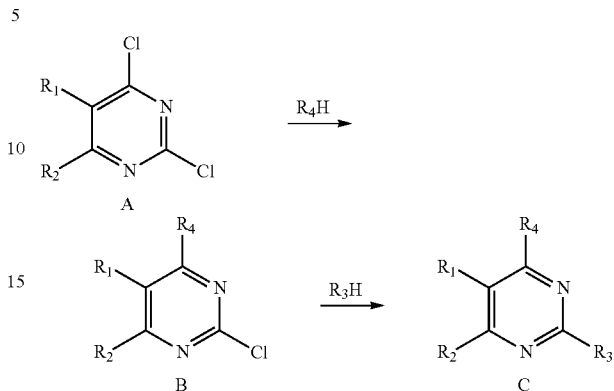

The compounds thus synthesized were purified by a method such as column chromatography, high-pressure liquid chromatography, or recrystallization.

The intermediates used in the synthesis described above were either commercially available or could be prepared by methods known in the art. The methods could also include additional steps, either before or after the steps described specifically herein, to add or remove suitable protecting groups if necessary to facilitate synthesis of the compounds. In addition, various synthetic steps could be performed in an alternate sequence or order to give the desired compounds.

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

EXAMPLE 1

Synthesis of Compounds 1-86

Compounds 1-86 were synthesized by assembling starting materials and side chain compounds set forth below:

Preparation of Compound 1

Shown below is a scheme for synthesizing compound 1 via intermediates 1-I and 1-II.

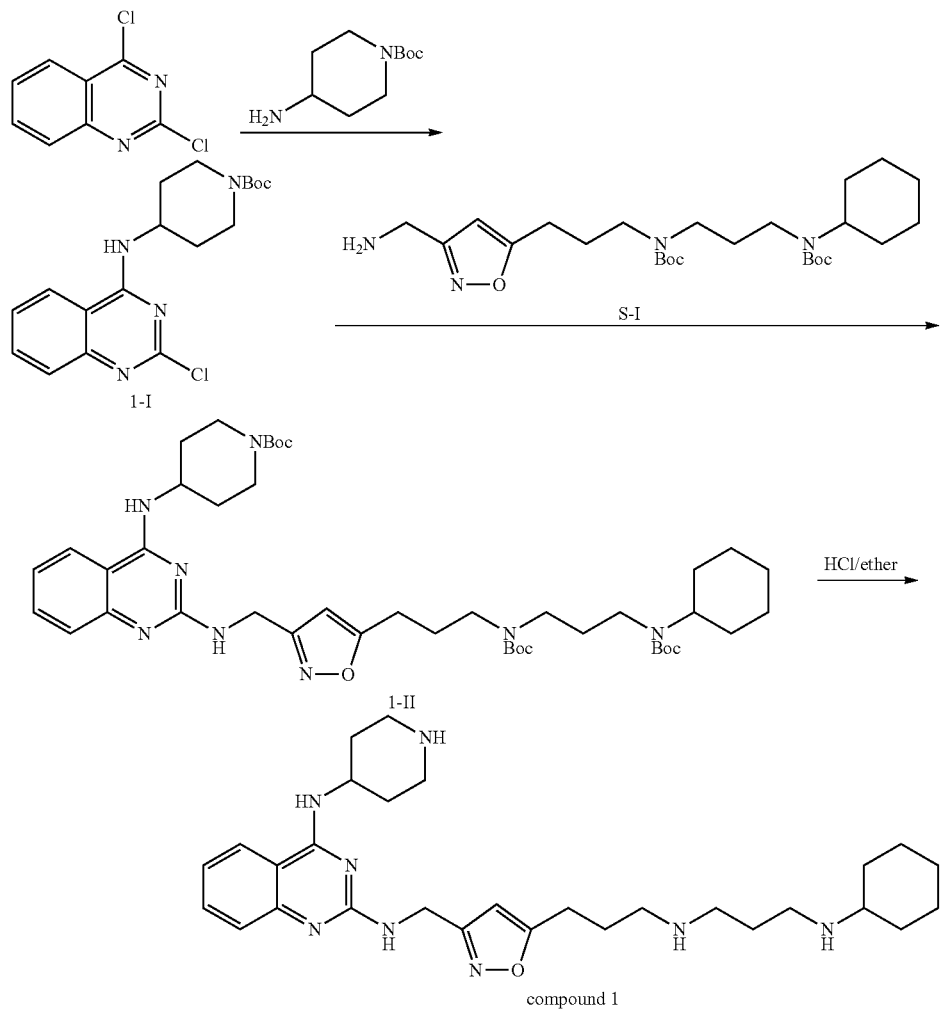

A solution of 2,4-dichloro-quinazoline (1.01 g), 4-aminopiperidine-1-carboxylic acid tert-butyl ester (1.05 g) and triethylamine (1.01 g) in THF (30 mL) under an atmosphere of nitrogen was stirred at 25° C. for 15 h and then quenched with aqueous $NH_4Cl$ (50 mL, 2 M). The resulting mixture was extracted with ethyl acetate (3×100 mL). The combined organic extracts were washed with brine, dried over anhydrous sodium sulfate, filtered, and concentrated. The residue thus obtained was purified by flash chromatography over silica gel with n-hexane/ethyl acetate (1:1) to afford compound 1-I (1.31 g, y: 71%).

A solution of compound 1-I (120.1 mg) and S-I (160.2 mg) in 1-pentanol (1.4 mL) was heated at 120° C. for 15 min using microwave radiation and then concentrated. The residue thus obtained was purified with flash chromatography on silica gel with MeOH/DCM (1/32) to afford compound 1-II (150.1 mg, y: 55%).

A solution of 1N HCl/diethyl ether (3 mL) was added to the solution of compound 1-II (150.1 mg) in dichloromethane (6 mL). The reaction mixture was stirred at 25° C. for 15 h and then concentrated to afford hydrochloride salt of compound 1 (98.6 mg, y: 86%). $^1H$ NMR (400 MHz, $D_2O$) δ 8.04 (d, 1H), 7.83 (dd, 1H), 7.49-7.43 (m, 2H), 6.38 (s, 1H), 4.77 (s, 2H), 4.46 (m, 1H), 3.58 (m, 2H), 3.25-3.13 (m, 8H), 2.93 (t, 2H), 2.21-2.03 (m, 8H), 1.99-1.81 (m, 4H), 1.69 (m, 1H), 1.41-1.17 (m, 6H); EI-MS: 521.5 (M+1).

Preparation of Compound 2

Compound 2 was prepared in a manner similar to that used to prepare compound 1. $^1H$ NMR (400 MHz, $D_2O$) δ 8.07 (d, 1H), 7.87-7.80 (m, 2H), 7.51-7.43 (m, 2H), 4.69 (s, 2H), 4.58 (m, 1H), 3.56 (m, 2H), 3.20-3.02 (m, 8H), 2.96 (t, 2H), 2.33 (m, 2H), 2.21-2.03 (m, 6H), 2.01-1.81 (m, 4H), 1.70 (m, 1H), 1.41-1.17 (m, 6H); EI-MS: 521.5 (M+1).

Preparation of Compound 3

Compound 3 was prepared in a manner similar to that used to prepare compound 1. $^1H$ NMR (400 MHz, $D_2O$) δ 8.01 (d, 1H), 7.79 (dd, 1H), 7.73 (s, 1H), 7.46-7.39 (m, 2H), 4.81 (s, 2H), 4.38 (m, 1H), 3.56 (m, 2H), 3.20-3.02 (m, 8H), 2.61 (t, 2H), 2.21-2.02 (m, 6H), 2.00-1.80 (m, 6H), 1.67 (m, 1H), 1.40-1.17 (m, 6H); EI-MS: 537.5 (M+1).

Preparation of Compound 4

Compound 4 was prepared in a manner similar to that used to prepare compound 1. $^1H$ NMR (400 MHz, $D_2O$) δ 8.06 (d, 1H), 7.84 (dd, 1H), 7.52-7.43 (m, 2H), 7.24 (s, 1H), 5.03 (s, 2H), 4.42 (m, 1H), 3.56 (m, 2H), 3.20-3.01 (m, 8H), 2.87 (t, 2H), 2.18-2.02 (m, 8H), 1.96-1.79 (m, 4H), 1.69 (m, 1H), 1.40-1.17 (m, 6H); EI-MS: 521.5 (M+1).

Preparation of Compound 5

Compound 5 was prepared in a manner similar to that used to prepare compound 1. $^1H$ NMR (400 MHz, $D_2O$) δ 8.05 (d, 1H), 7.83 (dd, 1H), 7.48-7.42 (m, 2H), 4.89 (s, 2H), 4.48 (m, 1H), 3.60 (m, 2H), 3.28-3.08 (m, 10H), 2.30-2.02 (m, 8H), 2.00-1.80 (m, 4H), 1.69 (m, 1H), 1.40-1.17 (m, 6H); EI-MS: 522.5 (M+1).

Preparation of Compound 6

Compound 6 was prepared in a manner similar to that used to prepare compound 1. $^1$H NMR (400 MHz, D$_2$O) δ 8.08 (d, 1H), 7.86 (m, 1H), 7.53-7.45 (m, 2H), 4.58 (m, 1H), 4.38 (s, 2H), 3.60 (m, 2H), 3.24-3.12 (m, 8H), 2.49 (t, 2H), 2.39 (m, 2H), 2.14-1.80 (m, 10H), 1.69 (m, 1H), 1.40-1.16 (m, 6H); EI-MS: 522.5 (M+1).

Preparation of Compound 7

Compound 7 was prepared in a manner similar to that used to prepare compound 1. $^1$H NMR (400 MHz, D$_2$O) δ 8.07 (d, 1H), 7.86 (dd, 1H), 7.53-7.45 (m, 2H), 5.13 (s, 2H), 4.40 (m, 1H), 3.58 (m, 2H), 3.30-3.11 (m, 10H), 2.24-2.02 (m, 8H), 2.00-1.82 (m, 4H), 1.69 (m, 1H), 1.40-1.16 (m, 6H); EI-MS: 538.5 (M+1).

Preparation of Compound 8

Compound 8 was prepared in a manner similar to that used to prepare compound 1. $^1$H NMR (400 MHz, D$_2$O) δ 8.80 (s, 1H), 8.06 (d, 1H), 7.82 (dd, 1H), 7.50-7.40 (m, 3H), 4.58 (m, 1H), 4.20 (t, 2H), 3.90 (t, 2H), 3.64 (m, 2H), 3.32-3.10 (m, 8H), 2.95 (m, 2H), 2.38 (m, 2H), 2.19-2.00 (m, 6H), 1.97-1.62 (m, 7H), 1.42-1.17 (m, 6H); EI-MS: 548.5 (M+1).

Preparation of Compound 9

Compound 9 was prepared in a manner similar to that used to prepare compound 1. $^1$H NMR (400 MHz, D$_2$O) δ 8.05 (d, 1H), 7.83 (dd, 1H), 7.48-7.44 (m, 2H), 6.33 (s, 1H), 4.80 (s, 2H), 4.45 (m, 1H), 3.54 (m, 2H), 3.20-3.06 (m, 8H), 2.80 (t, 2H), 2.20-2.02 (m, 8H), 2.00-1.80 (m, 4H), 1.69 (m, 1H), 1.40-1.17 (m, 6H); EI-MS: 520.5 (M+1).

Preparation of Compound 10

Compound 10 was prepared in a manner similar to that used to prepare compound 1. $^1$H NMR (400 MHz, D$_2$O) δ 8.02 (d, 1H), 7.82 (dd, 1H), 7.47-7.44 (m, 2H), 4.90 (s, 2H), 4.36 (m, 1H), 3.57 (m, 2H), 3.22-3.08 (m, 8H), 2.97 (t, 2H), 2.20-2.02 (m, 8H), 2.00-1.80 (m, 4H), 1.69 (m, 1H), 1.40-1.17 (m, 6H); EI-MS: 521.5 (M+1).

Preparation of Compound 11

Compound 11 was prepared in a manner similar to that used to prepare compound 1. $^1$H NMR (400 MHz, D$_2$O) δ 8.57 (s, 1H), 8.06 (d, 1H), 7.85 (m, 1H), 7.53-7.44 (m, 2H), 4.86 (s, 2H), 4.43 (m, 1H), 4.37 (t, 2H), 3.57 (m, 2H), 3.21-3.04 (m, 8H), 2.28 (m, 2H), 2.20-2.01 (m, 6H), 1.98-1.80 (m, 4H), 1.69 (m, 1H), 1.40-1.16 (m, 6H); EI-MS: 521.5 (M+1).

Preparation of Compound 12

Compound 12 was prepared in a manner similar to that used to prepare compound 1. EI-MS: 508.5 (M+1).

Preparation of Compound 13

Compound 13 was prepared in a manner similar to that used to prepare compound 1. $^1$H NMR (400 MHz, D$_2$O) δ 8.08 (d, 1H), 7.87 (dd, 1H), 7.54-7.46 (m, 2H), 5.08 (s, 2H), 4.47 (m, 1H), 3.59 (m, 2H), 3.26-3.15 (m, 10H), 2.45 (m, 2H), 2.21-2.01 (m, 6H), 1.99-1.81 (m, 4H), 1.71 (m, 1H), 1.39-1.17 (m, 6H); EI-MS: 522.5 (M+1).

Preparation of Compound 14

Compound 14 was prepared in a manner similar to that used to prepare compound 1. EI-MS: 522.5 (M+1).

Preparation of Compound 15

Shown below is a scheme for synthesizing compound 15 via intermediates 15-I and 15-II.

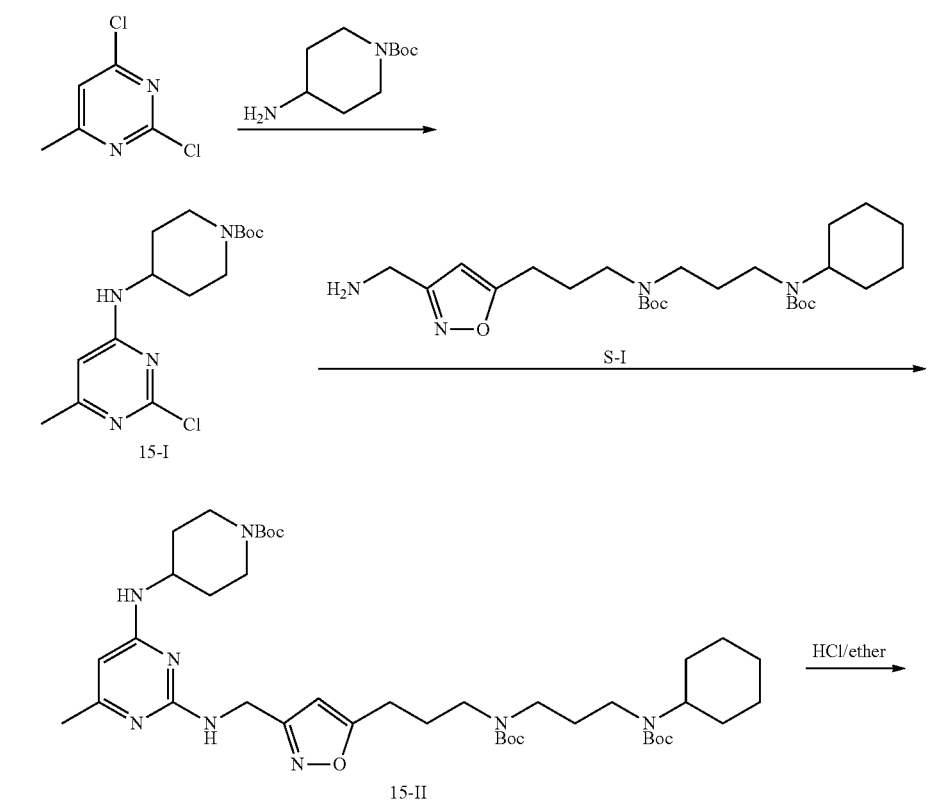

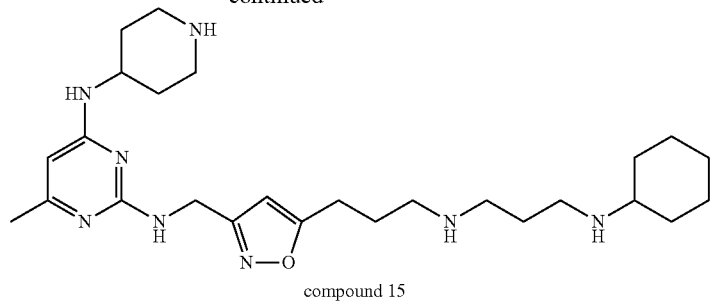

compound 15

A solution of 2,4-dichloro-6-methylpyrimidine (5.00 g), 4-amino-piperidine-1-carboxylic acid tert-butyl ester (8.36 g), and TEA (4.64 g) in THF (100 mL) under an atmosphere of nitrogen was stirred at 25° C. for 15 h and then quenched with aqueous NH$_4$Cl (50 mL, 2 M). The resulting mixture was extracted with ethyl acetate (3×100 mL) and the combined organic extracts were washed with brine, dried over anhydrous sodium sulfate, filtered, and concentrated. The residue thus obtained was purified by flash chromatography on silica gel with n-hexane/ethyl acetate (3:1) to afford compound 15-I (4.75 g, y: 47%).

A solution of 15-I (70.2 mg) and S-I (110.3 mg) in 1-pentanol (1.4 mL) was heated at 140° C. for 4 h and then concentrated. The residue thus obtained was purified with flash chromatography on silica gel with MeOH/DCM (1/32) to afford compound 15-II (100.1 mg, y: 59%).

A solution of 1N HCl/diethyl ether (2 mL) was added to the solution of compound 15-II (100.1 mg) in dichloromethane (4 mL). The mixture was stirred at 25° C. for 15 h and then concentrated to afford hydrochloride salt of compound 15 (67.8 mg, y: 89%). $^1$H NMR (400 MHz, D$_2$O) δ 6.33 (s, 1H), 5.95 (s, 1H), 4.69 (s, 2H), 4.16 (m, 1H), 3.49 (m, 2H), 3.27-3.07 (m, 8H), 2.93 (t, 2H), 2.28 (s, 3H), 2.19-1.99 (m, 8H), 1.87 (m, 2H), 1.79-1.64 (m, 3H), 1.42-1.17 (m, 6H); EI-MS: 485.5 (M+1).

Preparation of Compound 16

Compound 16 was prepared in a manner similar to that used to prepare compound 15. $^1$H NMR (400 MHz, D$_2$O) δ 7.78 (s, 1H), 5.95 (s, 1H), 4.56 (s, 2H), 4.27 (m, 1H), 3.49 (m, 2H), 3.22-3.14 (m, 8H), 2.95 (t, 2H), 2.26 (s, 3H), 2.20-2.04 (m, 8H), 1.90-1.77 (m, 4H), 1.64 (m, 1H), 1.40-1.16 (m, 6H); EI-MS: 485.5 (M+1).

Preparation of Compound 17

Compound 17 was prepared in a manner similar to that used to prepare compound 15. $^1$H NMR (400 MHz, D$_2$O) δ 7.31 (s, 1H), 5.97 (s, 1H), 4.95 (s, 2H), 4.11 (m, 1H), 3.43 (m, 2H), 3.21-3.00 (m, 8H), 2.88 (t, 2H), 2.35 (s, 3H), 2.18-1.99 (m, 8H), 1.85 (m, 2H), 1.76-1.62 (m, 3H), 1.41-1.17 (m, 6H); EI-MS: 501.5 (M+1).

Preparation of Compound 18

Compound 18 was prepared in a manner similar to that used to prepare compound 15. $^1$H NMR (400 MHz, D$_2$O) δ 7.71 (s, 1H), 5.96 (s, 1H), 4.72 (s, 2H), 4.15 (m, 1H), 3.46 (m, 2H), 3.23-3.03 (m, 8H), 2.61 (t, 2H), 2.28 (s, 3H), 2.18-1.96 (m, 8H), 1.86 (m, 2H), 1.79-1.64 (m, 3H), 1.41-1.18 (m, 6H); EI-MS: 485.5 (M+1).

Preparation of Compound 19

Compound 19 was prepared in a manner similar to that used to prepare compound 15. $^1$H NMR (400 MHz, D$_2$O) δ 5.96 (s, 1H), 4.77 (s, 2H), 4.15 (m, 1H), 3.50 (m, 2H), 3.24-3.08 (m, 10H), 2.28 (s, 3H), 2.26-2.03 (m, 8H), 1.87 (m, 2H), 1.80-1.63 (m, 3H), 1.40-1.17 (m, 6H); EI-MS: 486.4 (M+1).

Preparation of Compound 20

Compound 20 was prepared in a manner similar to that used to prepare compound 15. $^1$H NMR (400 MHz, D$_2$O) δ 6.00 (s, 1H), 4.25 (s, 2H), 4.17 (m, 1H), 3.50 (m, 2H), 3.25-3.06 (m, 10H), 2.29 (s, 3H), 2.26-2.02 (m, 8H), 1.90-1.73 (m, 4H), 1.68 (m, 1H), 1.40-1.17 (m, 6H); EI-MS: 486.4 (M+1).

Preparation of Compound 21

Compound 21 was prepared in a manner similar to that used to prepare compound 15. $^1$H NMR (400 MHz, D$_2$O) δ 5.98 (s, 1H), 5.01 (s, 2H), 4.16 (m, 1H), 3.47 (m, 2H), 3.28-3.06 (m, 10H), 2.29 (s, 3H), 2.25-1.97 (m, 8H), 1.87 (m, 2H), 1.78-1.62 (m, 3H), 1.40-1.16 (m, 6H); EI-MS: 502.5 (M+1).

Preparation of Compound 22

Compound 22 was prepared in a manner similar to that used to prepare compound 15. $^1$H NMR (400 MHz, D$_2$O) δ 8.74 (s, 1H), 7.40 (s, 1H), 5.94 (s, 1H), 4.39-4.25 (m, 3H), 3.80 (m, 2H), 3.54 (m, 2H), 3.27-3.05 (m, 10H), 2.29 (m, 2H), 2.26 (s, 3H), 2.19-2.02 (m, 4H), 2.00-1.79 (m, 8H), 1.70 (m, 1H), 1.42-1.17 (m, 6H); EI-MS: 512.5 (M+1).

Preparation of Compound 23

Compound 23 was prepared in a manner similar to that used to prepare compound 15. $^1$H NMR (400 MHz, D$_2$O) δ 5.96 (s, 1H), 4.95 (s, 2H), 4.13 (m, 1H), 3.49 (m, 2H), 3.28-3.09 (m, 10H), 2.45 (m, 2H), 2.28 (s, 3H), 2.19-2.00 (m, 6H), 1.87 (m, 2H), 1.79-1.64 (m, 3H), 1.42-1.16 (m, 6H); EI-MS: 486.4 (M+1).

Preparation of Compound 24

Compound 24 was prepared in a manner similar to that used to prepare compound 15. $^1$H NMR (400 MHz, D$_2$O) δ 5.95 (s, 1H), 4.75 (s, 2H), 4.03 (m, 1H), 3.46 (m, 2H), 3.22-3.01 (m, 8H), 2.91 (m, 2H), 2.28 (s, 3H), 2.20-2.02 (m, 6H), 1.93 (m, 2H), 1.86 (m, 2H), 1.77-1.62 (m, 3H), 1.41-1.17 (m, 6H); EI-MS: 485.4 (M+1).

Preparation of Compound 25

Compound 25 was prepared in a manner similar to that used to prepare compound 15. $^1$H NMR (400 MHz, D$_2$O) δ 6.01 (s, 1H), 5.03 (s, 2H), 4.09 (m, 1H), 3.48 (m, 2H), 3.26-3.04 (m, 10H), 2.60 (q, 2H), 2.24-1.96 (m, 9H), 1.84 (m, 2H), 1.70 (m, 2H), 1.41-1.13 (m, 9H); EI-MS: 516.5 (M+1).

Preparation of Compound 26

Compound 26 was prepared in a manner similar to that used to prepare compound 15. $^1$H NMR (400 MHz, D$_2$O) δ 5.98 (s, 1H), 4.97 (s, 2H), 4.14 (m, 1H), 3.46 (m, 2H), 3.22-3.12 (m, 10H), 2.58 (q, 2H), 2.46 (m, 2H), 2.20-2.02

(m, 6H), 1.88 (m, 2H), 1.80-1.66 (m, 3H), 1.41-1.13 (m, 9H); EI-MS: 500.5 (M+1).

Preparation of Compound 27

Compound 27 was prepared in a manner similar to that used to prepare compound 15. $^1$H NMR (400 MHz, D$_2$O) δ 5.98 (s, 1H), 4.77 (s, 2H), 4.06 (m, 1H), 3.47 (m, 2H), 3.28-3.02 (m, 8H), 2.93 (m, 2H), 2.58 (q, 2H), 2.20-1.96 (m, 8H), 1.87 (m, 2H), 1.69 (m, 3H), 1.41-1.13 (m, 9H); EI-MS: 499.5 (M+1).

Preparation of Compound 28

Compound 28 was prepared in a manner similar to that used to prepare compound 15. $^1$H NMR (400 MHz, D$_2$O) δ 6.38 (br s, 1H), 5.96 (s, 1H), 4.72 (s, 2H), 4.16 (m, 1H), 3.48 (m, 2H), 3.21-3.04 (m, 8H), 2.82 (m, 2H), 2.29 (s, 3H), 2.17-2.00 (m, 8H), 1.87 (m, 2H), 1.77-1.64 (m, 3H), 1.42-1.17 (m, 6H); EI-MS: 484.5 (M+1).

Preparation of Compound 29

Shown below is a scheme for synthesizing compound 29 via intermediates 29-I-29-IV.

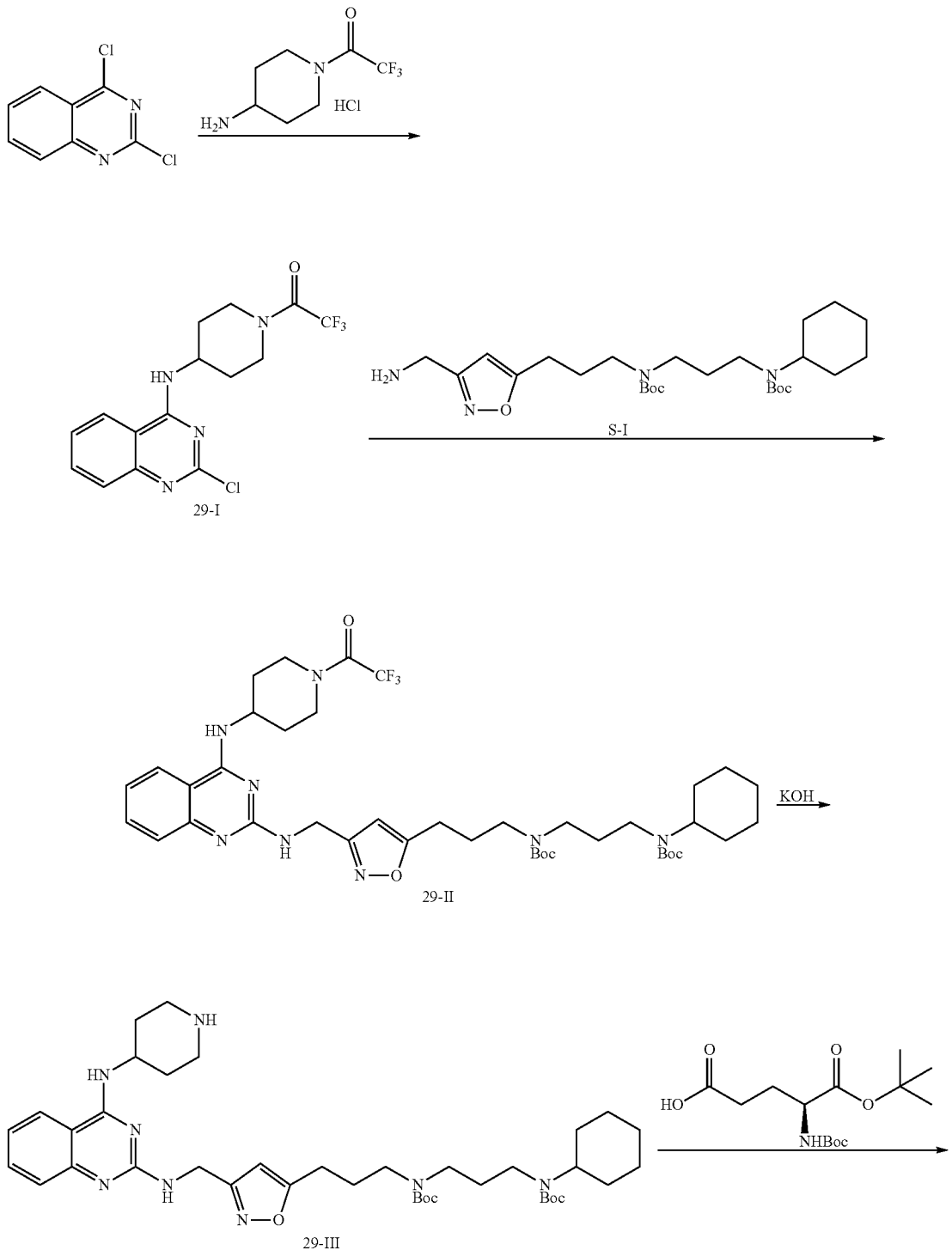

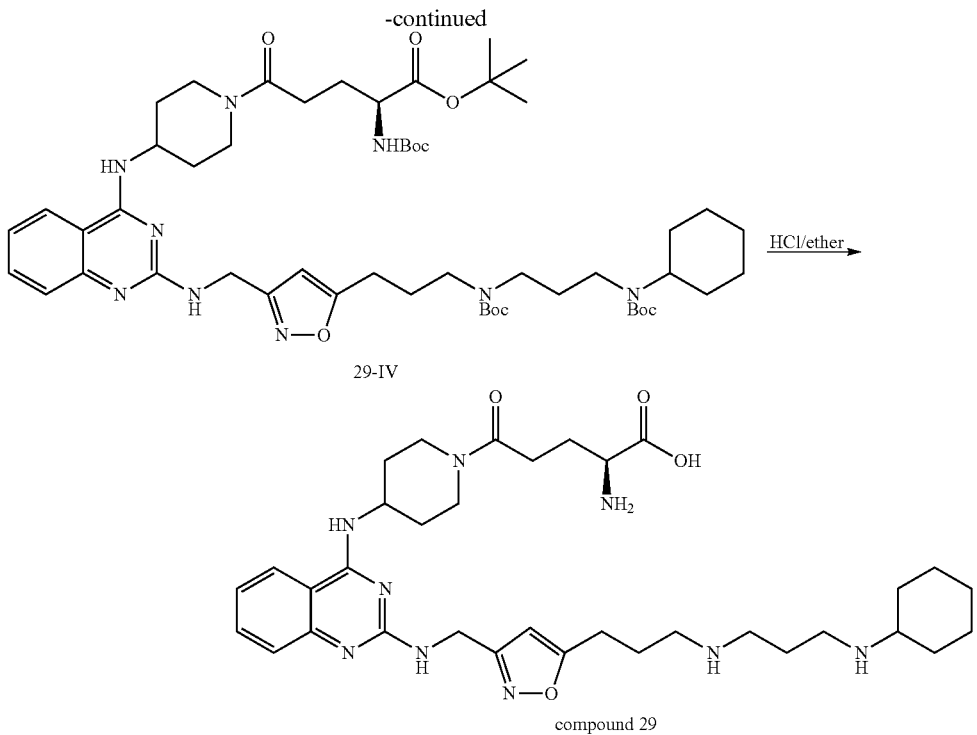

compound 29

A solution of 2,4-dichloro-quinazoline (1.02 g), hydrochloride salt of 1-(4-amino-piperidin-1-yl)-2,2,2-trifluoroethanone (1.21 g), and TEA (1.02 g) in THF (30 mL) under an atmosphere of nitrogen was stirred at 25° C. for 15 h and then quenched with aqueous $NH_4Cl$ (50 mL, 2 M). The resulting mixture was extracted with ethyl acetate (3×100 mL). The combined organic extracts were washed with brine, dried over anhydrous sodium sulfate, filtered, and concentrated. The residue thus obtained was purified by flash chromatography on silica gel with n-hexane/ethyl acetate (1:1) to give compound 29-I (1.37 g, y: 75%).

A solution of compound 29-I (0.26 g) and S-I (0.36 g) in 1-pentanol (2 mL) was heated at 120° C. for 15 min using microwave radiation and then concentrated. The residue thus obtained was purified by flash chromatography on silica gel with MeOH/DCM (1:32) to afford compound 29-II (0.29 g, y: 49%).

To a magnetically stirred solution of compound 29-II (0.29 g) in MeOH/THF (2.6 mL/2.6 mL) under an atmosphere of nitrogen was added a solution of KOH (0.05 g) in $H_2O$ (0.52 mL). The mixture was stirred at 25° C. for 15 h and then concentrated. The residue thus obtained was extracted with dichloromethane (3×50 mL). The combined organic extracts were washed with brine, dried over anhydrous sodium sulfate, and filtered. The filtrate was concentrated to give the crude compound 29-III (0.24 g, y: 94%).

To a magnetically stirred solution of 2-tert-butoxycarbonylamino-pentanedioic acid 1-tert-butyl ester (300.2 mg) in dichloromethane (20 mL) under an atmosphere of nitrogen was added EDCI (120.3 mg) and HOBt (96.2 mg) at 25° C. After the mixture was stirred at 25° C. for 1 h, a solution of 29-III (240.2 mg) in dichloromethane (10 mL) was added to the mixture in one portion. The reaction mixture was stirred for another 6 h and then poured into water. The resulting mixture was extracted with dichloromethane (2×50 mL). The combined organic extracts were washed with brine, dried over anhydrous sodium sulfate, filtered, and concentrated. The residue thus obtained was purified by flash chromatography on silica gel with MeOH/DCM (1:19) to give 29-IV (170.1 mg, y: 51%).

A solution of 4N HCl/dioxane (0.85 mL) was added to the solution of 29-IV (170.1 mg) in dichloromethane/1,4-dioxane (3.4 mL/3.4 mL). The mixture was stirred at 25° C. for 15 h and concentrated to afford hydrochloride salt of compound 29 (115.7 mg, y: 90%). $^1$H NMR (400 MHz, $D_2O$) δ 7.98 (d, 1H), 7.79 (t, 1H), 7.47-7.38 (m, 2H), 6.36 (s, 1H), 4.77 (s, 2H), 4.45 (m, 1H), 4.38 (m, 1H), 4.06-3.96 (m, 2H), 3.30 (m, 1H), 3.26-3.12 (m, 6H), 2.93 (m, 2H), 2.80 (m, 1H), 2.72 (m, 2H), 2.22 (m, 2H), 2.16-1.79 (m, 10H), 1.66 (m, 2H), 1.51 (m, 1H), 1.39-1.15 (m, 6H); EI-MS: 650.5 (M+1).

Preparation of Compound 30

Compound 30 was prepared in a manner similar to that used to prepare compound 29. $^1$H NMR (400 MHz, $D_2O$) δ 7.94 (m, 1H), 7.82-7.71 (m, 2H), 7.42-7.42 (m, 2H), 4.64 (s, 2H), 4.48-4.40 (m, 2H), 4.08-3.99 (m, 2H), 3.30-3.06 (m, 7H), 2.93 (m, 2H), 2.84 (m, 1H), 2.72 (m, 2H), 2.23-1.98 (m, 9H), 1.90-1.79 (m, 3H), 1.67 (m, 2H), 1.56 (m, 1H), 1.41-1.15 (m, 6H); EI-MS: 650.5 (M+1).

Preparation of Compound 31

Compound 31 was prepared in a manner similar to that used to prepare compound 29. $^1$H NMR (400 MHz, $D_2O$) δ 7.97 (d, 1H), 7.78 (t, 1H), 7.48 (s, 1H), 7.44-7.38 (m, 2H), 5.15 (d, 1H), 5.11 (d, 1H), 4.42 (m, 1H), 4.31 (m, 1H), 4.14 (m, 1H), 4.01 (m, 1H), 3.21-3.04 (m, 7H), 2.94 (m, 2H), 2.75-2.66 (m, 3H), 2.25 (m, 2H), 2.19-1.78 (m, 10H), 1.67 (m, 2H), 1.49 (m, 1H), 1.40-1.17 (m, 6H); EI-MS: 666.5 (M+1).

Preparation of Compound 32

Compound 32 was prepared in a manner similar to that used to prepare compound 29. $^1$H NMR (400 MHz, $D_2O$) δ 8.00 (d, 1H), 7.81 (t, 1H), 7.73 (s, 1H), 7.46-7.41 (m, 2H), 4.81 (s, 2H), 4.46 (m, 1H), 4.31 (m, 1H), 4.08-3.99 (m, 2H), 3.23 (m, 1H), 3.18-3.04 (m, 6H), 2.78-2.73 (m, 3H), 2.62 (m, 2H), 2.24 (m, 2H), 2.11-1.78 (m, 10H), 1.64 (m, 2H), 1.53 (m, 1H), 1.40-1.17 (m, 6H); EI-MS: 650.5 (M+1).

Preparation of Compound 33

Compound 33 was prepared in a manner similar to that used to prepare compound 29. $^1$H NMR (400 MHz, $D_2O$) δ 8.01 (d, 1H), 7.82 (t, 1H), 7.47-7.42 (m, 2H), 4.81 (s, 2H), 4.50 (m, 1H), 4.39 (m, 1H), 4.04-3.96 (m, 2H), 3.26-3.12

(m, 9H), 2.83 (m, 1H), 2.71 (m, 2H), 2.24-2.18 (m, 4H), 2.17-1.81 (m, 8H), 1.68 (m, 2H), 1.53 (m, 1H), 1.40-1.17 (m, 6H); EI-MS: 651.5 (M+1).

Preparation of Compound 34

Compound 34 was prepared in a manner similar to that used to prepare compound 29. $^1$H NMR (400 MHz, D$_2$O) δ 8.00 (d, 1H), 7.80 (t, 1H), 7.46-7.38 (m, 2H), 4.56-4.42 (m, 2H), 4.33 (s, 2H), 4.06-4.00 (m, 2H), 3.27 (m, 1H), 3.20-3.10 (m, 6H), 2.86 (m, 1H), 2.72 (m, 2H), 2.47 (m, 2H), 2.24-1.98 (m, 9H), 1.86-1.58 (m, 6H), 1.40-1.14 (m, 6H); EI-MS: 651.5 (M+1).

Preparation of Compound 35

Compound 35 was prepared in a manner similar to that used to prepare compound 29. $^1$H NMR (400 MHz, D$_2$O) δ 8.01 (d, 1H), 7.83 (t, 1H), 7.49-7.43 (m, 2H), 5.11 (d, 1H), 5.07 (d, 1H), 4.46 (m, 1H), 4.32 (m, 1H), 4.06-3.98 (m, 2H), 3.36-3.12 (m, 9H), 2.72-2.66 (m, 3H), 2.24-2.04 (m, 8H), 1.98-1.76 (m, 4H), 1.66 (m, 2H), 1.53 (m, 1H), 1.40-1.17 (m, 6H); EI-MS: 667.5 (M+1).

Preparation of Compound 36

Compound 36 was prepared in a manner similar to that used to prepare compound 29. $^1$H NMR (400 MHz, D$_2$O) δ 8.74 (s, 1H), 8.03 (d, 1H), 7.83 (t, 1H), 7.51-7.39 (m, 3H), 4.57-4.41 (m, 2H), 4.17 (m, 2H), 4.15-4.02 (m, 2H), 3.91 (m, 2H), 3.35-3.12 (m, 7H), 3.01-2.81 (m, 3H), 2.77 (m, 2H), 2.31-2.03 (m, 8H), 1.99-1.60 (m, 9H), 1.40-1.17 (m, 6H); EI-MS: 677.6 (M+1).

Preparation of Compound 37

Compound 37 was prepared in a manner similar to that used to prepare compound 29. $^1$H NMR (400 MHz, D$_2$O) δ 8.02 (d, 1H), 7.83 (t, 1H), 7.51-7.41 (m, 2H), 5.07 (d, 1H), 5.03 (d, 1H), 4.47 (m, 1H), 4.37 (m, 1H), 4.07-3.96 (m, 2H), 3.35-3.12 (m, 9H), 2.87 (m, 1H), 2.73 (m, 2H), 2.46 (m, 2H), 2.23 (m, 2H), 2.17-2.01 (m, 4H), 2.00-1.80 (m, 4H), 1.68 (m, 2H), 1.57 (m, 1H), 1.40-1.17 (m, 6H); EI-MS: 651.5 (M+1).

Preparation of Compound 38

Compound 38 was prepared in a manner similar to that used to prepare compound 29. $^1$H NMR (400 MHz, D$_2$O) δ 7.95 (d, 1H), 7.42 (t, 1H), 7.42-7.38 (m, 2H), 4.92 (d, 1H), 4.87 (d, 1H), 4.41 (m, 1H), 4.22 (m, 1H), 4.11 (m, 1H), 4.02 (m, 1H), 3.22-3.08 (m, 7H), 2.99 (t, 2H), 2.75 (m, 2H), 2.62 (m, 1H), 2.30-2.00 (m, 8H), 1.99-1.72 (m, 4H), 1.67 (m, 2H), 1.49 (m, 1H), 1.40-1.17 (m, 6H); EI-MS: 650.6 (M+1).

Preparation of Compound 39

Shown below is a scheme for synthesizing compound 39 via intermediates 39-I-39-V.

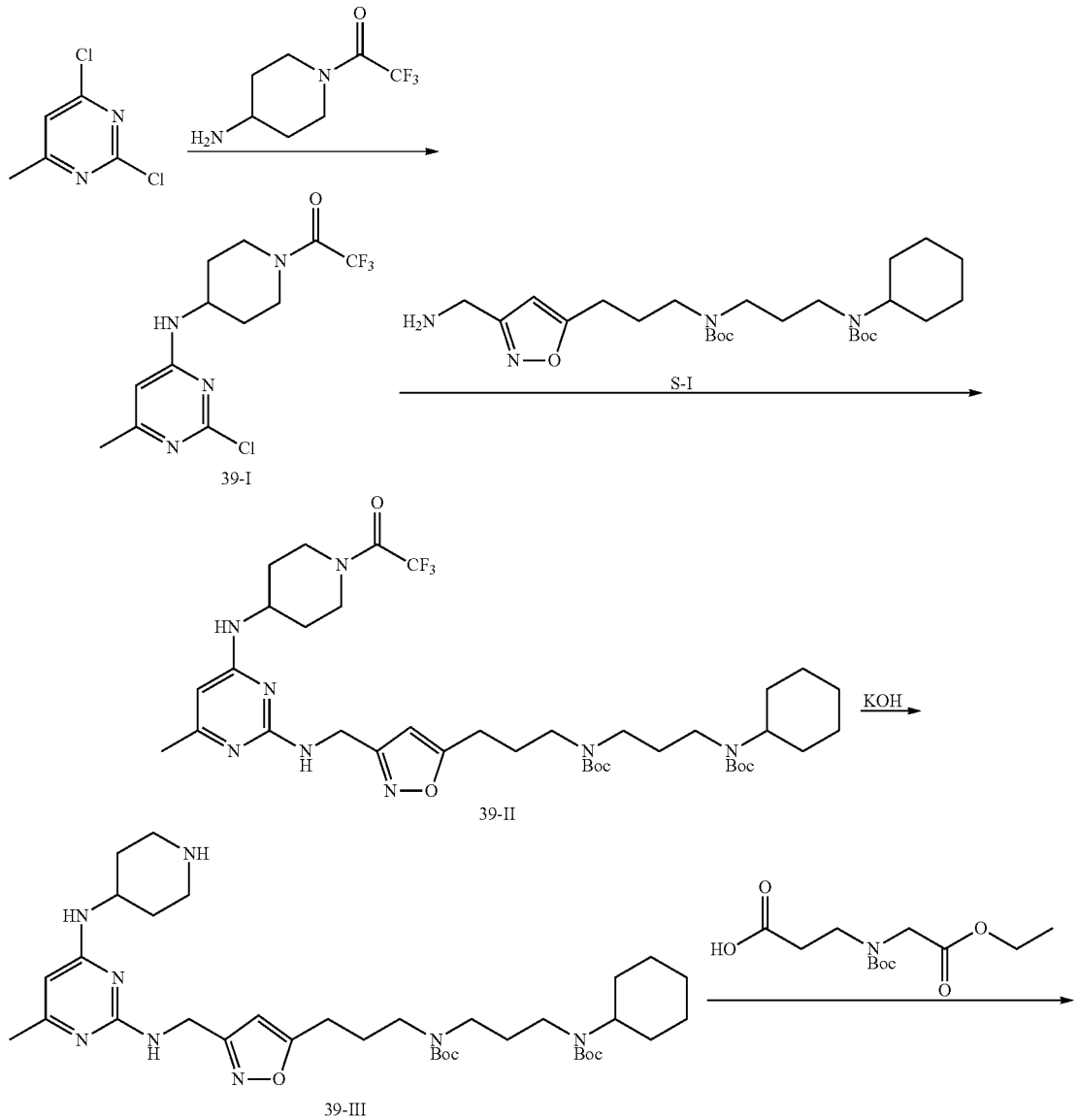

-continued

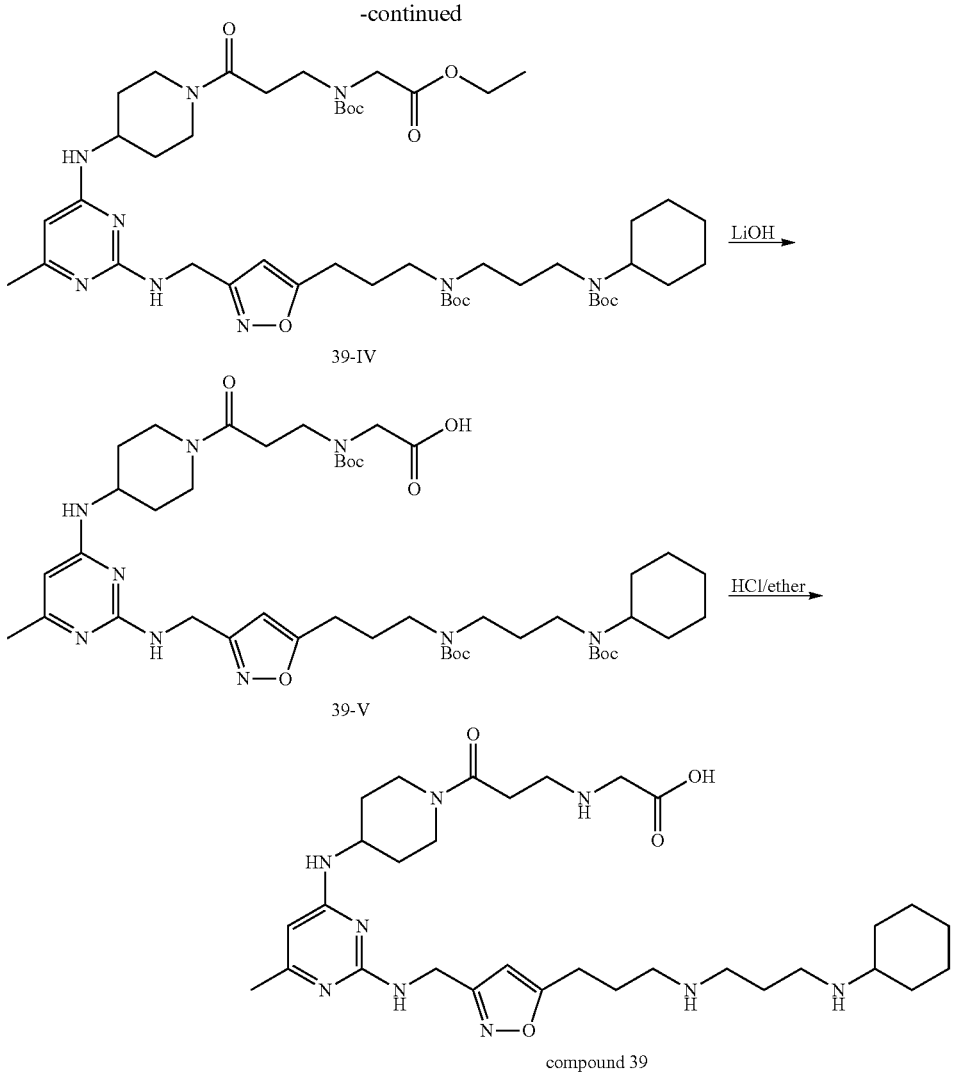

compound 39

A solution of 2,4-dichloro-6-methylpyrimidine (0.82 g), hydrochloride salt of 1-(4-Amino-piperidin-1-yl)-2,2,2-trifluoro-ethanone (1.21 g), and TEA (1.02 g) in THF (30 mL) under an atmosphere of nitrogen was stirred at 25° C. for 15 h and then quenched with aqueous $NH_4Cl$ (50 mL, 2 M). The resulting mixture was extracted with ethyl acetate (3×100 mL). The combined organic extracts were washed with brine, dried over anhydrous sodium sulfate, filtered, and concentrated. The residue thus obtained was purified by flash chromatography on silica gel with n-hexane/ethyl acetate (1:1) to give compound 39-I (1.07 g, y: 66%).

A solution of compound 39-I (0.24 g) and S-I (0.36 g) in 1-pentanol (2 mL) was heated at 120° C. for 15 min using microwave radiation and then concentrated. The residue thus obtained was purified by flash chromatography on silica gel with MeOH/DCM (1:32) to afford compound 39-II (0.33 g, y: 57%).

To a magnetically stirred solution of compound 39-II (0.33 g) in MeOH/THF (2.6 mL/2.6 mL) under an atmosphere of nitrogen was added a solution of KOH (0.05 g) in $H_2O$ (0.52 mL). The mixture was stirred at 25° C. for 15 h and then concentrated. The residue thus obtained was extracted with dichloromethane (3×50 mL). The combined organic extracts were washed with brine, dried over anhydrous sodium sulfate, and filtered. The filtrate was concentrated to give the crude compound 39-III (0.23 g, y: 79%).

To a magnetically stirred solution of 3-(tert-Butoxycarbonyl-ethoxycarbonylmethyl-amino)-propionic acid (280.1 mg) in dichloromethane (20 mL) under an atmosphere of nitrogen was added EDCI (116.4 mg) and HOBt (92.5 mg) at 25° C. After the mixture was stirred at 25° C. for 1 h, a solution of 39-III (232.8 mg) in dichloromethane (20 mL) was added to the mixture in one portion. The reaction mixture was stirred for another 6 h and then poured into water. The resulting mixture was extracted with dichloromethane (2×50 mL). The combined organic extracts were washed with brine, dried over anhydrous sodium sulfate, filtered, and concentrated. The residue thus obtained was purified by flash chromatography on silica gel with MeOH/DCM (1:19) to give 39-IV (231.4 mg, y: 72%).

To a solution of 39-IV (231.4 mg) in THF (30 mL) under an atmosphere of nitrogen was added a solution of LiOH(aq) (1 mL, 1N). The mixture was stirred at 25° C. for 15 h and then quenched with $NH_4Cl$(aq) (20 mL, 2M). The aqueous phase was extracted with ethyl acetate (3×50 mL). The combined organic extracts were washed with water and brine, dried over anhydrous sodium sulfate, filtered. The filtrate was concentrated to get the crude residue 39-V (200.4 mg, y: 89%).

A solution of 4N HCl/dioxane (1 mL) was added to the solution of 39-V (200.4 mg) in dichloromethane/1,4-dioxane (4 mL/4 mL). The mixture was stirred at 25° C. for 15 h and concentrated to afford hydrochloride salt of compound 39 (154.7 mg, y: 98%). $^1$H NMR (400 MHz, D$_2$O) δ 6.34 (s, 1H), 5.92 (s, 1H), 4.73 (d, 1H), 4.65 (d, 1H), 4.30 (m, 1H), 4.10 (m, 1H), 3.90 (s, 2H), 3.88 (m, 1H), 3.41 (t, 2H), 3.31-3.12 (m, 7H), 3.00-2.82 (m, 5H), 2.30 (s, 3H), 2.18-2.00 (m, 7H), 1.98-1.77 (m, 4H), 1.70 (m, 1H), 1.53 (m, 1H), 1.46-1.16 (m, 6H); EI-MS: 614.5 (M+1).

Preparation of Compound 40

Compound 40 was prepared in a manner similar to that used to prepare compound 39. $^1$H NMR (400 MHz, D$_2$O) δ 7.78 (s, 1H), 5.91 (s, 1H), 4.58 (d, 1H), 4.52 (d, 1H), 4.32-4.20 (m, 2H), 3.97 (s, 2H), 3.92 (m, 1H), 3.44 (m, 2H), 3.36-3.12 (m, 7H), 3.04-2.90 (m, 5H), 2.26 (s, 3H), 2.21-1.80 (m, 10H), 1.69 (m, 1H), 1.57 (m, 1H), 1.46 (m, 1H), 1.40-1.16 (m, 6H); EI-MS: 614.5 (M+1).

Preparation of Compound 41

Compound 41 was prepared in a manner similar to that used to prepare compound 39. $^1$H NMR (400 MHz, D$_2$O) δ 7.39 (s, 1H), 5.92 (s, 1H), 5.00 (d, 1H), 4.92 (d, 1H), 4.22 (m, 1H), 4.04 (m, 1H), 3.93 (s, 2H), 3.84 (m, 1H), 3.41 (t, 2H), 3.22-3.10 (m, 7H), 2.96 (t, 2H), 2.91 (t, 2H), 2.83 (m, 1H), 2.27 (s, 3H), 2.18-2.03 (m, 7H), 1.93-1.80 (m, 3H), 1.70 (m, 2H), 1.50 (m, 1H), 1.41-1.17 (m, 6H); EI-MS: 632.5 (M+1).

Preparation of Compound 42

Compound 42 was prepared in a manner similar to that used to prepare compound 39. $^1$H NMR (400 MHz, D$_2$O) δ 7.71 (s, 1H), 5.92 (s, 1H), 4.74 (d, 1H), 4.67 (d, 1H), 4.27 (m, 1H), 4.02 (m, 1H), 3.93 (m, 1H), 3.91 (s, 2H), 3.42 (m, 2H), 3.26-3.04 (m, 7H), 2.97 (m, 2H), 2.90 (m, 1H), 2.63 (t, 2H), 2.27 (s, 3H), 2.19-1.78 (m, 11H), 1.69 (m, 1H), 1.53 (m, 1H), 1.42-1.17 (m, 6H); EI-MS: 614.5 (M+1).

Preparation of Compound 43

Compound 43 was prepared in a manner similar to that used to prepare compound 39. $^1$H NMR (400 MHz, D$_2$O) δ 5.93 (s, 1H), 4.80 (d, 1H), 4.73 (d, 1H), 4.29 (m, 1H), 4.08 (m, 1H), 3.89 (m, 1H), 3.87 (s, 2H), 3.41 (t, 2H), 3.30-3.10 (m, 9H), 2.98 (t, 2H), 2.91 (m, 1H), 2.27 (s, 3H), 2.25-2.04 (m, 7H), 1.98-1.78 (m, 4H), 1.68 (m, 1H), 1.54 (m, 1H), 1.41-1.17 (m, 6H); EI-MS: 615.5 (M+1).

Preparation of Compound 44

Compound 44 was prepared in a manner similar to that used to prepare compound 39. $^1$H NMR (400 MHz, D$_2$O) δ 5.98 (s, 1H), 4.38-4.20 (m, 4H), 3.92 (m, 1H), 3.84 (s, 2H), 3.42 (t, 2H), 3.38-3.16 (m, 7H), 3.06 (m, 1H), 2.99 (t, 2H), 2.51 (t, 2H), 2.29 (s, 3H), 2.22-2.01 (m, 7H), 1.97-1.81 (m, 3H), 1.70 (m, 1H), 1.62-1.43 (m, 2H), 1.41-1.17 (m, 6H); EI-MS: 615.5 (M+1).

Preparation of Compound 45

Compound 45 was prepared in a manner similar to that used to prepare compound 39. $^1$H NMR (400 MHz, D$_2$O) δ 5.94 (s, 1H), 5.04 (d, 1H), 4.95 (d, 1H), 4.28 (m, 1H), 4.02 (m, 1H), 3.96-3.84 (m, 3H), 3.41 (t, 2H), 3.28-3.16 (m, 9H), 2.98 (t, 2H), 2.83 (m, 1H), 2.27 (s, 3H), 2.24-2.04 (m, 7H), 1.92-1.80 (m, 3H), 1.70 (m, 2H), 1.51 (m, 1H), 1.41-1.17 (m, 6H); EI-MS: 631.5 (M+1).

Preparation of Compound 46

Compound 46 was prepared in a manner similar to that used to prepare compound 39. $^1$H NMR (400 MHz, D$_2$O) δ 5.94 (s, 1H), 4.99 (d, 1H), 4.92 (d, 1H), 4.28 (m, 1H), 4.05 (m, 1H), 3.93 (s, 2H), 3.90 (m, 1H), 3.43 (t, 2H), 3.31-3.15 (m, 9H), 2.99 (t, 2H), 2.92 (m, 1H), 2.47 (m, 2H), 2.28 (s, 3H), 2.19-2.03 (m, 5H), 1.92-1.80 (m, 3H), 1.71 (m, 2H), 1.53 (m, 1H), 1.41-1.17 (m, 6H); EI-MS: 615.5 (M+1).

Preparation of Compound 47

Shown below is a scheme for synthesizing compound 47 via intermediates 47-I-47-III.

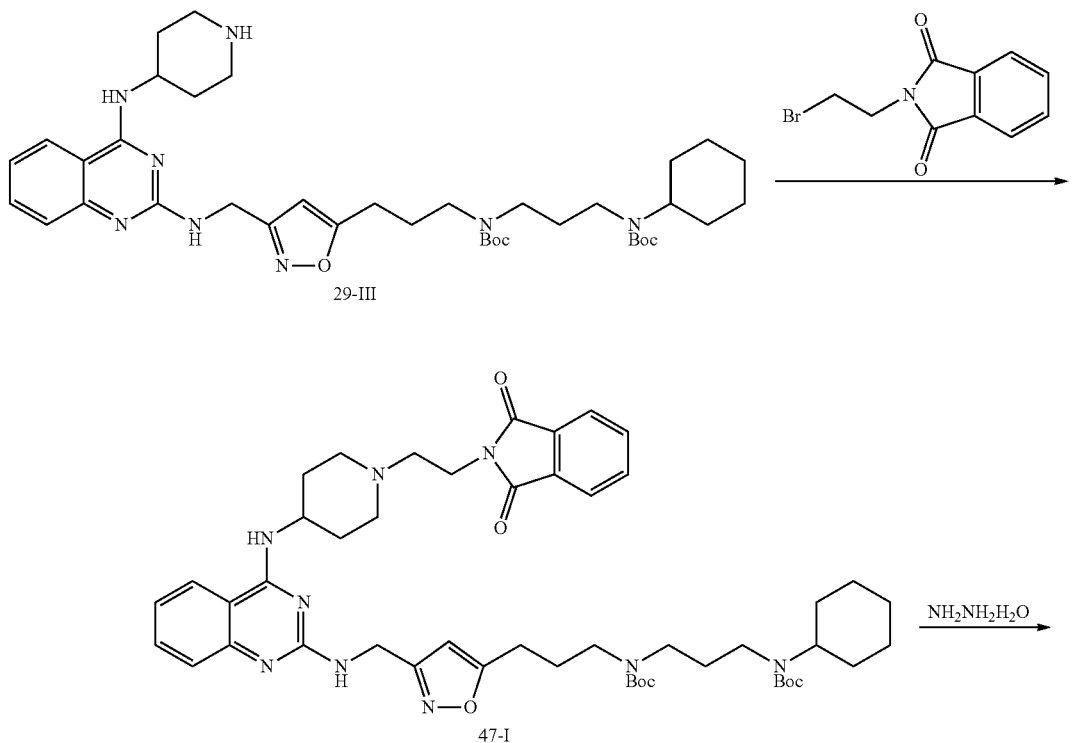

-continued

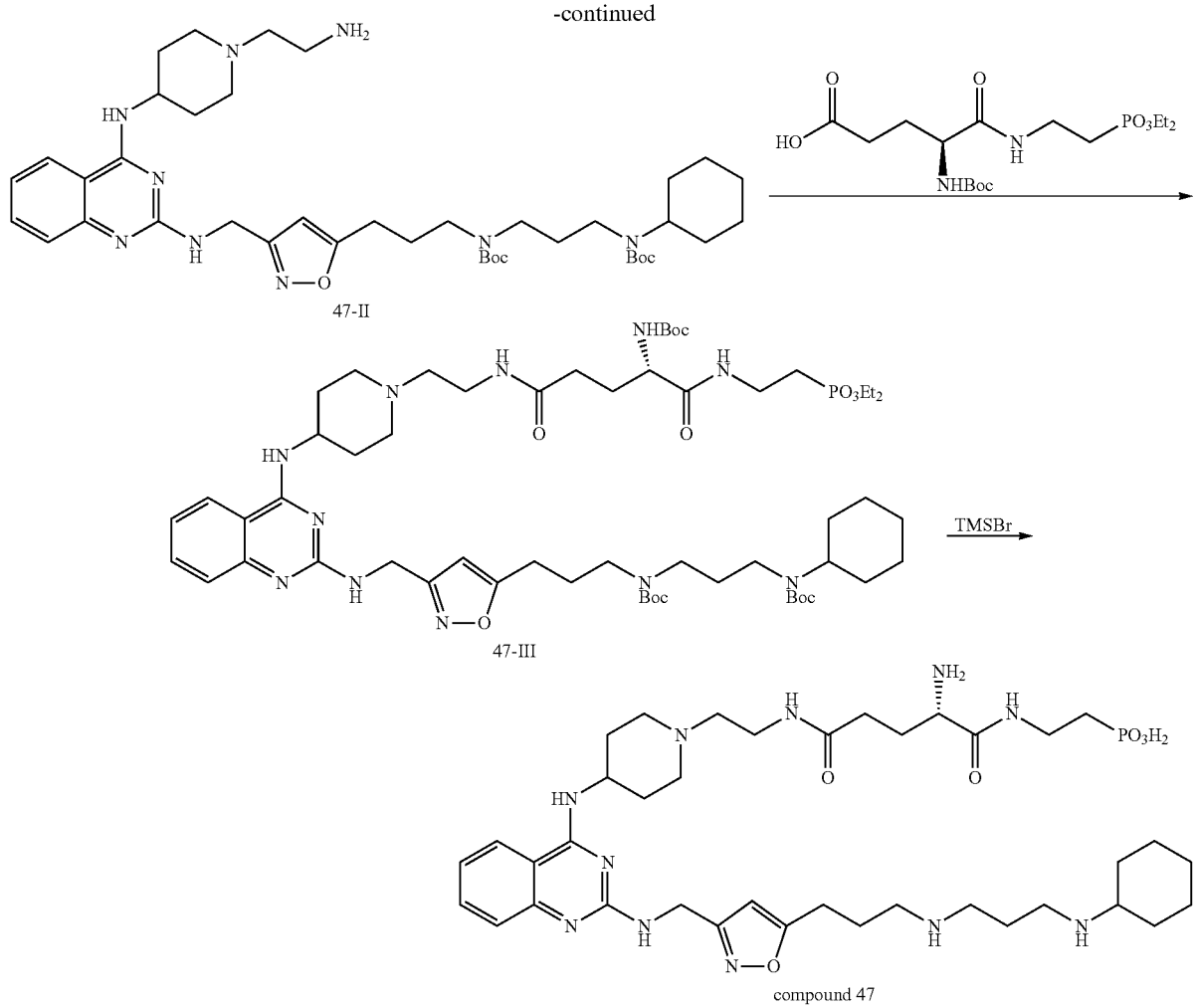

compound 47

To a magnetically stirred solution of compound 29-III (241 mg) and K₂CO₃ (241 mg) in acetonitrile (50 mL) under an atmosphere of nitrogen was added 2-(2-bromo-ethyl)-isoindole-1,3-dione (135 mg). The reaction mixture was stirred at 60° C. for 15 h and then quenched with NH₄Cl(aq) (50 mL, 2 M). The resulting mixture was extracted with dichloromethane (3×100 mL). The combined organic extracts were washed with brine, dried over anhydrous sodium sulfate, filtered, and concentrated. The residue thus obtained was purified by flash chromatography on silica gel with MeOH/DCM (1:19) to afford 47-I (215 mg, y: 72%).

To a stirred solution of compound 47-I (215 mg) in methanol (5 mL) at 5° C. was added 85% NH₂NH₂.H₂O (40 mg) dropwise. The resulting mixture was stirred at 25° C. for 15 h and then concentrated. The residue was poured into K₂CO₃ (aq) (50 mL, 10% w/w) and the mixture was extracted with CH₂Cl₂ (3×100 mL). The combined organic extracts were washed with brine, dried over anhydrous sodium sulfate, filtered, and concentrated. The residue thus obtained was purified by flash chromatography on silica gel with MeOH/NH₄OH (9:1) to afford 47-II (182.3 mg, y: 99%).

To a magnetically stirred solution of 4-tert-Butoxycarbonylamino-4-[2-(diethoxy-phosphoryl)-ethylcarbamoyl]-butyric acid (300.6 mg) in dichloromethane (50 mL) under an atmosphere of nitrogen was added EDCI (91.2 mg) and HOBt (72.9 mg) at 25° C. After the mixture was stirred at 25° C. for 1 h, a solution of compound 47-II (182.3 mg) in dichloromethane (10 mL) was added to the mixture in one portion. The reaction mixture was stirred for another 6 h and then poured into water. The resulting mixture was extracted with dichloromethane (2×50 mL). The combined organic extracts were washed with brine, dried over anhydrous sodium sulfate, filtered, and concentrated. The residue thus obtained was purified by flash chromatography on silica gel with MeOH/DCM (1:19) to give 47-III (241.2 mg, 87% yield).

TMSBr (0.8 mL) was added to the solution of compound 47-III (241.2 mg) in dichloromethane (15 mL). The reaction mixture was stirred at 25° C. for 15 h and concentrated to afford hydrobromide salt of compound 47 (175.3 mg, y: 81%). ¹H NMR (400 MHz, D₂O) δ 7.97 (d, 1H), 7.79 (dd, 1H), 7.42-7.36 (m, 2H), 6.40 (s, 1H), 4.78 (s, 2H), 4.42 (m, 1H), 4.07 (m, 1H), 3.81 (m, 2H), 3.69 (m, 2H), 3.52 (m, 2H), 3.40 (m, 2H), 3.30-3.10 (m, 8H), 2.94 (t, 2H), 2.50 (m, 2H), 2.24-1.93 (m, 14H), 1.85 (m, 2H), 1.68 (m, 1H), 1.41-1.17 (m, 6H); EI-MS: 800.5 (M+1).

Preparation of Compound 48

Compound 48 was prepared in a manner similar to that used to prepare compound 47. ¹H NMR (400 MHz, D₂O) δ 8.02 (d, 1H), 7.84 (s, 1H), 7.80 (dd, 1H), 7.48-7.40 (m, 2H), 4.68 (s, 2H), 4.59 (m, 1H), 4.05 (m, 1H), 3.82 (m, 2H), 3.67

(m, 2H), 3.52 (m, 2H), 3.38 (m, 2H), 3.31-3.14 (m, 8H), 2.97 (t, 2H), 2.50 (m, 2H), 2.39 (m, 2H), 2.23-2.01 (m, 12H), 1.85 (m, 2H), 1.68 (m, 1H), 1.41-1.17 (m, 6H); EI-MS: 800.5 (M+1).

Preparation of Compound 49

Compound 49 was prepared in a manner similar to that used to prepare compound 47. $^1$H NMR (400 MHz, D$_2$O) δ 8.02 (d, 1H), 7.81 (dd, 1H), 7.48-7.40 (m, 2H), 7.24 (s, 1H), 5.01 (s, 2H), 4.42 (m, 1H), 3.99 (m, 1H), 3.69 (m, 2H), 3.65 (m, 2H), 3.54 (m, 1H), 3.45 (m, 1H), 3.34 (m, 2H), 3.20-3.04 (m, 8H), 2.87 (t, 2H), 2.47 (m, 2H), 2.24-1.97 (m, 12H), 1.92-1.80 (m, 4H), 1.68 (m, 1H), 1.41-1.17 (m, 6H); EI-MS: 816.5 (M+1).

Preparation of Compound 50

Compound 50 was prepared in a manner similar to that used to prepare compound 47. $^1$H NMR (400 MHz, D$_2$O) δ 8.00 (d, 1H), 7.80 (dd, 1H), 7.75 (s, 1H), 7.46-7.40 (m, 2H), 4.82 (s, 2H), 4.40 (m, 1H), 4.01 (m, 1H), 3.73 (m, 2H), 3.67 (m, 2H), 3.54 (m, 1H), 3.43 (m, 1H), 3.38 (m, 2H), 3.22-3.08 (m, 8H), 2.62 (t, 2H), 2.48 (m, 2H), 2.25-1.96 (m, 14H), 1.84 (m, 2H), 1.68 (m, 1H), 1.41-1.17 (m, 6H); EI-MS: 800.6 (M+1).

Preparation of Compound 51

Compound 51 was prepared in a manner similar to that used to prepare compound 47. $^1$H NMR (400 MHz, D$_2$O) δ 8.07 (d, 1H), 7.87 (dd, 1H), 7.54-7.46 (m, 2H), 5.01 (s, 2H), 4.39 (m, 1H), 4.05 (m, 1H), 3.84 (m, 2H), 3.69 (m, 2H), 3.51 (m, 2H), 3.41 (m, 2H), 3.36-3.02 (m, 10H), 2.51 (m, 2H), 2.32-1.96 (m, 14H), 1.87 (m, 2H), 1.69 (m, 1H), 1.41-1.17 (m, 6H); EI-MS: 801.6 (M+1).

Preparation of Compound 52

Compound 52 was prepared in a manner similar to that used to prepare compound 47. $^1$H NMR (400 MHz, D$_2$O) δ 8.07 (d, 1H), 7.86 (dd, 1H), 7.55-7.43 (m, 2H), 5.17 (s, 2H), 4.69 (t, 2H), 4.46 (m, 1H), 4.06 (m, 1H), 3.82 (m, 2H), 3.69 (m, 2H), 3.56-3.12 (m, 12H), 2.53-2.38 (m, 4H), 2.32-1.80 (m, 14H), 1.69 (m, 1H), 1.41-1.17 (m, 6H); EI-MS: 801.6 (M+1).

Preparation of Compound 53

Compound 53 was prepared in a manner similar to that used to prepare compound 1. EI-MS: 523.5 (M+1).

Preparation of Compound 54

Compound 54 was prepared in a manner similar to that used to prepare compound 29. $^1$H NMR (400 MHz, D$_2$O) δ 8.02 (d, 1H), 7.83 (t, 1H), 7.75 (s, 1H), 7.50-7.42 (m, 2H), 4.82 (s, 2H), 4.47 (m, 1H), 4.40-4.24 (m, 2H), 4.06 (m, 1H), 3.25 (m, 1H), 3.20-3.04 (m, 6H), 2.80 (m, 1H), 2.70-2.60 (m, 4H), 2.20-1.78 (m, 9H), 1.92-1.80 (m, 3H), 1.71 (m, 2H), 1.53 (m, 1H), 1.40-1.17 (m, 6H); EI-MS: 651.5 (M+1).

Preparation of Compound 55

Shown below is a scheme for synthesizing compound 55 via intermediates 55-I-55-III.

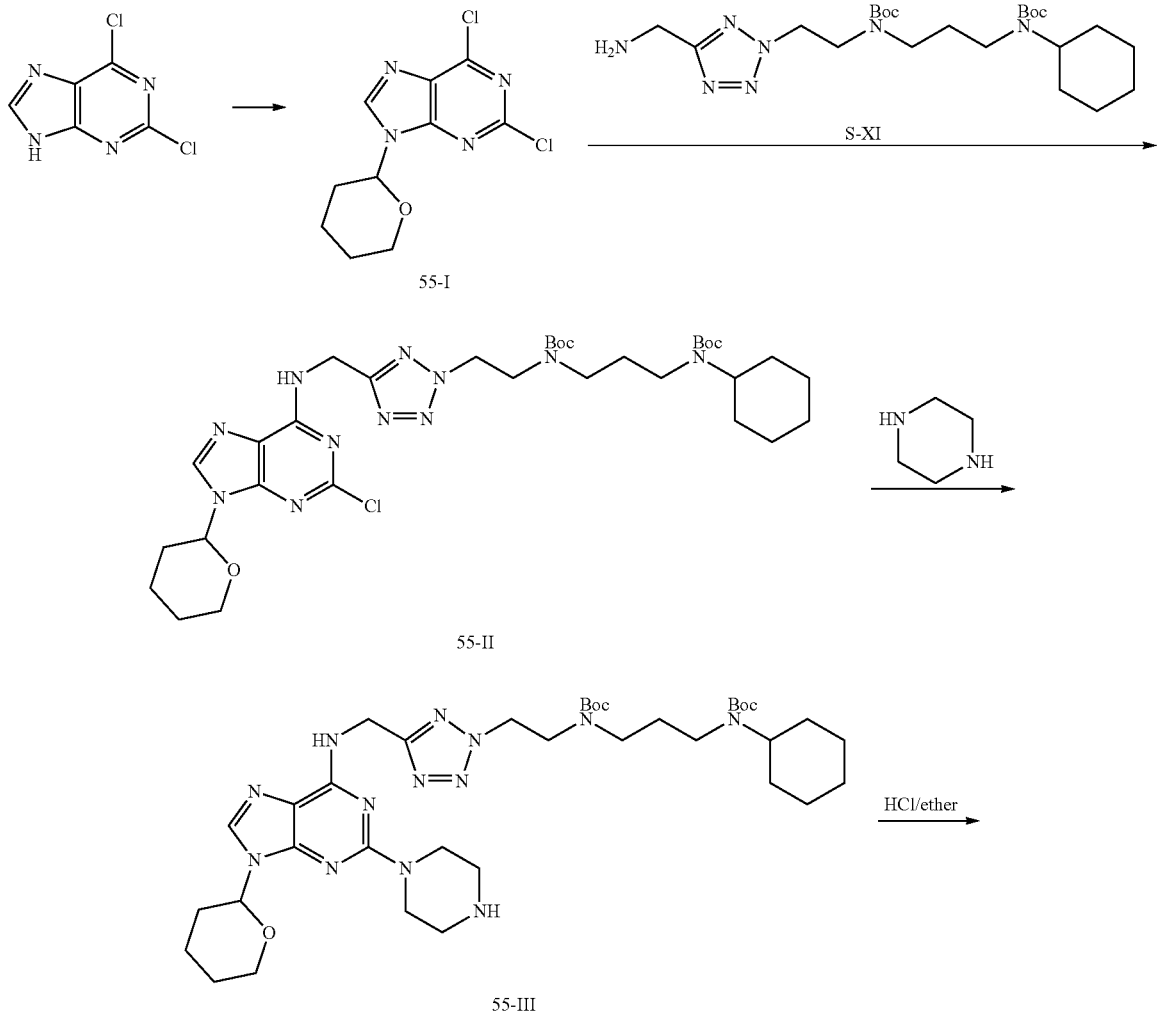

-continued

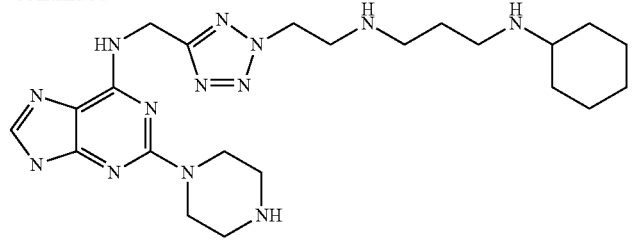

compound 55

To a magnetically stirred solution of 2,6-dichloropurine (10 g) in ethyl acetate (100 mL) was added p-toluenesulfonic acid monohydrate (0.08 g). The resultant mixture was heated to 50° C. under an atmosphere of nitrogen and 3,4-dihydro-2H-pyran (7.5 mL) was added over a period of 2 h. The mixture was stirred at 25° C. for 15 h and filtrated to give crude solid. The solid was washed with n-hexane/ethyl acetate (1:1) to afford compound 55-I (14.4 g, y: 100%)

To a magnetically stirred solution of compound 55-I (0.65 g) in ethyl acetate (35 mL) under an atmosphere of nitrogen was added compound S-XI (1.15 g) and TEA (0.75 g). The mixture was heated to 50° C. for 4 h, cooled down to 25° C., and then quenched with aqueous NH$_4$Cl (50 mL, 2 M). The resulting solution was extracted with ethyl acetate (3×100 mL). The combined extracts were washed with brine, dried over anhydrous sodium sulfate, filtered, and concentrated. The residue thus obtained was purified by flash chromatography on silica gel with MeOH/DCM (1:9) to afford compound 55-II (1.16 g, y: 68%) as a light yellow solid.

A solution of compound 55-II (1.05 g) and piperazine (1.00 g) in 1-pentanol (6 mL) was heated at 100° C. for 15 h, and then concentrated. The residue thus obtained was purified with flash chromatography on silica gel with MeOH/DCM (1:1) to afford compound 55-III (0.67 g, y: 60%).

A solution of 1N HCl/diethyl ether (5.3 mL) was added to the solution of compound 55-III (264 mg) in dichloromethane (10.6 mL). The reaction mixture was stirred for 15 h and concentrated to afford hydrochloride salt of compound 55 (204 mg, 94% yield). EI-MS: 498.5 (M+1).

Preparation of Compound 56

Compound 56 was prepared in a manner similar to that used to prepare compound 1. EI-MS: 528.5 (M+1).

Preparation of Compound 57

Compound 57 was prepared in a manner similar to that used to prepare compound 15. EI-MS: 473.5 (M+1).

Preparation of Compound 58

Compound 58 was prepared in a manner similar to that used to prepare compound 15. EI-MS: 472.5 (M+1).

Preparation of Compound 59

Compound 59 was prepared in a manner similar to that used to prepare compound 39. $^1$H NMR (400 MHz, D$_2$O) δ 8.02 (d, 1H), 7.83 (t, 1H), 7.46-7.41 (m, 2H), 5.10 (d, 1H), 5.02 (m, 1H), 4.47 (m, 1H), 4.36 (m, 1H), 4.05 (m, 1H), 3.95 (s, 2H), 3.34-3.12 (m, 9H), 2.84 (m, 1H), 2.69 (t, 2H), 2.58 (t, 2H), 2.47 (m, 2H), 2.17-2.00 (m, 7H), 1.94-1.80 (m, 3H), 1.71 (m, 2H), 1.51 (m, 1H), 1.41-1.17 (m, 6H); EI-MS: 665.6 (M+1).

Preparation of Compound 60

Compound 60 was prepared in a manner similar to that used to prepare compound 29. EI-MS: 767.6 (M+1).

Preparation of Compound 61

Compound 61 was prepared in a manner similar to that used to prepare compound 39. $^1$H NMR (400 MHz, D$_2$O) δ 8.03 (d, 1H), 7.84 (t, 1H), 7.51-7.45 (m, 2H), 5.11 (d, 1H), 5.02 (d, 1H), 4.48 (m, 1H), 4.28 (m, 1H), 4.01-3.83 (m, 3H), 3.45 (t, 2H), 3.31-3.11 (m, 7H), 3.02 (t, 2H), 2.95-2.81 (m, 3H), 2.48 (m, 2H), 2.15-1.97 (m, 5H), 1.92-1.81 (m, 3H), 1.71 (m, 2H), 1.57 (m, 1H), 1.41-1.17 (m, 6H); EI-MS: 651.5 (M+1).

Preparation of Compound 62

Compound 62 was prepared in a manner similar to that used to prepare compound 39. $^1$H NMR (400 MHz, D$_2$O) δ 5.93 (s, 1H), 4.99 (d, 1H), 4.92 (d, 1H), 4.28 (m, 1H), 4.05 (m, 1H), 3.96 (m, 1H), 3.87 (s, 2H), 3.34-3.14 (m, 11H), 2.90 (m, 1H), 2.66 (t, 2H), 2.47 (m, 2H), 2.28 (s, 3H), 2.19-2.00 (m, 7H), 1.94-1.81 (m, 3H), 1.71 (m, 2H), 1.51 (m, 1H), 1.41-1.17 (m, 6H); EI-MS: 629.5 (M+1).

Preparation of Compound 63

Compound 63 was prepared in a manner similar to that used to prepare compound 39. $^1$H NMR (400 MHz, D$_2$O) δ 5.95 (s, 1H), 4.98 (d, 1H), 4.91 (d, 1H), 4.29 (m, 1H), 4.04 (m, 1H), 3.98-3.86 (m, 3H), 3.43 (t, 2H), 3.38-3.18 (m, 9H), 2.99 (t, 2H), 2.92 (m, 1H), 2.59 (q, 2H), 2.46 (m, 2H), 2.32-1.64 (m, 10H), 1.52 (m, 1H), 1.41-1.17 (m, 9H); EI-MS: 629.5 (M+1).

Preparation of Compound 64

Compound 64 was prepared in a manner similar to that used to prepare compound 39. $^1$H NMR (400 MHz, D$_2$O) δ 5.94 (s, 1H), 4.99 (d, 1H), 4.92 (d, 1H), 4.28 (m, 1H), 4.05 (m, 1H), 3.99-3.84 (m, 3H), 3.34-3.14 (m, 11H), 2.89 (m, 1H), 2.65 (t, 2H), 2.58 (q, 2H), 2.46 (m, 2H), 2.19-2.00 (m, 7H), 1.94-1.81 (m, 3H), 1.70 (m, 2H), 1.51 (m, 1H), 1.41-1.17 (m, 9H); EI-MS: 643.6 (M+1).

Preparation of Compound 65

Compound 65 was prepared in a manner similar to that used to prepare compound 29. $^1$H NMR (400 MHz, D$_2$O) δ 5.94 (s, 1H), 4.98 (d, 1H), 4.93 (d, 1H), 4.29 (m, 1H), 4.12-4.01 (m, 2H), 3.93 (m, 1H), 3.30-3.14 (m, 9H), 2.90 (m, 1H), 2.72 (m, 2H), 2.58 (q, 2H), 2.46 (m, 2H), 2.26-2.05 (m, 7H), 1.92-1.82 (m, 3H), 1.69 (m, 2H), 1.51 (m, 1H), 1.40-1.17 (m, 9H); EI-MS: 629.5 (M+1).

Preparation of Compound 66

Compound 66 was prepared in a manner similar to that used to prepare compound 29. $^1$H NMR (400 MHz, D$_2$O) δ 5.94 (s, 1H), 4.82 (s, 2H), 4.28 (m, 1H), 4.10-3.83 (m, 3H), 3.18-3.12 (m, 7H), 2.95 (m, 2H), 2.83 (m, 1H), 2.71 (m, 2H), 2.58 (q, 2H), 2.26-2.04 (m, 9H), 1.94-1.78 (m, 3H), 1.69 (m, 2H), 1.50 (m, 1H), 1.40-1.17 (m, 9H); EI-MS: 628.5 (M+1).

Preparation of Compound 67

Compound 67 was prepared in a manner similar to that used to prepare compound 29. $^1$H NMR (400 MHz, D$_2$O) δ 8.04 (d, 1H), 7.86 (t, 1H), 7.51-7.43 (m, 2H), 5.12 (s, 2H), 4.70 (t, 2H), 4.47 (m, 1H), 4.27 (m, 1H), 4.12-4.01 (m, 2H), 3.31-3.13 (m, 7H), 2.86 (m, 1H), 2.75 (m, 2H), 2.43 (m, 2H), 2.28 (m, 2H), 2.17-2.04 (m, 4H), 1.95-1.80 (m, 4H), 1.71 (m, 2H), 1.57 (m, 1H), 1.40-1.17 (m, 6H); EI-MS: 651.5 (M+1).

Preparation of Compound 68

Compound 68 was prepared in a manner similar to that used to prepare compound 39. $^1$H NMR (400 MHz, D$_2$O) δ 8.04 (d, 1H), 7.84 (t, 1H), 7.51-7.42 (m, 2H), 5.15 (s, 2H), 4.69 (t, 2H), 4.49 (m, 1H), 4.30 (m, 1H), 4.01-3.90 (m, 3H), 3.44 (t, 2H), 3.36-3.13 (m, 7H), 3.02 (t, 2H), 2.90 (m, 1H), 2.43 (m, 2H), 2.18-2.05 (m, 4H), 1.94-1.81 (m, 4H), 1.71 (m, 2H), 1.58 (m, 1H), 1.41-1.17 (m, 6H); EI-MS: 651.5 (M+1).

Preparation of Compound 69

Compound 69 was prepared in a manner similar to that used to prepare compound 29. $^1$H NMR (400 MHz, D$_2$O) δ 5.95 (s, 1H), 5.02 (d, 1H), 5.00 (d, 1H), 4.31 (m, 1H), 4.09-3.86 (m, 3H), 3.30-3.12 (m, 9H), 2.85 (m, 1H), 2.70 (m, 2H), 2.58 (q, 2H), 2.28-2.05 (m, 9H), 1.92-1.80 (m, 3H), 1.70 (m, 2H), 1.50 (m, 1H), 1.40-1.17 (m, 9H); EI-MS: 645.5 (M+1).

Preparation of Compound 70

Compound 70 was prepared in a manner similar to that used to prepare compound 39. $^1$H NMR (400 MHz, D$_2$O) δ 5.96 (s, 1H), 5.05 (d, 1H), 4.97 (d, 1H), 4.29 (m, 1H), 4.03 (m, 1H), 3.98-3.84 (m, 3H), 3.43 (t, 2H), 3.32-3.13 (m, 9H), 2.99 (t, 2H), 2.86 (m, 1H), 2.58 (q, 2H), 2.28-2.04 (m, 7H), 1.92-1.80 (m, 3H), 1.71 (m, 2H), 1.52 (m, 1H), 1.41-1.17 (m, 9H); EI-MS: 645.5 (M+1).

Preparation of Compound 71

Compound 71 was prepared in a manner similar to that used to prepare compound 15. $^1$H NMR (300 MHz, D$_2$O) δ 8.67 (s, 1H), 5.94 (s, 1H), 4.76 (s, 2H), 4.36 (t, 2H), 4.10 (m, 1H), 3.44 (m, 2H), 3.21-3.02 (m, 8H), 2.32 (m, 2H), 2.26 (s, 3H), 2.19-1.98 (m, 6H), 1.84 (m, 2H), 1.79-1.60 (m, 3H), 1.42-1.16 (m, 6H); EI-MS: 485.6 (M+1).

Preparation of Compound 72

Compound 72 was prepared in a manner similar to that used to prepare compound 1. EI-MS: 492.6 (M+1).

Preparation of Compound 73

Compound 73 was prepared in a manner similar to that used to prepare compound 15. $^1$H NMR (300 MHz, D$_2$O) δ 7.66 (s, 1H), 6.01 (s, 1H), 4.97 (s, 2H), 4.41 (s, 2H), 4.05 (m, 1H), 3.45 (m, 2H), 3.28-3.03 (m, 6H), 2.29 (s, 3H), 2.18-1.96 (m, 6H), 1.86 (m, 2H), 1.79-1.60 (m, 3H), 1.41-1.18 (m, 6H); EI-MS: 456.6 (M+1).

Preparation of Compound 74

Compound 74 was prepared in a manner similar to that used to prepare compound 15. $^1$H NMR (300 MHz, D$_2$O) δ 8.21 (s, 1H), 5.05 (s, 2H), 4.08 (m, 1H), 3.49 (m, 2H), 3.21-3.06 (m, 10H), 2.43 (m, 2H), 2.19-2.00 (m, 7H), 1.90-1.62 (m, 7H), 1.42-1.16 (m, 6H); EI-MS: 540.7 (M+1).

Preparation of Compound 75

Compound 75 was prepared in a manner similar to that used to prepare compound 15. EI-MS: 486.6 (M+1).

Preparation of Compound 76

Compound 76 was prepared in a manner similar to that used to prepare compound 29. $^1$H NMR (300 MHz, D$_2$O) δ 7.94 (d, 1H), 7.76 (t, 1H), 7.42-7.36 (m, 2H), 6.52 (s, 1H), 4.81 (s, 2H), 4.41 (m, 1H), 4.27 (m, 1H), 4.08 (m, 1H), 3.99 (m, 1H), 3.22-3.06 (m, 7H), 2.86 (t, 2H), 2.80-2.66 (m, 3H), 2.22 (m, 2H), 2.16-2.00 (m, 6H), 1.99-1.59 (m, 4H), 1.66 (m, 2H), 1.49 (m, 1H), 1.39-1.15 (m, 6H); EI-MS: 649.6 (M+1).

Preparation of Compound 77

Compound 77 was prepared in a manner similar to that used to prepare compound 29. $^1$H NMR (300 MHz, D$_2$O) δ 8.65 (s, 1H), 7.93 (d, 1H), 7.76 (t, 1H), 7.41-7.34 (m, 2H), 4.80 (m, 2H), 4.44 (m, 1H), 4.37 (t, 2H), 4.25 (m, 1H), 4.11 (m, 1H), 3.99 (m, 1H), 3.25-3.02 (m, 7H), 2.77 (m, 1H), 2.73 (m, 2H), 2.31-2.20 (m, 4H), 2.17-2.01 (m, 4H), 2.00-1.80 (m, 4H), 1.68 (m, 2H), 1.57 (m, 1H), 1.40-1.17 (m, 6H); EI-MS: 650.6 (M+1).

Preparation of Compound 78

Compound 78 was prepared in a manner similar to that used to prepare compound 39. $^1$H NMR (300 MHz, D$_2$O) δ 7.93 (d, 1H), 7.77 (t, 1H), 7.41-7.35 (m, 2H), 5.05 (d, 1H), 4.97 (d, 1H), 4.43 (m, 1H), 4.29 (m, 1H), 4.19 (m, 1H), 3.90 (m, 1H), 3.58 (m, 2H), 3.31-3.06 (m, 9H), 2.98 (m, 2H), 2.81 (m, 1H), 2.55-2.38 (m, 4H), 2.22-1.77 (m, 12H), 1.71 (m, 2H), 1.57 (m, 1H), 1.41-1.17 (m, 6H); EI-MS: 691.6 (M+1).

Preparation of Compound 79

Compound 79 was prepared in a manner similar to that used to prepare compound 29. $^1$H NMR (300 MHz, D$_2$O) δ 8.02 (d, 1H), 7.83 (t, 1H), 7.76 (s, 1H), 7.50-7.42 (m, 2H), 5.09 (m, 2H), 4.44 (s, 2H), 4.40 (m, 1H), 4.23 (m, 1H), 4.08-3.99 (m, 2H), 3.23-3.04 (m, 5H), 2.78-2.73 (m, 3H), 2.22 (m, 2H), 2.18-2.00 (m, 4H), 1.94-1.70 (m, 4H), 1.64 (m, 2H), 1.53 (m, 1H), 1.40-1.17 (m, 6H); EI-MS: 621.7 (M+1).

Preparation of Compound 80

Compound 80 was prepared in a manner similar to that used to prepare compound 39. $^1$H NMR (300 MHz, D$_2$O) δ 7.92 (d, 1H), 7.74 (t, 1H), 7.41-7.35 (m, 2H), 5.00 (m, 2H), 4.43 (m, 1H), 4.29 (m, 1H), 4.02-3.95 (m, 2H), 3.42 (m, 2H), 3.31-3.06 (m, 9H), 2.99 (m, 2H), 2.81 (m, 1H), 2.42 (m, 2H), 2.14-2.00 (m, 5H), 1.98-1.60 (m, 8H), 1.53 (m, 1H), 1.41-1.17 (m, 6H), 0.99 (d, 6H); EI-MS: 707.7 (M+1).

Preparation of Compound 81

Compound 81 was prepared in a manner similar to that used to prepare compound 39. $^1$H NMR (300 MHz, D$_2$O) δ 8.76 (s, 1H), 5.91 (s, 1H), 4.77 (m, 2H), 4.39 (t, 2H), 4.22 (m, 1H), 4.05 (m, 1H), 3.99 (s, 2H), 3.84 (m, 1H), 3.43 (t, 2H), 3.24-3.08 (m, 7H), 2.97 (t, 2H), 2.87 (m, 1H), 2.31 (m, 2H), 2.25 (s, 3H), 2.19-2.03 (m, 5H), 1.92-1.61 (m, 5H), 1.53 (m, 1H), 1.41-1.17 (m, 6H); EI-MS: 614.6 (M+1).

Preparation of Compound 82

Compound 82 was prepared in a manner similar to that used to prepare compound 39. EI-MS: 641.7 (M+1).

Preparation of Compound 83

Compound 83 was prepared in a manner similar to that used to prepare compound 39. EI-MS: 585.6 (M+1).

Preparation of Compound 84

Compound 84 was prepared in a manner similar to that used to prepare compound 47. EI-MS: 788.6 (M+1).

Preparation of Compound 85

Compound 85 was prepared in a manner similar to that used to prepare compound 39. $^1$H NMR (300 MHz, D$_2$O) δ 7.45 (s, 1H), 4.92 (m, 2H), 4.40 (m, 1H), 4.16 (m, 1H), 3.95 (s, 2H), 3.91 (m, 1H), 3.42 (t, 2H), 3.25-3.10 (m, 9H), 2.99 (t, 2H), 2.76 (m, 1H), 2.44 (m, 2H), 2.19-2.03 (m, 4H), 1.96 (s, 3H), 1.92-1.61 (m, 6H), 1.53 (m, 1H), 1.41-1.17 (m, 6H); EI-MS: 615.6 (M+1).

Preparation of Compound 86

Compound 86 was prepared in a manner similar to that used to prepare compound 29. $^1$H NMR (300 MHz, D$_2$O) δ 7.44 (s, 1H), 4.92 (m, 2H), 4.40 (m, 1H), 4.21 (m, 1H), 4.06 (m, 1H), 3.96 (m, 1H), 3.26-3.10 (m, 9H), 2.80-2.64 (m, 3H), 2.41 (m, 2H), 2.22 (m, 2H), 2.16-2.02 (m, 4H), 1.95 (s, 3H), 1.90-1.60 (m, 6H), 1.51 (m, 1H), 1.40-1.17 (m, 6H); EI-MS: 615.6 (M+1).

EXAMPLE 2

Inhibition of Radioligand Binding in Human CXCR4-Transfected HEK293 Cells

Binding competition between the compounds of Formula (I) and human CXCL12 was assessed using a radioligand binding assay as described below.

Membranes (2-4 µg) prepared from human CXCR4-transfected HEK293 cells in 40 µL of assay buffer (50 mM HEPES-NaOH, pH 7.4, 100 mM NaCl, 5 mM $MgCl_2$, 1 mM $CaCl_2$, 0.5% bovine serum albumin) were incubated with 20 µL of radio-labeled $^{125}$I-CXCL12 (0.16 nM) and 20 µL of a test compound in an assay plate (Costar Corning, Cambridge, Mass.). After 60 minutes at 30° C., the incubation was terminated by transferring the resulting reaction mixture to a 96-well GF/B filter plate (Millipore Corp., Billerica, Mass.) and filtered via a manifold. The plate was washed with 100 µL of ice-cold wash buffer (50 mM HEPES-NaOH, pH 7.4, 100 mM NaCl) four times. The radioactivity bound to the filter was measured by Topcount (PerkinElmer Inc., Waltham, Mass.).

It was unexpectedly observed that the concentration required to inhibit binding of $^{125}$I-CXCL12 to CXCR4 by 50% ($IC_{50}$) of 25 tested compounds was lower than 50 nM, 33 tested compounds had $IC_{50}$ values of 50-100 nM, and 28 tested compounds had $IC_{50}$ values of 100-1000 nM. More specifically, the list of compounds showing $IC_{50}$ values lower than 50 nM includes Compounds 1-7, 9, 12, 13, 15-19, 21, 23, 25, 28-30, 40, 42, 59, and 75; the list of compounds showing $IC_{50}$ values of 50-100 nM includes Compounds 8, 10, 11, 14, 20, 22, 24, 26, 27, 31-35, 37-39, 43, 45-50, 58, 61, 62, 66, 72, 73, 76, 78, and 82; and the list of compounds showing $IC_{50}$ values of 100-1000 nM includes Compounds 36, 41, 44, 51-57, 60, 63-65, 67-71, 74, 77, 79-81 and 83-86.

These results indicate that compounds of Formula (I) have high binding affinities toward CXCR4.

EXAMPLE 3

Inhibition of Chemotaxis in Lymphoblastic Leukemia Cells

The response of cancer cells to compounds of Formula (I) was evaluated using the chemotaxis assay as set forth below.

T-cell acute lymphoblastic leukemia (CCRF-CEM) cells in Roswell Park Memorial Institute medium (RPMI) 1640 supplemented with 10% bovine serum albumin were incubated with 250 µL of a test compound. The assay was performed using Millicell Hanging Cell Culture Inserts (pore size 5 µm; 24-well plate; Millipore, Bedford, Mass., USA). After 10 minutes at 37° C., 250 µL of cells preincubated with a test compound were plated per well in the upper chambers of the inserts at a density of $2.5 \times 10^5$ cells/well. 300 µL/well medium containing CXCL12 (10 nM) and a test compound were plated in the lower chamber of the insert. After 2.5 h at 37° C., cells in both chambers of inserts were measured by flow cytometry (Guava Technologies, Hayward, Calif., USA).

It was observed that 39 tested compounds unexpectedly showed concentrations required to inhibit chemotaxis by 50% ($EC_{50}$) with values of lower than 50 nM and 4 tested compounds showed $EC_{50}$ values of 50-150 nM. More specifically, the list of compounds showing $EC_{50}$ values lower than 50 nM includes Compounds 1-8, 10, 13-18, 20-24, 26, 29-32, 35, 37-42, 45, 47-49, 59, 61, and 62; and the list of compounds showing $EC_{50}$ values of 50-150 nM includes Compounds 33, 34, 46, and 50.

These results indicate that compounds of Formula (I) have high efficacy in inhibiting the chemotaxis of certain cancer cells.

EXAMPLE 4

Effect on Mobilization of Stem Cells in Mice 38 compounds of Formula (I) were tested to assess their efficacy in enhancing stem/progenitor cell mobilization as follows. The list of these 38 compounds includes Compounds 1-3, 13, 15, 17, 24, 26, 29-31, 33, 35, 36, 38-43, 45, 46, 49, 50, 54, 59-68, 76, 78, and 83.

Each of the 38 compounds was dissolved in saline to form a solution. The solution was administered to C57BL/6 male mice (National Laboratory Animal Center, Taipei, Taiwan) subcutaneously. Mice treated with saline were used as controls. Whole blood was collected 2 h after subcutaneous injection and labeled with the following antibodies: (i) APC-conjugated anti-CXCR4 (clone 2B11; eBioscience), (ii) FITC-conjugated anti-CD34 (clone RAM34; eBioscience), (iii) PE-conjugated anti-CD133 (clone 13A4; eBioscience), (iv) anti-c-kit (clone 2B8; eBioscience), (v) anti-Sca-1 (clone D7; eBioscience), (vi) anti-linage (Mouse Hematopoietic Lineage Biotin Panel, eBioscience), and (vii) Streptavidin PE-Cy7 (eBioscience). Hematopoietic stem cells ($CD34^+$) and endothelial progenitor cells ($CD133^+$) were quantified using antibody surface staining and flow cytometry (Guava Technologies, Hayward, Calif., USA).

Unexpectedly, these 38 compounds significantly enhanced mobilization of $CD34^+$ hematopoietic stem cells (up to 3.7 folds) and $CD133^+$ endothelial progenitor cells (up to 4.5 folds) into peripheral blood as compared to saline controls. In addition, 4 tested compounds, i.e., Compounds 40, 45, 49, and 50, combined with G-CSF were found to unexpectedly mobilize hematopoietic stem cells synergistically as evidenced by the significant increase of CFU-GM numbers.

These results indicate that compounds of Formula (I) have high efficacy in enhancing stem/progenitor cell mobilization.

EXAMPLE 5

Treatment of Ischemia-Reperfusion Injury of Kidney in Rats

The efficacy of five compounds of Formula (I) in treating Ischemia-Reperfusion injury was assessed using both an acute kidney injury model, an ischemic stroke model, and a limb ischemia model. These five compounds are Compounds 13, 35, 40, 45, and 46.

In an acute Kidney Injury (AKI) model, each of the five compounds was dissolved in saline to form a solution. The solution was administered to male Sprague-Dawley rats (National Laboratory Animal Center, Taipei, Taiwan) subcutaneously at a dosage of 6 mg/Kg. 40 minutes after the subcutaneous injection, AKI was induced in the rats by clamping their bilateral renal vein and artery for one hour followed by releasing the vessel clips to allow 24-h reperfusion. Whole blood was collected at 24-h after induction of AKI. Blood urea nitrogen (BUN) and serum creatinine (Scr), two markers that increase upon kidney injury, were measured using a FUJI DRI-CHEM 3500s analyzer (Fujifilm, Tokyo, Japan). Non-AKI rats and AKI rats treated with saline were used as controls.

It was observed that the AKI rats dosed with the tested compounds unexpectedly had levels of BUN and Scr, respectively, 11-25% and 10-56% of those levels induced in saline-treated AKI rats. More specifically, AKI rats dosed with Compounds 13, 35, 40, 45, and 46 had respective BUN levels of 25%, 15%, 20%, 11%, and 22% of those levels induced in saline-treated AKI rats; and had respective Scr levels of 56%, 22%, 36%, 10%, and 22% of those levels induced in saline-treated AKI rats.

These results indicate that compounds of Formula (I) have high efficacy in treating kidney injury.

EXAMPLE 6

Treatment of Hepatocellular Carcinoma (HCC) in Mice

The efficacy of a compound of Formula (I), i.e., Compounds 42, in treating HCC was assessed using a syngeneic mouse model as follows.

C3H mouse-derived HCC cell line HCA-1 was used. HCA-1 cells were orthotopically implanted in C3H mice for 10 days. The mice were subsequently treated with sorafenib (a small molecule drug for treating hepatocellular carcinoma; 40 mg/kg) daily for two weeks or treated with vehicle (PBS) alone as a control. Tested compounds, e.g., AMD3100 (10 mg/kg/day) and Compound 42 (10 mg/kg/day), were each administered continuously to those mice treated with sorafenib using an Alzet osmotic pump (DURECT Corporation, Cupertino, Calif.) for two weeks.

It was observed that mice treated with Compound 42 and sorafenib unexpectedly decreased the tumor size from about 400 mm$^3$ (control) to about 50 mm$^3$, as compared to AMD3100 combined with sorafenib, which decreased the tumor size from about 400 mm$^3$ (control) to about 250 mm$^3$. Importantly, no significant body weight loss was observed in animals treated with Compound 42.

These results indicate that Compound 42 has unexpectedly higher efficacy in treating HCC, as compared with AMD3100.

EXAMPLE 7

Treatment of Mild Traumatic Brain Injury in Mice

Traumatic brain injury (TBI), also known as intracranial injury, occurs when an external force injures the brain. It can be classified based on severity, mechanism, or other features (e.g., occurring at a specific location or over a widespread area). TBI results in physical, cognitive, social, emotional, and behavioral symptoms.

The efficacy of a compound of Formula (I), i.e., Compound 42, in treating mild traumatic brain injury (mTBI) was assessed using a mouse mTBI model as follows.

Mild Traumatic Brain Injury (mTBI) Model

Adult CD1 mice were housed in a 12-h dark (7 pm to 7 am) and 12 h light (7 am to 7 pm) cycle. They were anesthetized with isoflurane. mTBI was conducted by dropping a 30 g metal projectile onto the temporal skull, anterior the right ear. Anesthetized mice were laid on their side. A metal tube (13 mm in inner diameter) was placed vertically over the head and a metal projectile was dropped from 80 cm height down the tube to strike the temporal region of the skull anterior to the right ear. The rod-shaped projectile was made of metal with a slightly rounded end in order to enable a smooth contact with the skull without any external damage at the site of the weight drop. A sponge immobilization pad (L: 4-5 in; W: 2.7 in; H: 1.8 in) was employed, allowing head movements during the injury. At around 5-minute after the mTBI, mice were treated with Compound 42 or vehicle (saline). Control (no-mTBI) animals received isoflurane but no mTBI.

Locomotor Behavioral Measurement

At 15-minute and day 5 after the injury and recovery from the anesthesia, mice were individually placed in locomotor activity chambers (Accuscan, Columbus, Ohio) for up to 24 hours (12-h light and 12-h dark/day). Food and water were constantly provided in the chambers, which contained 16 horizontal and 8 vertical infrared sensors spaced 2.5 cm apart. Each mouse was placed in a 42×42×31 cm plexiglass open box. See, e.g., Airavaara et al., J Comp Neurol, 2009, 515:116-124. Motor activities were measured by the number and order of beams broken by the animals. Four locomotor parameters, i.e., horizontal activity, total distance traveled, vertical activity, and vertical time, were recorded.

Quantitative Reverse Transcription—PCR (qRTPCR)

Cerebral cortex from each mouse was collected on day 5 after mTBI for qRTPCR analysis. See, e.g., Luo et al., Ann Neurol, 2009, 65:520-530; Luo et al., Ann Neurol, 2013, 65:520-530; and Shen et al., J Neurosci Res, 2009, 87:545-555. Total RNAs were isolated using TRIZOL Reagents (Life Technologies, #15596-026) and cDNAs were synthesized from 1 ug total RNA using a RevertAid First Strand cDNA Synthesis Kit (Thermo Scientific, #K1622). TaqMan Gene Expression Assays (primer and probe set) for specifically detecting IBA1 (#Rn00574125_g1) were purchased from Thermo Scientific. Primer probes used in the quantitative RT-PCR for reference genes are as follows: beta actin forward primer (5'-CATTGCTGACAGGATGCAGAAGG); reverse primer (5'-TGCTGGAAGGTGGACAGTGAGG); GAPDH forward primer (5'-CATCACTGCCACCCAGAA-GACTG); reverse primer (5'-ATGCCAGT-GAGCTTCCCGTTCAG). Quantitative Real-Time PCR (qRT-PCR) was carried out using TaqMan Fast Advanced Master Mix (Life Technologies, #4444557) and Applied Biosystems 7500 Fast Real-Time PCR System. Expression and normalization of the target gene IBA1 was calculated relative to the endogenous reference gene (Beta-actin+ GAPDH) with a modified delta-delta-Ct algorithm that takes specific gene specific amplification efficiency into account for accurate calculation. All experiments were duplicated.

Results

Adult CD1 mice were anesthetized with isoflurane followed by mTBI as reported in Shen et al., Clinical Proteomics, 2014, 11:11. Compound 42 or vehicle was given systemically after mTBI. Early post-treatment with Compound 42 significantly improved locomotor activity after mTBI. The expression of inflammatory marker ionized calcium-binding adapter molecule 1 (IBA1) in the lesioned cortex was examined by qRTPCR. It was observed that treatment with Compound 42 significantly reduced IBA1 expression in the mTBI brains.

More specifically, 22 mice were divided into two groups: a group of mTBI mice treated with vehicle (n=14) and a group of mTBI mice treated with Compound 42 (3 mg/kg, n=8). Behavior was analyzed every 3 hour for 24 hours starting from 15-minute after injury. A significant reduction in all locomotor activity was observed in mTBI mice, as compared to the non-mTBI mice (p<0.001, two way analysis of variance or ANOVA). Treatment with Compound 42 at a dosage of 3 mg/kg significantly improved vertical activity in mTBI mice (vertical activity, (p=0.009, $F_{1,140}$=6.969); and vertical movement time, (p=0.007, $F_{1,140}$=8.662).

Further, 15 mice were used to evaluate the effect of Compound 42 on neuroinflammation, in which 7 mice received the vehicle and 8 mice were treated with Compound 42 at a dosage of 3 mg/kg. Cerebral cortices were collected on day 5 after mTBI. The expression of neuroinflammatory marker IBA1 and reference genes (GAPDH actin and beta-actin) was measured for qRTPCR analysis. It was observed that the expression of both IBA1 (GAPDH actin) and IBA1 (beta-actin) in the lesioned side cortex was significantly suppressed in mTBI mice treated with Compound 42 (p=0.030, t-test).

These results, exhibition by Compound 42 of a neuroprotective effect in a mice model of mTBI, indicate that it is efficacious in treating mild traumatic brain injury.

EXAMPLE 8

Effect on Myocardial Infarction in Rat

The efficacy of a compound of Formula (I), i.e., Compound 42, in protecting against myocardial infarction was assessed in a rat ischemic myocardial infarction model as follows.

Male SD rats (400-500 gram each) received a single subcutaneous injection of Compound 42 at a dosage of 5 mg/kg or an equal volume of saline (n=18-20 per group) 30 minutes before surgery was conducted. Left anterior descending artery (LAD) was transiently ligated using a 6-0 nylon suture for a 30-minute ischemic period in this surgery. After 24 hours, each rat was anesthetized and the LAD was ligated again. 2 mL of 5% Evan's Blue was then injected into the tail vein and allowed to perfuse for 2 minutes. The heart was immediately excised, washed with saline, froze at −80° C., and cut in semi-frozen state into 2-mm thick sections. Slices were then incubated in 1% tri-phenyltetrazolium chloride solution for 10 minutes at 37° C. and fixed in 10% formalin. Infarct size was recorded after staining. It was observed that treatment with Compound 42 prior to surgery-induced ischemia/reperfusion protected heart against ischemic damage to a large degree.

The results indicate that Compound 42 is effective in protecting against myocardial infarction in rats.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

REFERENCES

1. Schols D, Struyf S, Van Damme J, Esté J A, Henson G, De Clercq E. Inhibition of T-tropic HIV strains by selective antagonization of the chemokine receptor CXCR4. *J. Exp. Med.* 186:1383-1388 (1997).
2. Wu C H, Wang C J, Chang C P, Cheng Y C, Song J S, Jan J J, Chou M C, Ke Y Y, Ma J, Wong Y C, Hsieh T C, Tien Y C, Gullen E A, Lo C F, Cheng C Y, Liu Y W, Sadani A A, Tsai C H, Hsieh H P, Tsou L K, Shia K S. Function-oriented development of CXCR4 antagonists as selective human immunodeficiency virus (HIV)-1 entry inhibitors. *J. Med. Chem.* 58:1452-1465 (2015).
3. Lenoir M, Djerdjouri B, Périanin A. Stroma cell-derived factor 1 alpha mediates desensitization of human neutrophil respiratory burst in synovial fluid from rheumatoid arthritic patients. *J. Immunol.* 172:7136-7143 (2004).
4. Gonzalo J A, Lloyd C M, Peled A, Delaney T, Coyle A J, Gutierrez-Ramos J C. Critical involvement of the chemotactic axis CXCR4/stromal cell-derived factor-1 alpha in the inflammatory component of allergic airway disease. *J. Immunol.* 165:499-508 (2000).
5. Müller A, Homey B, Soto H, Ge N, Catron D, Buchanan M E, McClanahan T, Murphy E, Yuan W, Wagner S N, Barrera J L, Mohar A, Verástegui E, Zlotnik A. Involvement of chemokine receptors in breast cancer metastasis. *Nature.* 410:50-56 (2001).
6. Liang Z, Yoon Y, Votaw J, Goodman M M, Williams L, Shim H. Silencing of CXCR4 blocks breast cancer metastasis. *Cancer Res.* 65:967-971 (2005).
7. Lin Q, Wesson R N, Maeda H, Wang Y, Cui Z, Liu J O, Cameron A M, Gao B, Montgomery R A, Williams G M, Sun Z. Pharmacological mobilization of endogenous stem cells significantly promotes skin regeneration after full-thickness excision: the synergistic activity of AMD3100 and tacrolimus. *J. Invest. Dermatol.* 134:2458-2468 (2014).
8. Lukacs N W, Berlin A, Schols D, Skerlj R T, Bridger G J. AMD3100, a CxCR4 antagonist, attenuates allergic lung inflammation and airway hyperreactivity. *Am. J. Pathol.* 160:1353-1360 (2002).
9. Huang J, Li Y, Tang Y, Tang G, Yang G Y, Wang Y. CXCR4 antagonist AMD3100 protects blood-brain barrier integrity and reduces inflammatory response after focal ischemia in mice. *Stroke.* 44:190-197 (2013).
10. Wu C H, Song J S, Chang K H, Jan J J, Chen C T, Chou M C, Yeh K C, Wong Y C, Tseng C T, Wu S H, Yeh C F, Huang C Y, Wang M H, Sadani A A, Chang C P, Cheng C Y, Tsou L K, Shia K S. Stem cell mobilizers targeting chemokine receptor CXCR4: renoprotective application in acute kidney injury. *J. Med. Chem.* 58:2315-2325 (2015).
11. Wu K J, Yu S J, Shia K S, Wu C H, Song J S, Kuan H H, Yeh K C, Chen C T, Bae E, Wang Y. A novel CXCR4 antagonist CX549 induces neuroprotection in stroke brain. *Cell transplantation.* in press (2017).
12. Chen Y, Huang Y, Reiberger T, Duyverman A M, Huang P, Samuel R, Hiddingh L, Roberge S, Koppel C, Lauwers G Y, Zhu A X, Jain R K, Duda D G. Differential effects of sorafenib on liver versus tumor fibrosis mediated by stromal-derived factor 1 alpha/C—X—C receptor type 4 axisand myeloid differentiation antigen-positive myeloid cell infiltration in mice. *Hepatology.* 59:1435-1447 (2014).
13. Matthys P, Hatse S, Vermeire K, Wuyts A, Bridger G, Henson G W, De Clercq E, Billiau A, Schols D. AMD3100, a potent and specific antagonist of the stromal cell-derived factor-1 chemokine receptor CXCR4, inhibits autoimmune joint inflammation in IFN-gamma receptor-deficient mice. *J. Immunol.* 167:4686-4692 (2001).

What is claimed is:

1. A compound of formula (I):

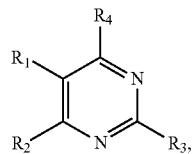

(I)

wherein
each of $R_1$ and $R_2$, independently, is H, halo, $NO_2$, CN, $NH_2$, $C_{1-6}$ alkyl, $C_{1-6}$ alkoxyl, $C_{3-10}$ cycloalkyl, $C_{1-10}$ heterocycloalkyl, aryl, or heteroaryl; or $R_1$ and $R_2$, together with the two carbon atoms to which they are bonded, are $C_{5-10}$ cycloalkyl, $C_{3-10}$ heterocycloalkyl, aryl, or heteroaryl, each of the $C_{1-6}$ alkyl, $C_{1-6}$ alkoxyl, $C_{3-10}$ cycloalkyl, $C_{1-10}$ heterocycloalkyl, $C_{5-10}$ cycloalkyl, $C_{3-10}$ heterocycloalkyl, aryl, and heteroaryl being optionally substituted with halo, $NO_2$, CN, $NH_2$, $C_{1-6}$ alkyl, $C_{1-6}$ alkoxyl, aryl, heteroaryl, or $C(O)OR_a$, in which $R_a$ is H, $C_{1-10}$ alkyl, $C_{3-10}$ cycloalkyl, $C_{3-10}$ heterocycloalkyl, aryl, or heteroaryl; and each of $R_3$ and $R_4$, independently, is

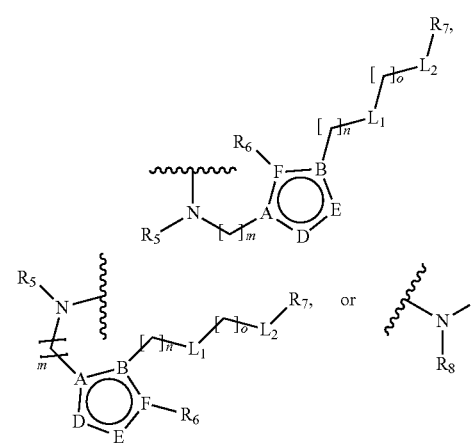

in which at least one of $R_3$ and $R_4$ is

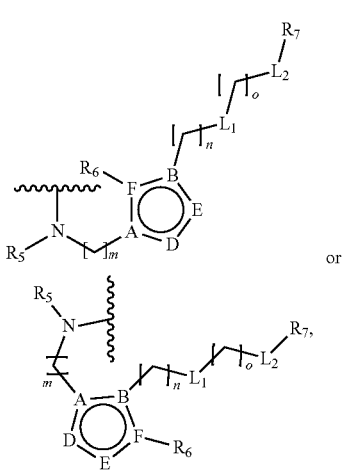

$R_5$ is H, $C_{1-6}$ alkyl, $C_{3-10}$ cycloalkyl, $C_{1-10}$ heterocycloalkyl, aryl alkyl, heteroaryl alkyl, aryl, or heteroaryl, each of the $C_{1-6}$ alkyl, $C_{3-10}$ cycloalkyl, $C_{1-10}$ heterocycloalkyl, aryl alkyl, heteroaryl alkyl, aryl, and heteroaryl being optionally substituted with halo, nitro, cyano, amino, $C_{1-6}$ alkyl, $C_{1-6}$ alkoxyl, $C_{3-10}$ cycloalkyl, $C_{1-10}$ heterocycloalkyl, aryl, or heteroaryl;

$R_6$ is deleted, H, $C_{1-6}$ alkyl, $C_{1-6}$ alkoxyl, $C_{3-10}$ cycloalkyl, $C_{1-10}$ heterocycloalkyl, aryl, or heteroaryl, each of the $C_{1-6}$ alkyl, $C_{1-6}$ alkoxyl, $C_{3-10}$ cycloalkyl, $C_{1-10}$ heterocycloalkyl, aryl, and heteroaryl being optionally substituted with hydroxy, hydroxy $C_{1-6}$ alkyl, halo, nitro, cyano, or amino;

$R_7$ is H, $C_{1-6}$ alkyl, $C_{1-6}$ alkoxyl, $C_{3-10}$ cycloalkyl, $C_{1-10}$ heterocycloalkyl, aryl, or heteroaryl, each of the $C_{1-6}$ alkyl, $C_{1-6}$ alkoxyl, $C_{3-10}$ cycloalkyl, $C_{1-10}$ heterocycloalkyl, aryl, and heteroaryl being optionally substituted with hydroxy, hydroxy $C_{1-6}$ alkyl, halo, nitro, cyano, amino, amino $C_{1-6}$ alkyl, amino $C_{3-10}$ cycloalkyl, amino $C_{1-10}$ heterocycloalkyl, $C_{3-10}$ cycloalkyl, $C_{1-10}$ heterocycle, aryl, or heteroaryl;

each of A and B in

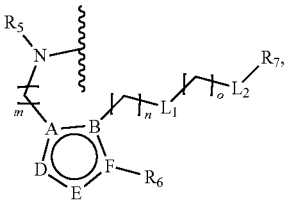

independently, is C or N; and each of D, E and F in

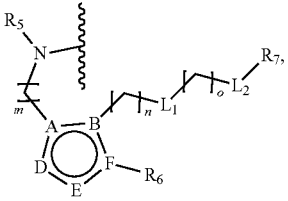

independently, is C, N, O, or S; in which when B is C and $R_3$ is

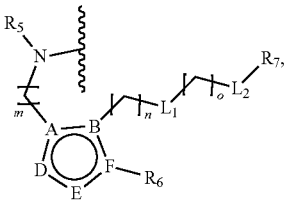

then at least one of D and E is C, O, or S; and when B is N and $R_3$ is

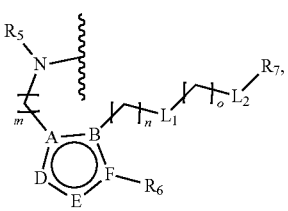

then D is N; and

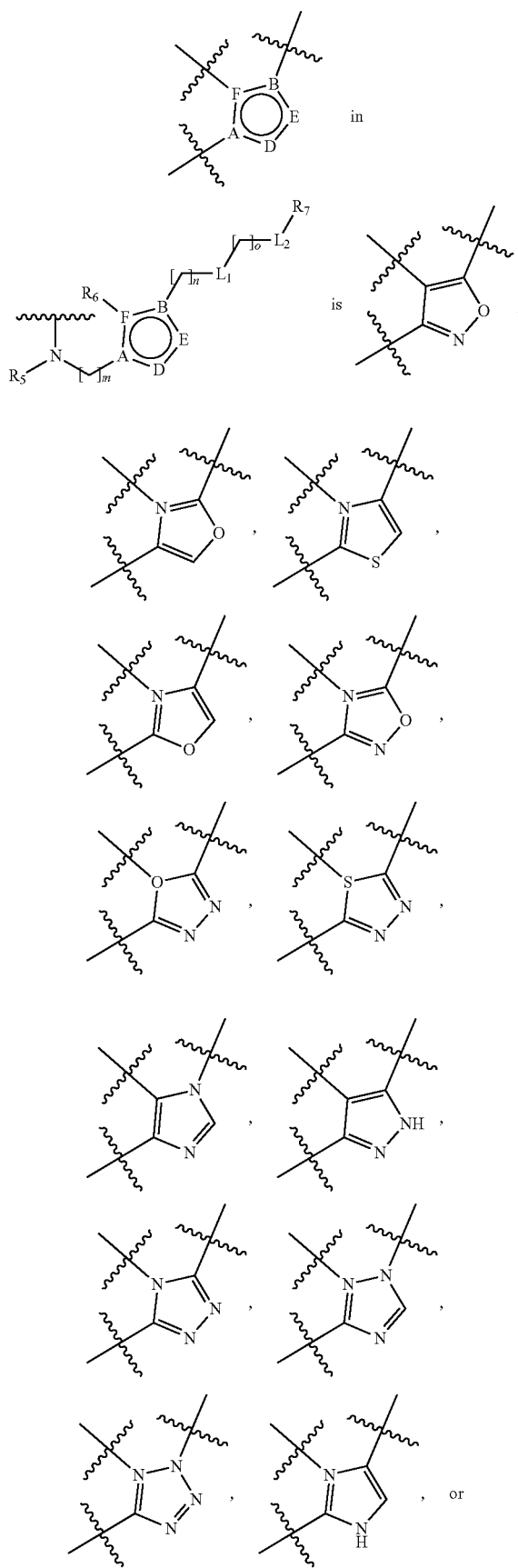#

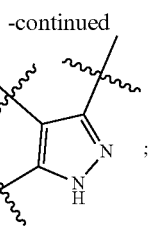

each of $L_1$ and $L_2$, independently, is heteroaryl, $C_{1-10}$ heterocycloalkyl, or $NR_d$, in which $R_d$ is H or $C(O)(CH_2)_2CHNH_2CO_2R_e$, $R_e$ being H, $C_{1-6}$ alkyl, $C_{3-10}$ cycloalkyl, $C_{3-10}$ heterocycloalkyl, aryl, or heteroaryl;

each of m, n, and o, independently, is 1, 2, 3, 4, 5, or 6;

each of $R_8$ and $R_9$, independently, is H, $C_{1-6}$ alkyl, $C_{3-10}$ cycloalkyl, $C_{1-10}$ heterocycloalkyl, aryl, or heteroaryl, each of the $C_{1-6}$ alkyl, $C_{3-10}$ cycloalkyl, $C_{1-10}$ heterocycloalkyl, aryl, and heteroaryl being optionally substituted with $C(O)OR_f$, in which $R_f$ is H, $C_{1-10}$ alkyl, $C_{3-20}$ cycloalkyl, $C_{3-20}$ heterocycloalkyl, aryl, or heteroaryl; or $R_8$ and $R_9$, together with the nitrogen atoms to which they are bonded, are $C_{3-10}$ heterocycloalkyl;

$L_3$ is $C_{1-6}$ alkyl; or $L_3$, together with $R_8$ or $R_9$ and the nitrogen atom to which they are bonded, is $C_{4-10}$ heterocycloalkyl or heteroaryl; and $R_{10}$ is H, $C_{1-6}$ alkyl, $C_{1-6}$ alkoxyl, $C_{3-10}$ cycloalkyl, $C_{1-10}$ heterocycloalkyl, aryl, heteroaryl, or

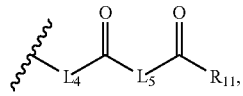

in which $L_4$ is deleted or $C_{1-6}$ alkylamino; $L_5$ is $C_{1-6}$ alkyl, $C_{1-6}$ alkylamino, or di-$C_{1-6}$ alkylamino; and $R_{11}$ is hydroxyl or $C_{1-6}$ alkylamino; each of the $C_{1-6}$ alkyl, $C_{1-6}$ alkoxyl, $C_{3-10}$ cycloalkyl, $C_{1-10}$ heterocycloalkyl, $C_{1-6}$ alkylamino; di-$C_{1-6}$ alkylamino, aryl, and heteroaryl being optionally substituted with hydroxyl, amino, $C(O)OR_{12}$, or $P(O)(OR_{13})_2$, in which each of $R_{12}$ and $R_{13}$, independently, is H or $C_{1-6}$ alkyl.

2. The compound of claim 1, wherein each of $R_1$ and $R_2$, independently, is H or $C_{1-6}$ alkyl.

3. The compound of claim 1, wherein each of $R_1$ and $R_2$, independently, is H, $NH_2$, or $C_{1-10}$ heterocycloalkyl optionally substituted with $C_{1-6}$ alkyl or $C(O)OR_a$, in which $R_a$ is H or $C_{1-10}$ alkyl.

4. The compound of claim 1, wherein $R_1$ and $R_2$, together with the two carbon atoms to which they are bonded, are aryl or heteroaryl.

5. The compound of claim 4, wherein $R_1$ and $R_2$, together with the two carbon atoms to which they are bonded, are

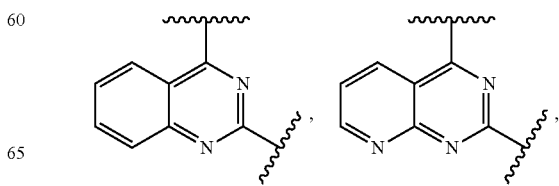

-continued

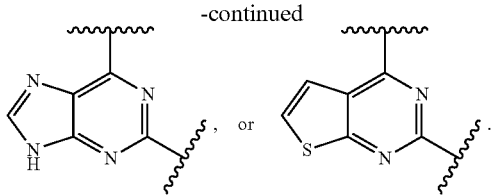

6. The compound of claim 1, wherein each of $R_3$ and $R_4$, independently, is

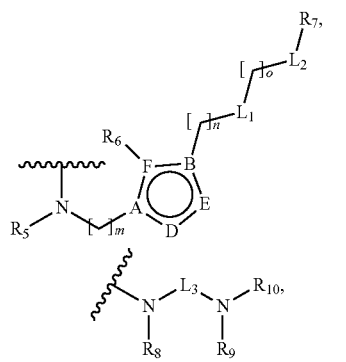

in which $R_5$ is H; $R_6$ is deleted; each of m, n, and o, independently, is 1, 2, 3, or 4; and each of $L_1$ and $L_2$ is $NR_d$.

7. The compound of claim 6, wherein

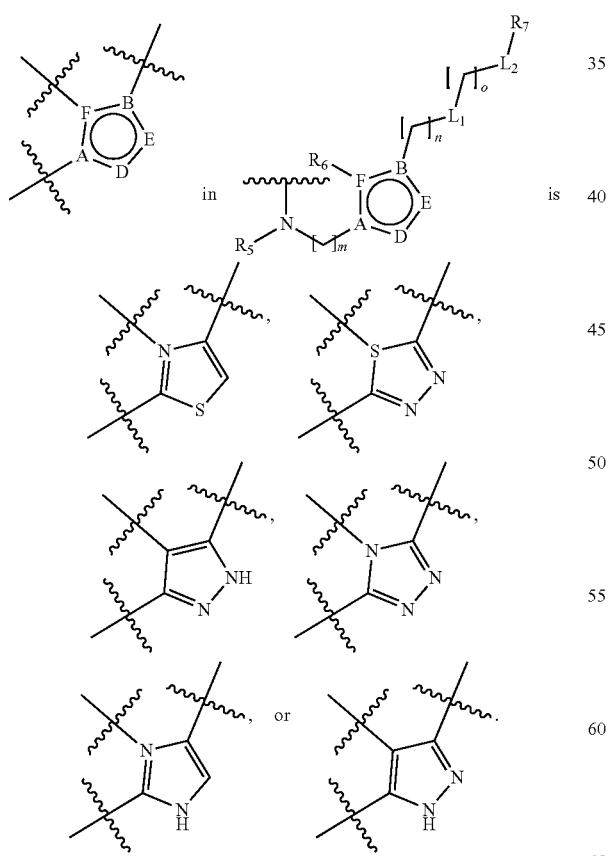

8. The compound of claim 6, wherein each of $R_1$ and $R_2$, independently, is H or $C_{1-6}$ alkyl.

9. The compound of claim 8, wherein $R_1$ is H and $R_2$ is Cl-6 alkyl.

10. The compound of claim 6, wherein $R_1$ and $R_2$, together with the two carbon atoms to which they are bonded, are aryl or heteroaryl.

11. The compound of claim 10, wherein $R_1$ and $R_2$, together with the two carbon atoms to which they are bonded, are

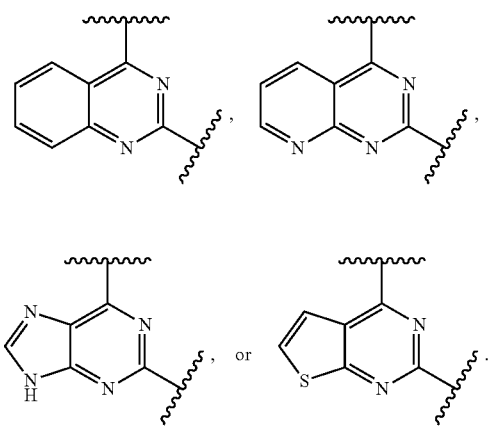

12. The compound of claim 1, wherein $R_3$ is

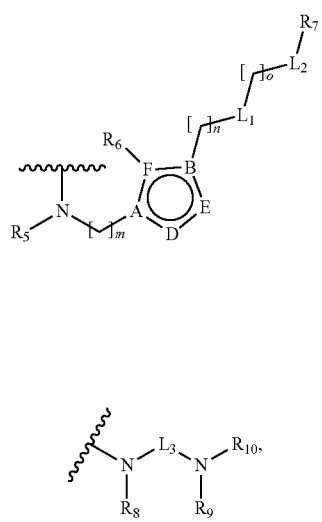

and $R_4$ is a which $R_5$ is H; $R_6$ is deleted;
each of m, n, and o, independently, is 1, 2, 3, or 4; and each of $L_1$ and $L_2$ is $NR_d$.

13. The compound of claim 12, wherein each of $R_1$ and $R_2$, independently, is H or $C_{1-6}$ alkyl.

14. The compound of claim 13, wherein $R_1$ is H and $R_2$ is $C_{1-6}$ alkyl.

15. The compound of claim 12, wherein $R_1$ and $R_2$, together with the two carbon atoms to which they are bonded, are aryl or heteroaryl.

16. The compound of claim 15, wherein $R_1$ and $R_2$, together with the two carbon atoms to which they are bonded, are

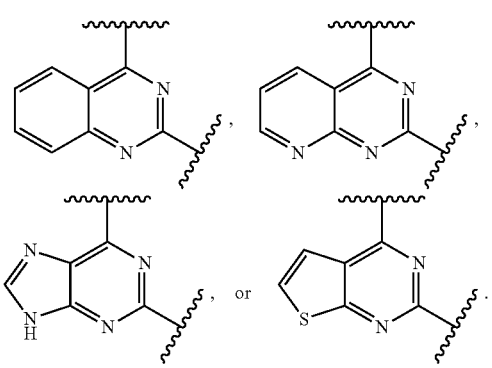

17. The compound of claim 16, wherein $R_1$ and $R_2$, together with the two carbon atoms to which they are bonded, are

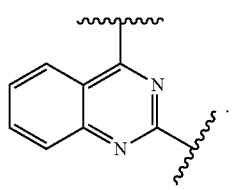 [SMILES: *c1nc(*)c2ccccc2n1]

18. The compound of claim 16, wherein

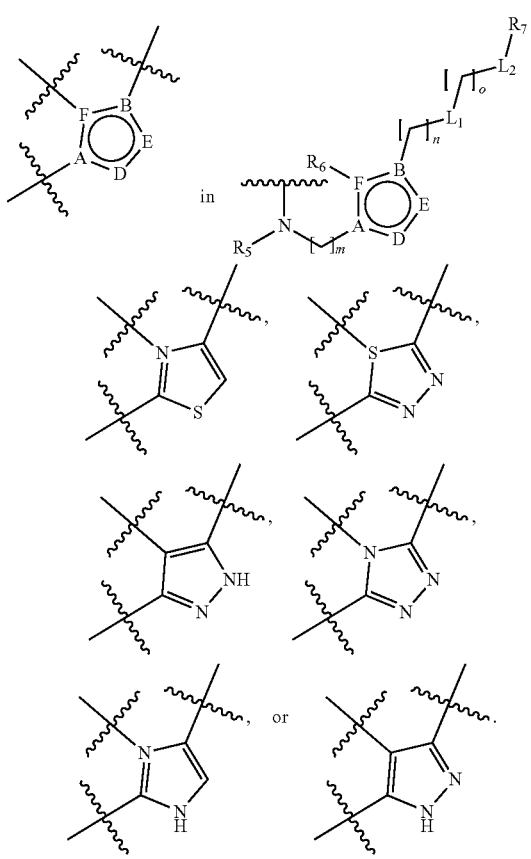

19. The compound of claim 12, wherein $L_3$, together with $R_8$ or $R_9$ and the nitrogen atom to which they are bonded, is $C_{4-10}$ heterocycloalkyl.

20. The compound of claim 19, wherein $R_8$ is H and $L_3$, together with $R_9$ and the nitrogen atom to which they are bonded, is $C_{4-10}$ heterocycloalkyl.

21. The compound of claim 20, wherein $R_1$ is H and $R_2$ is $C_{1-6}$ alkyl.

22. The compound of claim 20, wherein $R_1$ and $R_2$, together with the two carbon atoms to which they are bonded, are

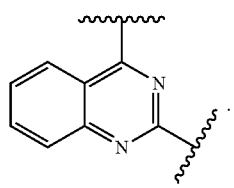 [SMILES: *c1nc(*)c2ccccc2n1]

23. The compound of claim 22, wherein

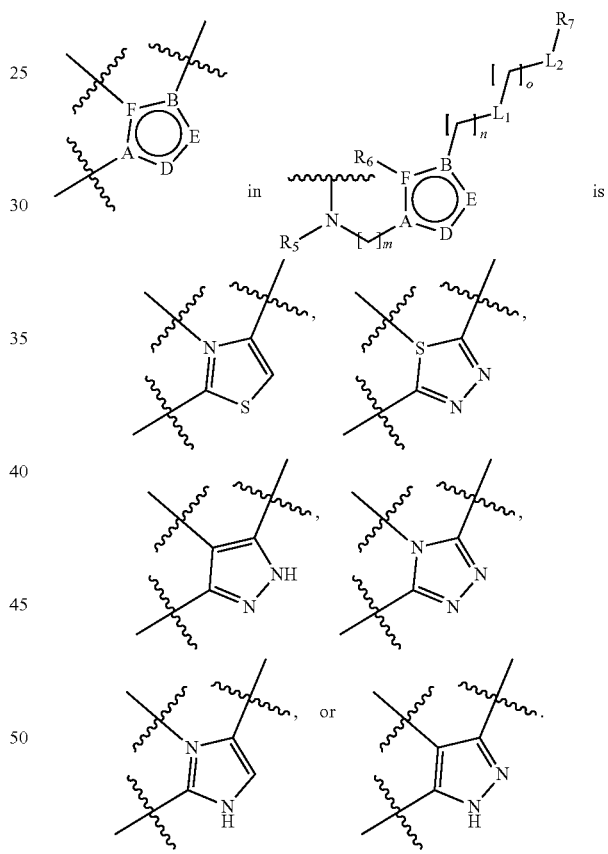

24. The compound of claim 20, wherein $R_{10}$ is H or

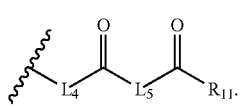

25. The compound of claim 24, wherein $R_1$ is H and $R_2$ is $C_{1-6}$ alkyl or $R_1$ and $R_2$, together with the two carbon atoms to which they are bonded, are

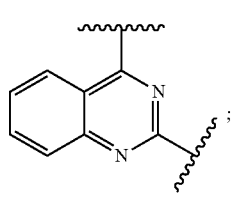 [SMILES: *c1nc(*)c2ccccc2n1]
R$_{10}$ is
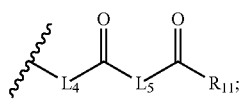
and
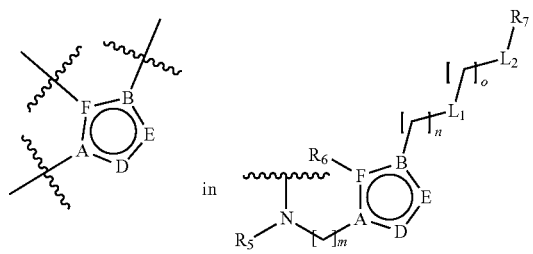
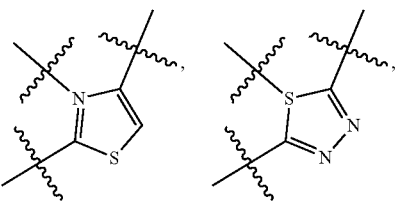
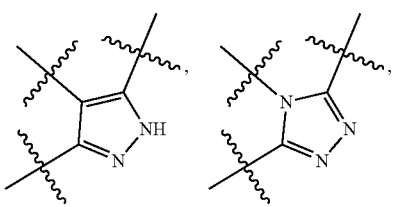
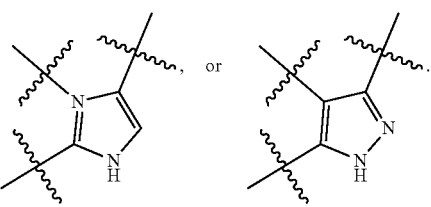
26. The compound of claim 1, wherein the compound is one of the following compounds:
1
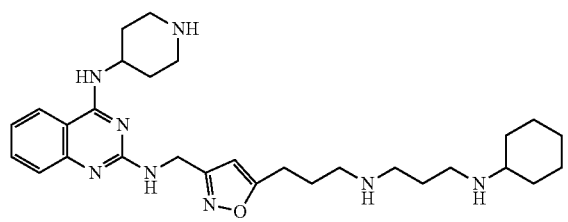
2
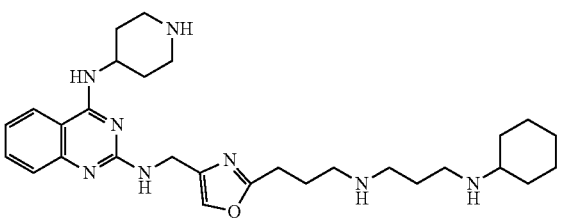
3
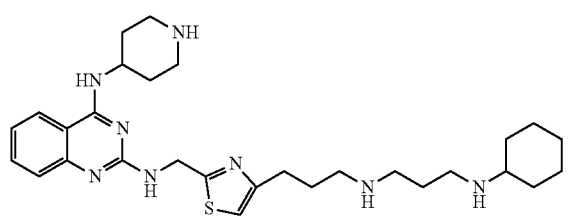
4
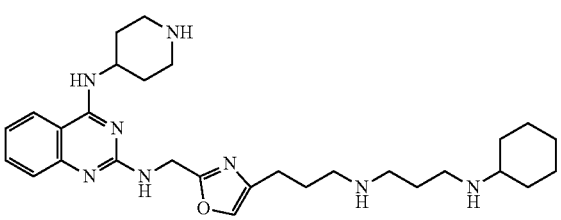
5
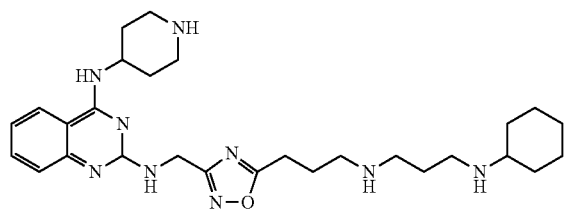
6
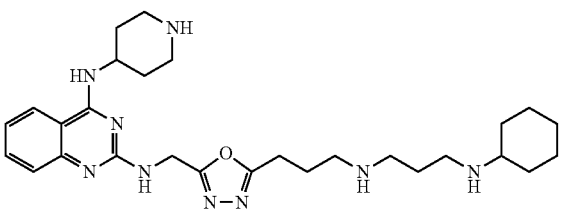
7
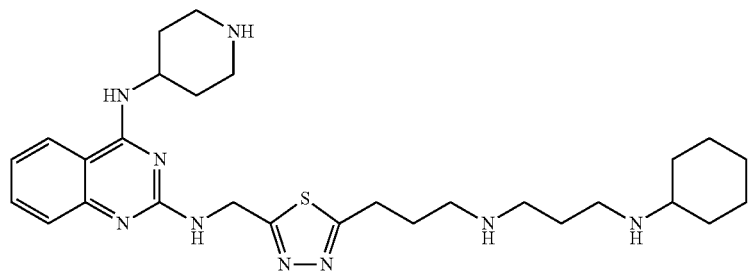

-continued
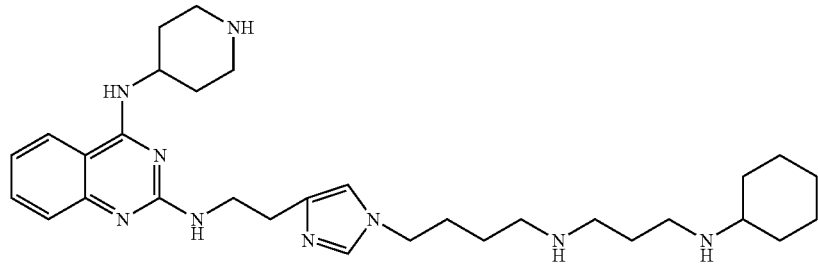
8
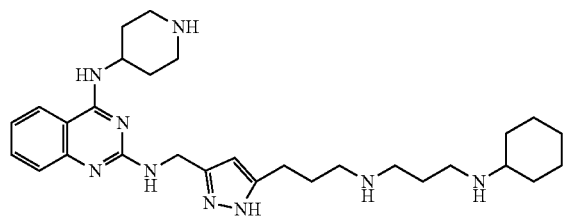
9
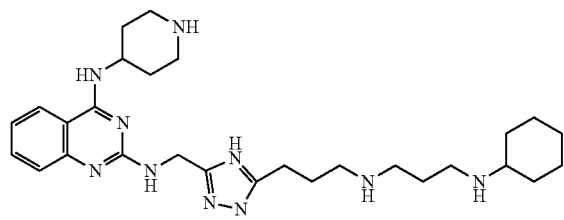
10
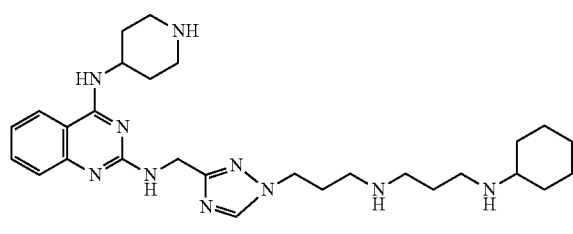
11
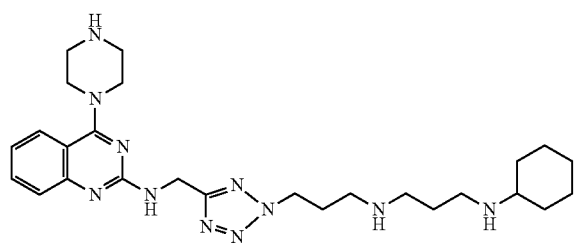
12
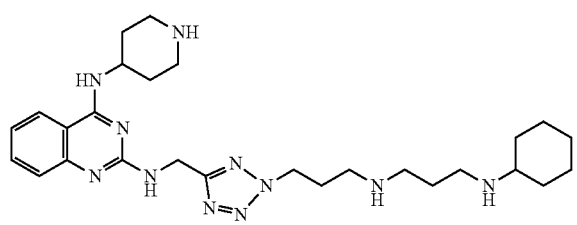
13
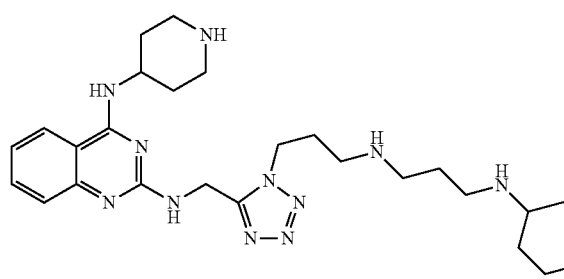
14
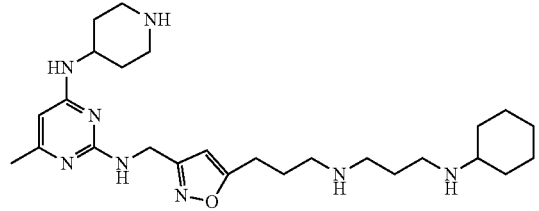
15
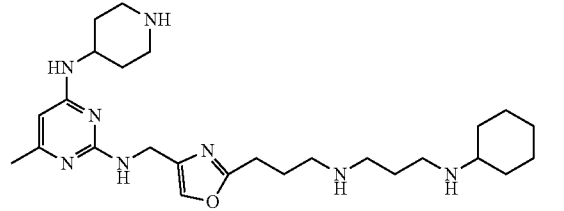
16
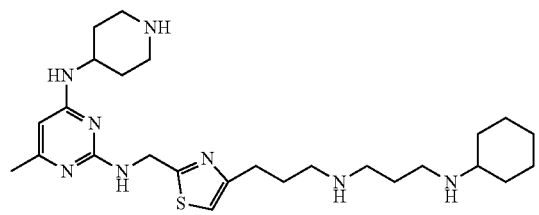
17
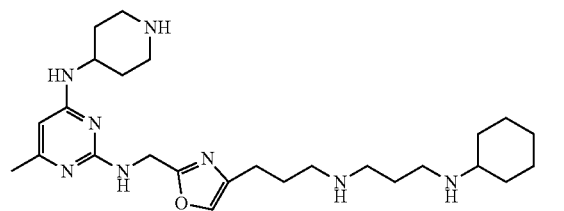
18

-continued
19
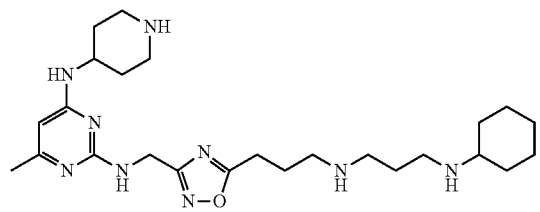
20
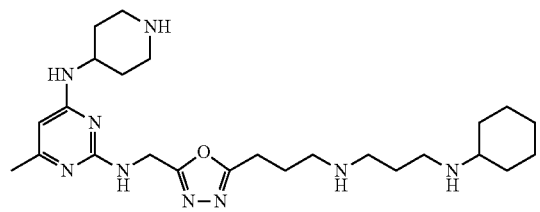
21
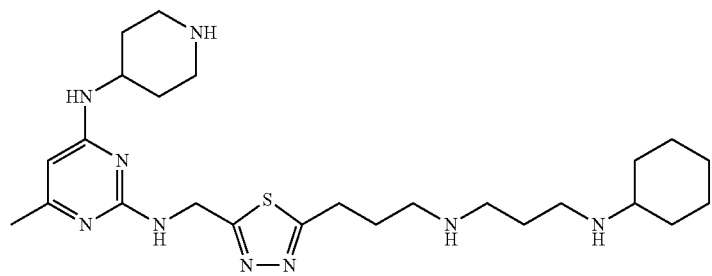
22
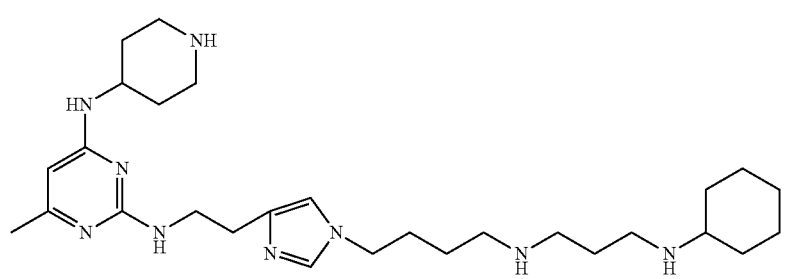
23
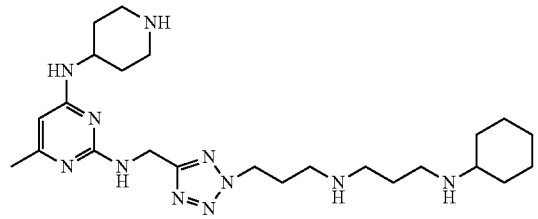
24
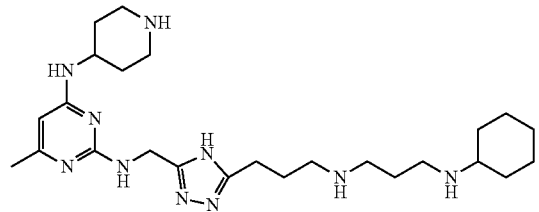
25
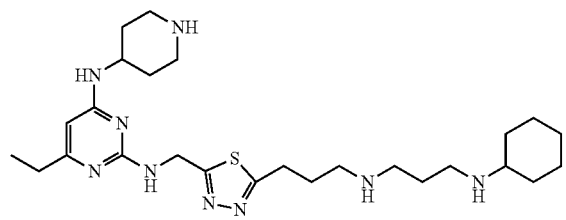
26
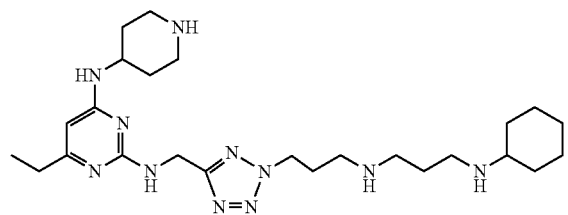
27
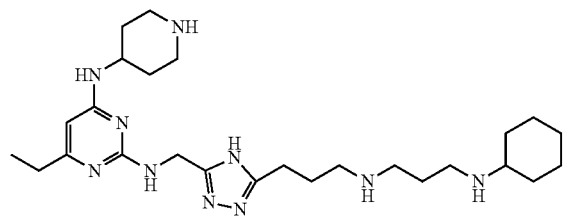
28
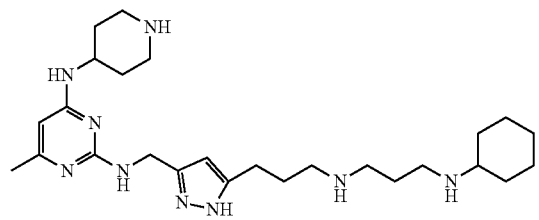

29
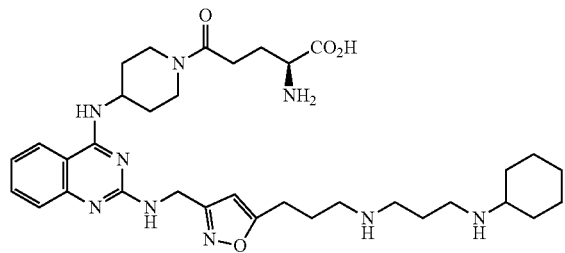
30
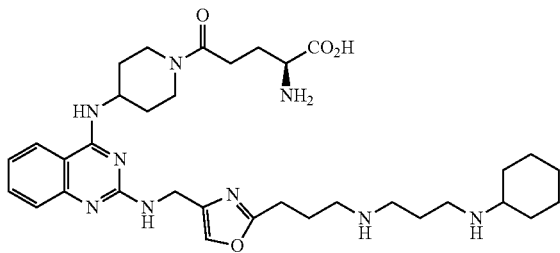
31
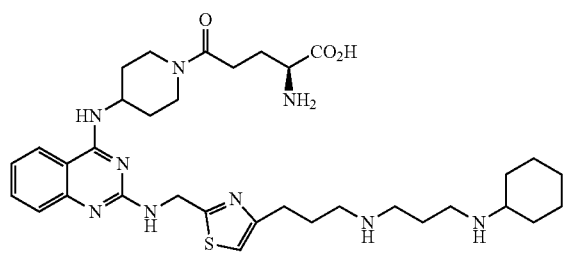
32
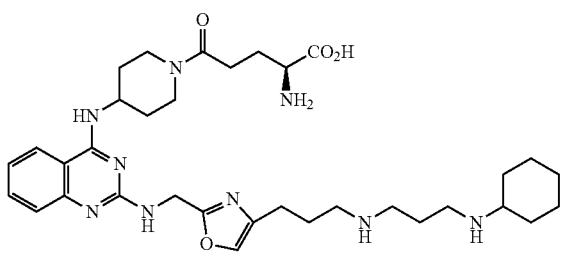
33
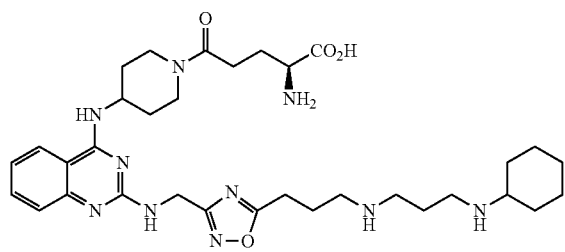
34
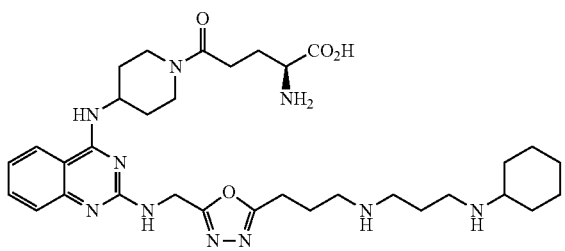
35
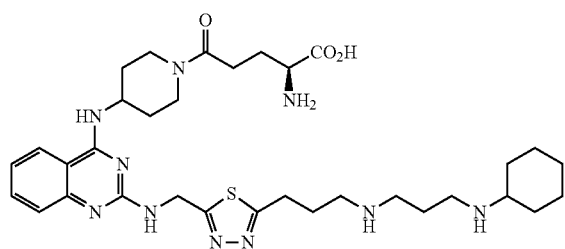
36
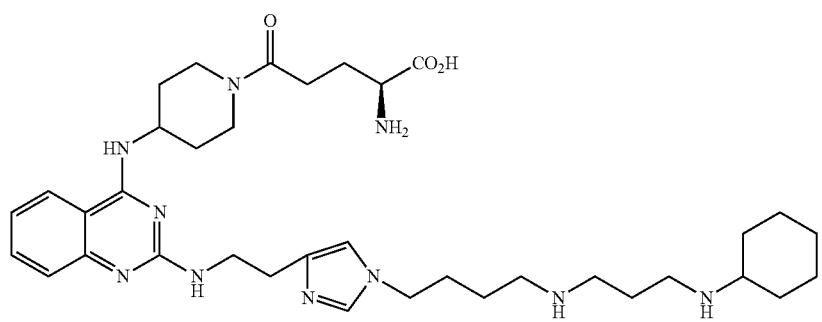

-continued
37
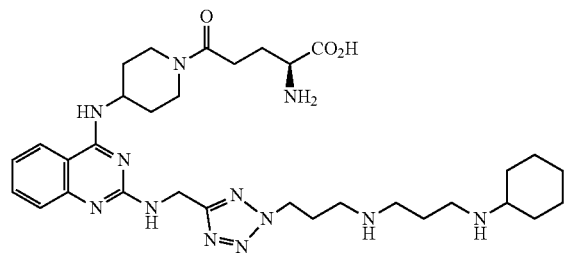
38
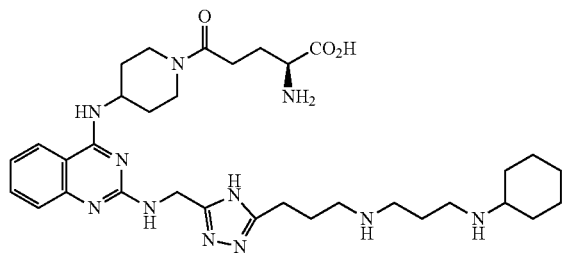
39
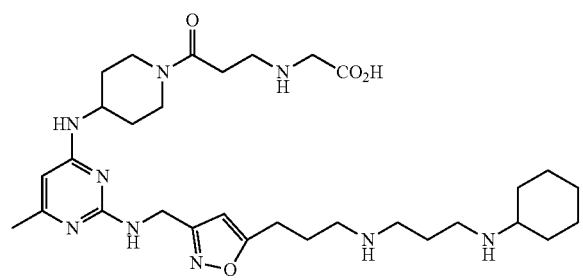
40
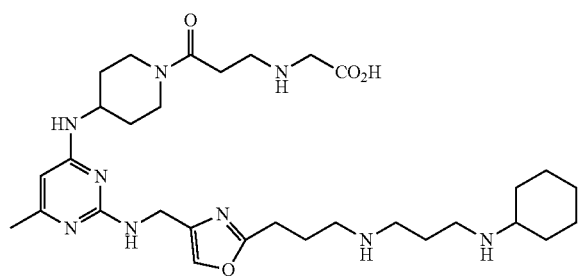
41
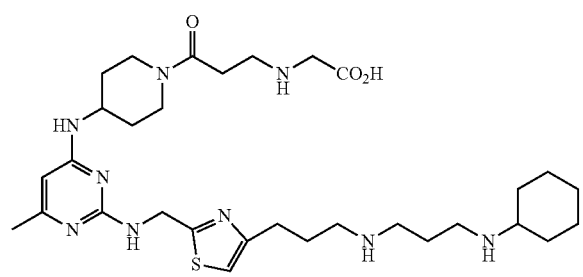
42
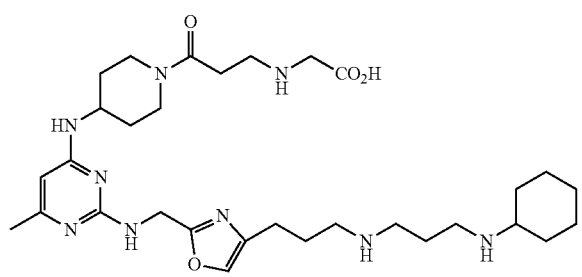
43
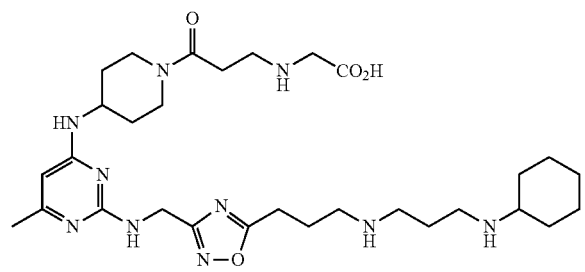
44
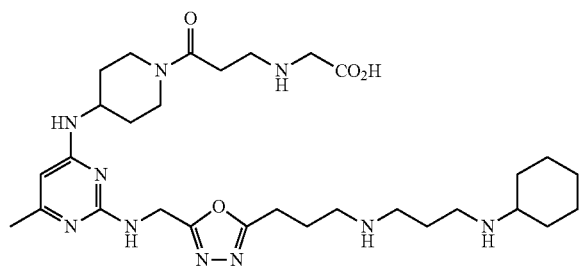
45
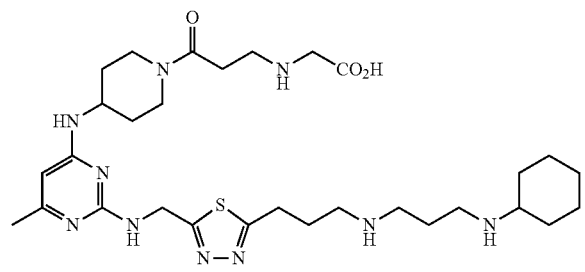
46
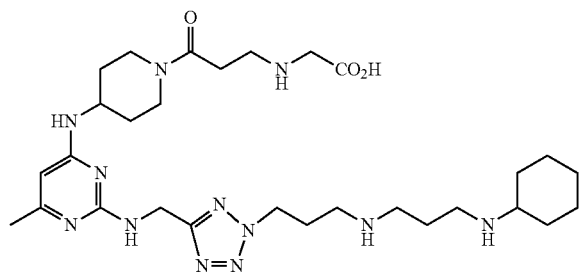

-continued
47
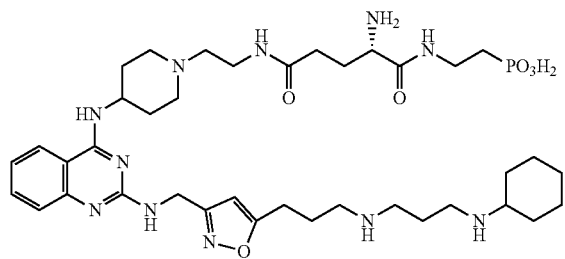
48
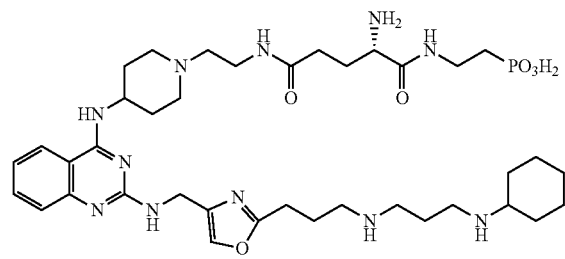
49
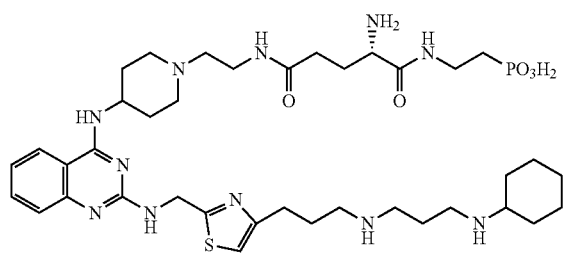
50
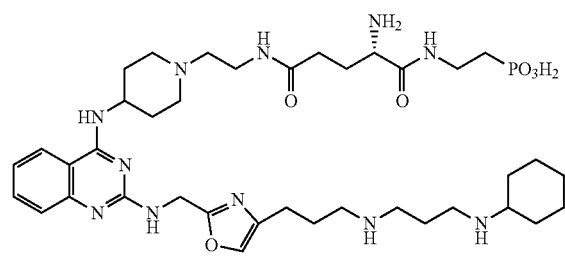
51
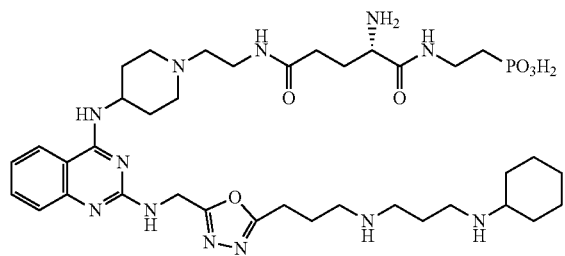
52
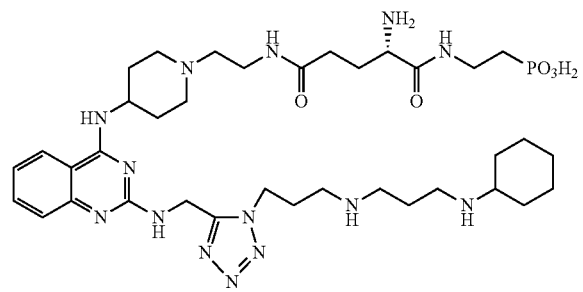
53
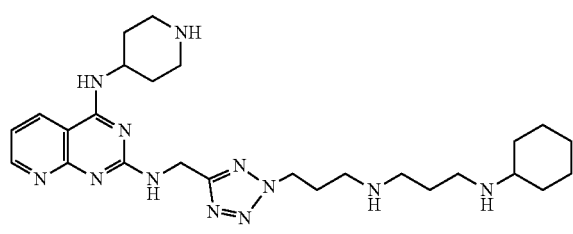
54
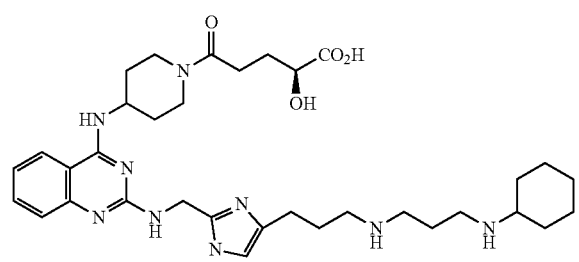
55
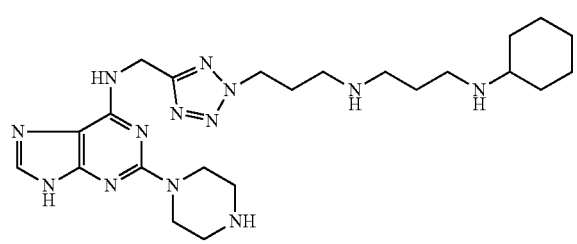
56
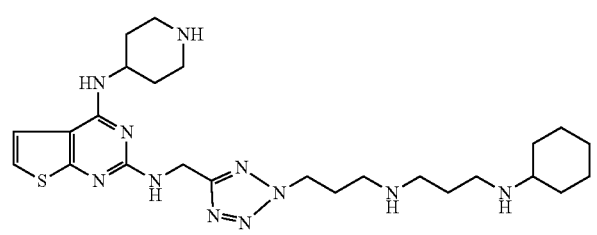

-continued
57
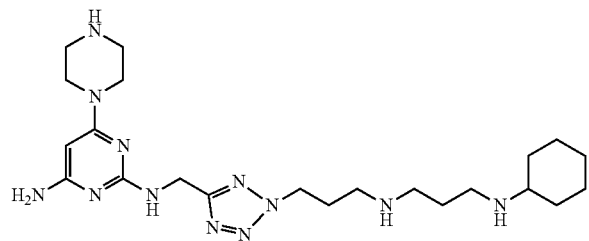
58
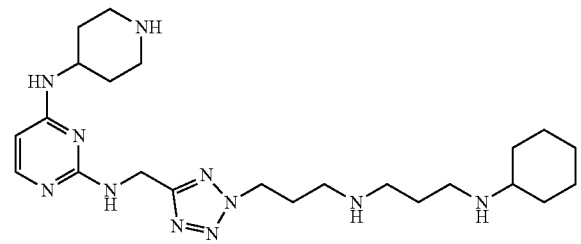
59
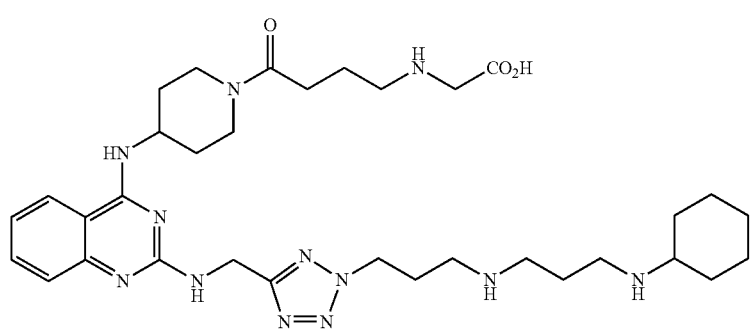
60
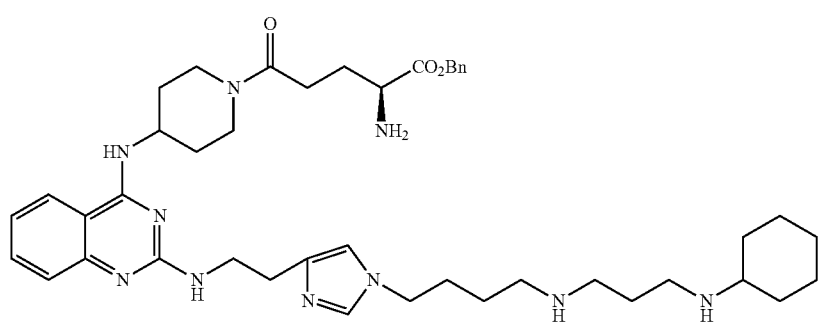
61
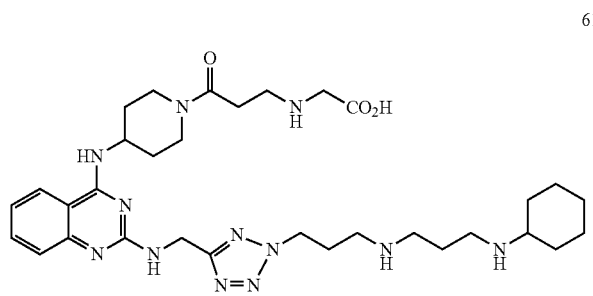
62
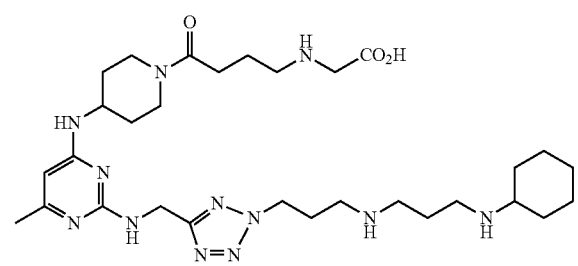
63
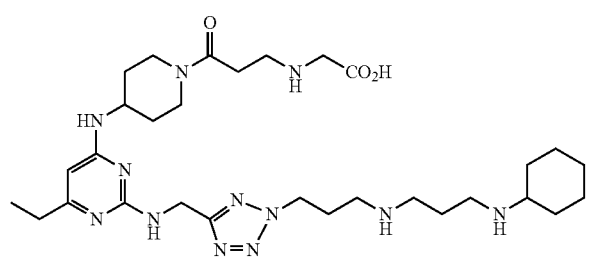
64
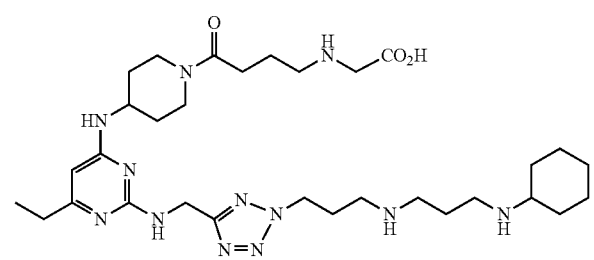

-continued
| 65 | 66 |
|---|---|
| 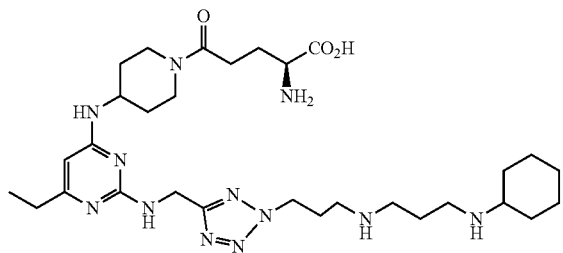 | 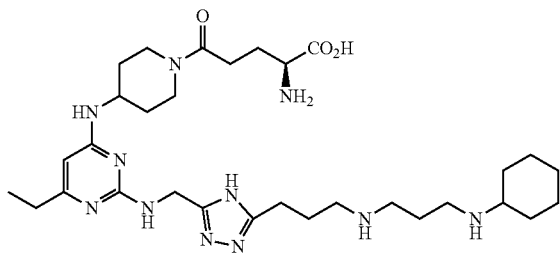 |
| 67 | 68 |
| 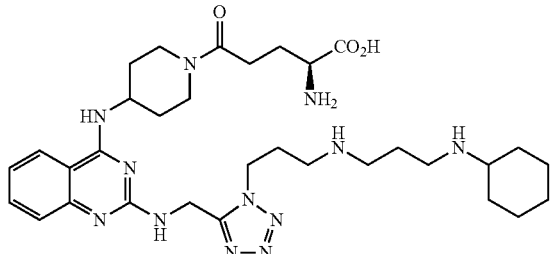 | 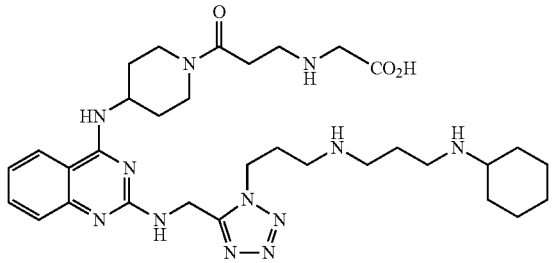 |
| 69 | 70 |
| 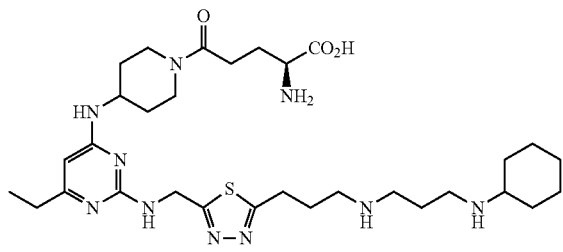 | 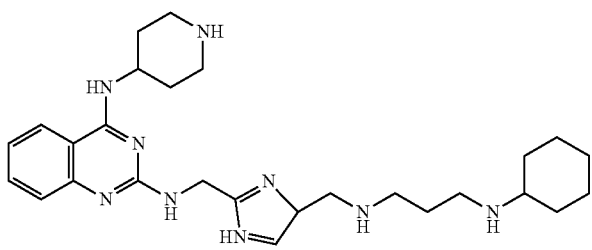 |
| 71 | 72 |
| 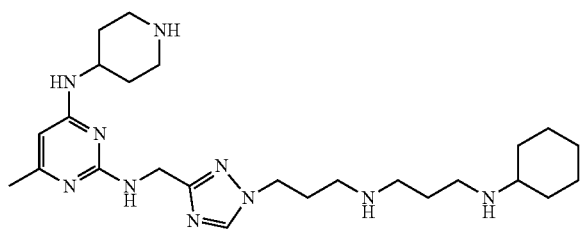 | 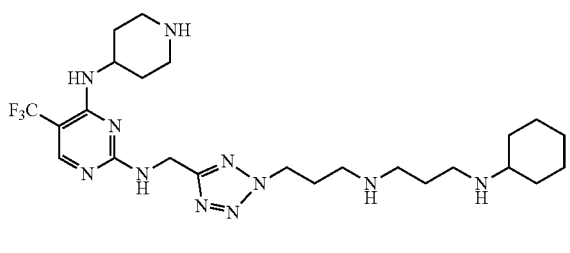 |
| 73 | 74 |
| 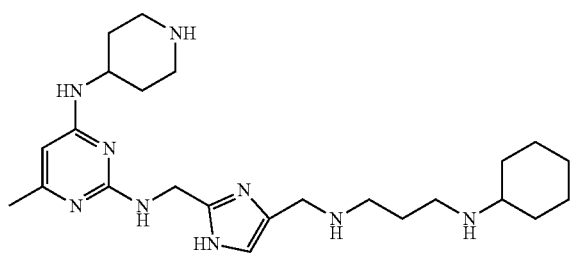 | 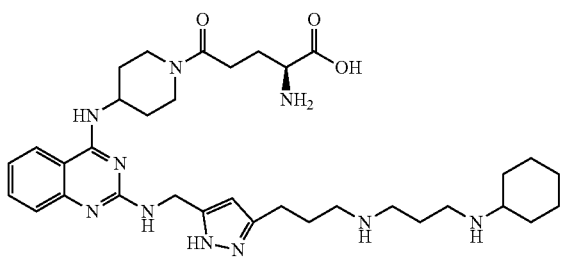 |
| 75 | 76 |
| 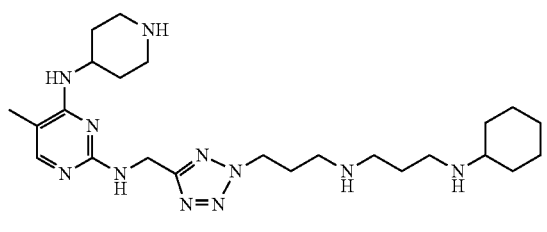 | |

-continued
77
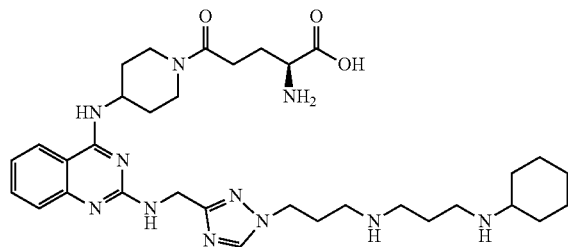
78
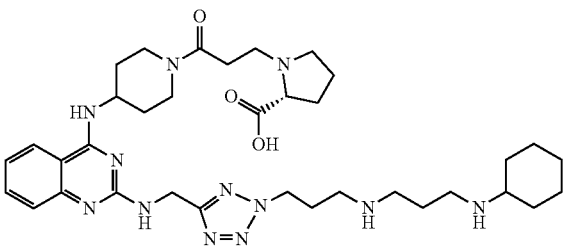
79
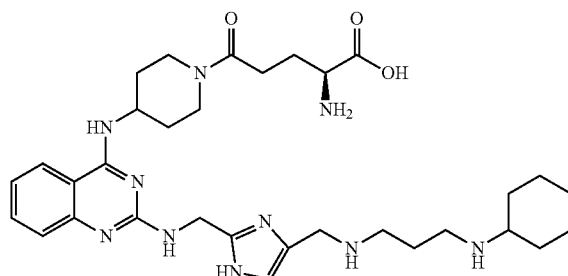
80
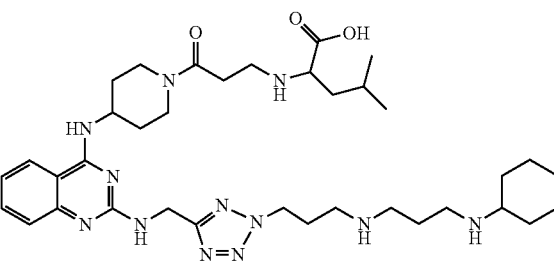
81
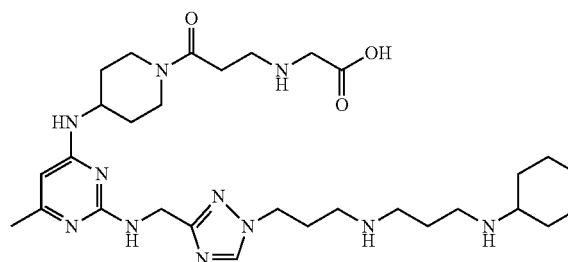
82
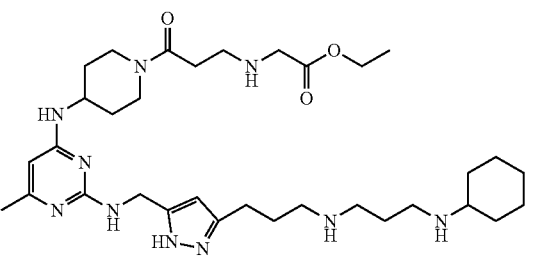
83
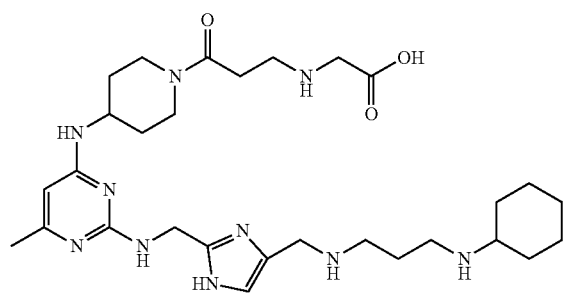
84
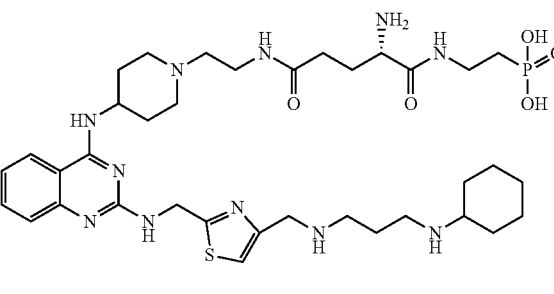
85
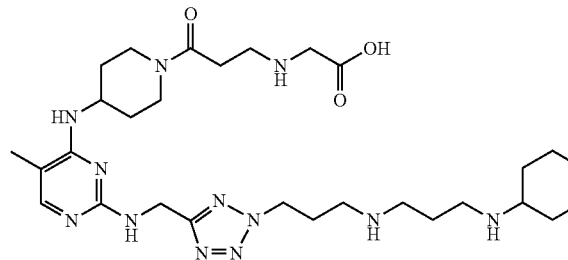
86
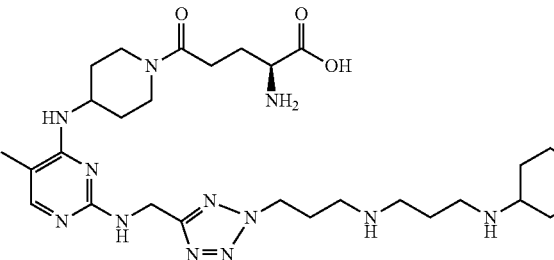

27. The compound of claim 1, wherein the compound is one of the following compounds:
3
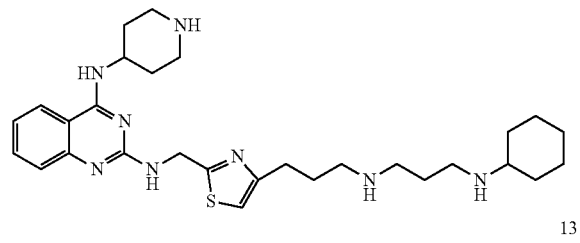
13
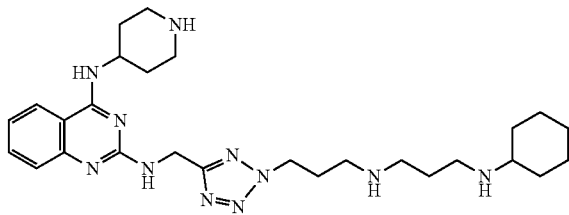
34
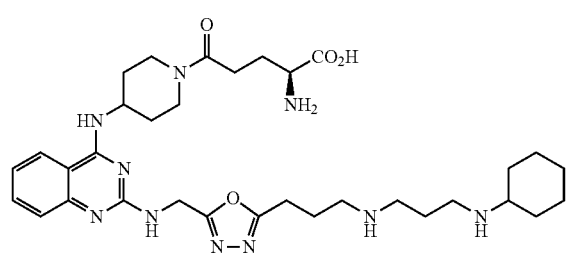
38
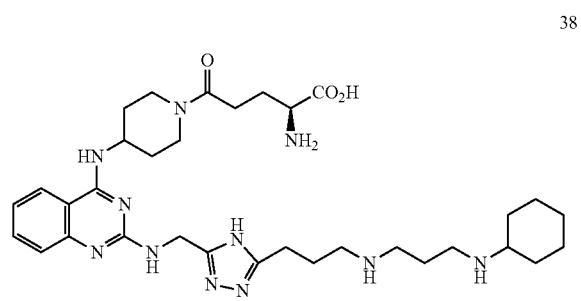
40
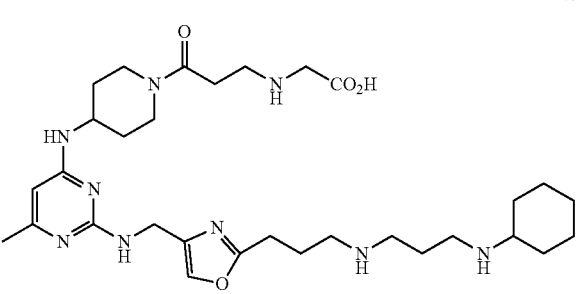
41
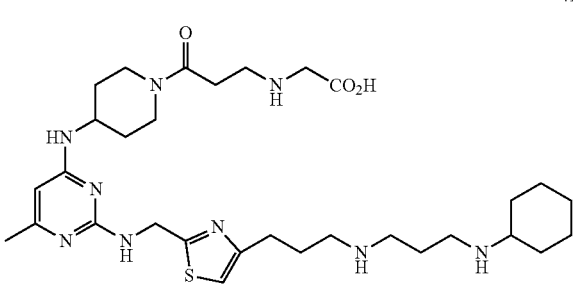
42
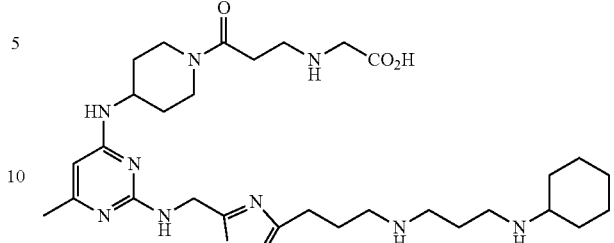
45
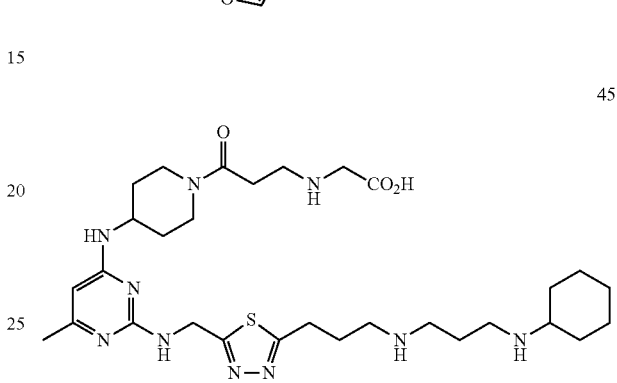
46
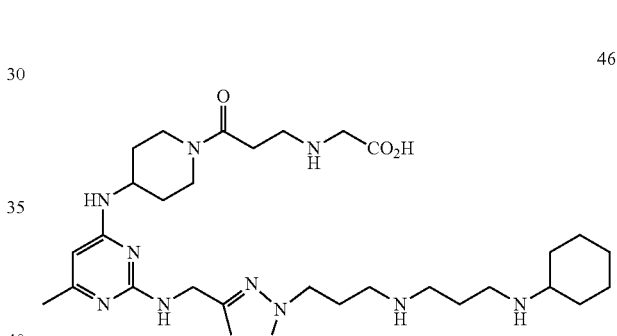
49
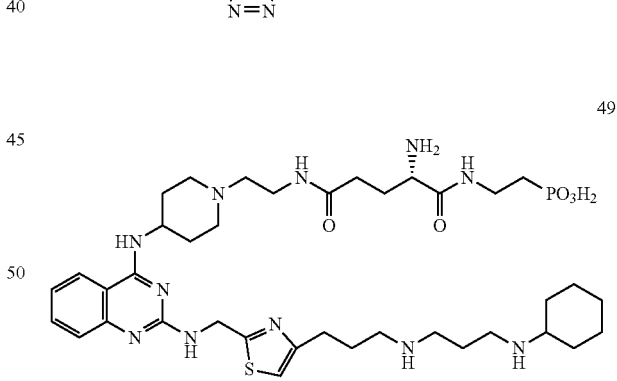
50
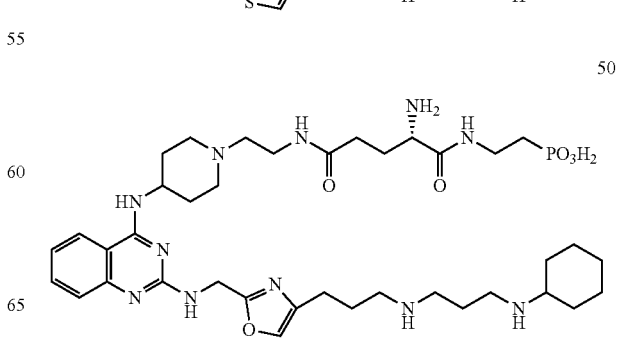

-continued

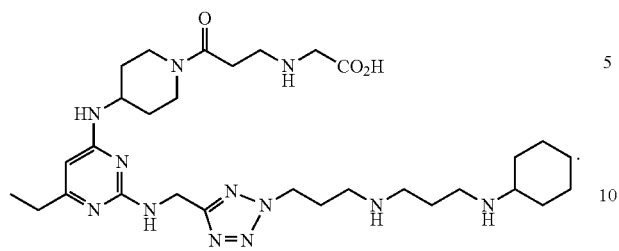
63

28. A pharmaceutical composition, comprising a compound of claim 1 and a pharmaceutically acceptable carrier thereof.

29. A method of mobilizing hematopoietic stem cells (HSC) and endothelial progenitor cells (EPC) into the peripheral circulation, the method comprising contacting HSC and EPC with an effective amount of a compound of claim 1.

30. A method of treating hepatocellular carcinoma, rheumatoid arthritis, kidney injury, myocardial infarction, or mild traumatic brain injury, the method comprising administering to a subject in need thereof an effective amount of a compound of claim 1.

31. A method of treating hepatocellular carcinoma, the method comprising administering to a subject in need thereof an effective amount of a compound of claim 1.

* * * * *